US012211606B2

(12) United States Patent
Littlefield et al.

(10) Patent No.: US 12,211,606 B2
(45) Date of Patent: Jan. 28, 2025

(54) COMPARING PERFORMANCE FEEDBACK WITH OUTPUT OF PERFORMANCE MODEL TO CALIBRATE RESOURCE CONSUMPTION CONTROL SYSTEM AND IMPROVE PERFORMANCE CRITERION

(71) Applicant: Fuelogics, LLC, Bothell, WA (US)

(72) Inventors: Scott Littlefield, Bothell, WA (US); Susan Lewis, Bothell, WA (US)

(73) Assignee: Fuelogics, LLC, Bothell, WA (US)

( * ) Notice: Subject to any disclaimer, the term of this patent is extended or adjusted under 35 U.S.C. 154(b) by 293 days.

(21) Appl. No.: 16/243,806

(22) Filed: Jan. 9, 2019

(65) Prior Publication Data
US 2019/0196421 A1 Jun. 27, 2019

Related U.S. Application Data

(63) Continuation of application No. 15/851,598, filed on Dec. 21, 2017, now Pat. No. 11,398,302.

(51) Int. Cl.
*G16H 20/60* (2018.01)
*G06Q 10/0639* (2023.01)

(52) U.S. Cl.
CPC ......... *G16H 20/60* (2018.01); *G06Q 10/0639* (2013.01); *G06Q 10/06395* (2013.01)

(58) Field of Classification Search
None
See application file for complete search history.

(56) References Cited

U.S. PATENT DOCUMENTS

2002/0019585 A1* 2/2002 Dickinson .......... A61B 5/02438
600/300
2004/0171925 A1* 9/2004 Kirchhoff .......... G01G 19/4146
600/407

(Continued)

FOREIGN PATENT DOCUMENTS

WO WO-2016065463 A1 * 5/2016 ............. G16H 20/30

OTHER PUBLICATIONS

United States Olympic Committee, Athlete's Plate, retrieved from the Internet at https://www.teamusa.org/About-the-USOC/Athlete-Development/Sport-Performance/Nutrition/Athlete-Factsheets-and-Resources, accessed Oct. 18, 2017, 2 pages.

(Continued)

*Primary Examiner* — Ivan R Goldberg
(74) *Attorney, Agent, or Firm* — Bamert Regan PLLC

(57) ABSTRACT

Embodiments are directed to improving performance criterion in a control session. Information associated with an agent may be obtained. A predicted expenditure may be generated based on the information and a performance model. The predicted expenditure may be transformed into specific-units amounts of multiple resource types based on the characteristics information. Each specific-units amount may be transformed into a normalized-units amount based on one or more normalized-units amounts of one or more other resource types. An instruction may be provided to the agent based on the normalized-units amounts. Metrics based on monitoring the agent may be obtained. One or more portions of the metrics may be compared to one or more outputs of the performance model. One or more outputs of the model may be modified based on the comparison to increase a correlation between one or more outputs and the metrics.

45 Claims, 15 Drawing Sheets

(56) References Cited

U.S. PATENT DOCUMENTS

| | | | | |
|---|---|---|---|---|
| 2005/0004436 | A1* | 1/2005 | Nissila | A61B 5/1118 600/300 |
| 2008/0275348 | A1* | 11/2008 | Catt | A61B 5/1112 600/483 |
| 2010/0198605 | A1* | 8/2010 | Saulet | G16H 20/60 705/1.1 |
| 2015/0093725 | A1* | 4/2015 | Baarman | G06F 19/3475 434/127 |
| 2015/0107910 | A1* | 4/2015 | Villard | G01G 19/4146 177/25.12 |
| 2015/0285776 | A1* | 10/2015 | Miller-Kovach | G09B 5/02 426/2 |
| 2017/0201779 | A1* | 7/2017 | Publicover | H04N 21/4532 |
| 2018/0374385 | A1* | 12/2018 | Benefield | A63B 24/0062 |

OTHER PUBLICATIONS

Weight Watchers, web capture of web page located at www.weightwatchers.com/us/, retrieved from the Internet on Jan. 22, 2019, 3 pages.
Weijs, "Validity of predictive equations for resting energy expenditure in US and Dutch overweight and obese class I and II adults aged 18-65 y," Am J Clin Nutr 2008;88:959-970, retrieved from the Internet through ajcn.nutrition.org on Oct. 1, 2017.
Whybrow, et al., "The effect of an incremental increase in exercise on appetite, eating behaviour and energy balance in lean men and women feeding ad libitum," British J of Nutrition (2008), 100, 1109-1115, retrieved from the Internet at https://www.cambridge.org/core on Jan. 25, 2019.
Wycherley, et al., "Effects of energy-restricted high-protein, low-fat compared with standard-protein, low-fat diets: a meta-analysis of randomized controlled trials," Am J Clin Nutr 2012;96:1281-1298, retrieved from the Internet at https://academic.oup.com/ajcn/article-abstract/96/6/1281/4571449 on Jan. 25, 2019.
Canada's Dairy Industry at a Glance, Canadian Dairy Information Centre, Global butter consumption (kg per capita), located at http://www.dairyinfo.gc.ca/index_e.php?s1=dff-fcil&s2=cons&s3=consglo&s4=tb-bt, accessed on Oct. 26, 2017, 6 pages.
Acheson, et al., "Glycogen storage capacity and de novo lipogenesis during massive carbohydrate overfeeding in man," Am J Clin Nutr 1988;48:240-7, retrieved from the Internet at www.ajcn.org on Jul. 10, 2011.
"Adult Weight Management, AWM: Major Recommendations (2006)," Academy of Nutrition and Dietetics (A.N.D.), Evidence Analysis Library, printed on Dec. 18, 2015, from http://www.andeal.org, 23 pages.
Alajmi, et al., "Appetite and Energy Intake Responses to Acute Energy Deficits in Females versus Males," Medicine & Science in Sports & Exercise, Official Journal of the American College of Sports Medicine, 2015, pp. 412-420.
Almiron-Roig, et al., "Estimating food portions. Influence of unit number, meal type and energy density," Appetite, Dec. 1, 2013; 71:95-103, retrieved from the Internet on Jan. 22, 2019, at https://www.ncbi.nlm.nih.gov/pmc/articles/PMC3857597/.
Andrews, et al., "Forget calorie counting," Precision Nutrition, 22 pages, retrieved from the Internet on Jan. 22, 2019, at https://www.precisionnutrition.com/calorie-control-guide.
Antonio et al., "The effects of consuming a high protein diet (4.4 g/kg/d) on body composition in resistance-trained individuals," Journal of the International Society of Sports Nutrition, 2014, 11:19, 6 pages.
Aragon, et al., "International society of sports nutrition position stand: diets and body composition," Journal of the International Society of Sports Nutrition, 2017, 14:16, 19 pages.
Atkinson, et al., "International Tables of Glycemic Index and Glycemic Load Values: 2008," Diabetes Care, vol. 31, No. 12, Dec. 2008, pp. 2281-2283.
Avatar Nutrition, web capture of web page located at www.avatarnutrition.com, retrieved on the Internet on Jan. 22, 2019.
Beggs, et al., "The Impact of Nutritional Counseling in Conjunction with Co-active Coaching on Behavior Change of Varsity Female Rowers," Sports Nutr Ther 2016; 1:3, 8 pages.
Bucher, et al., "Position paper on the need for portion-size education and a standardised unit of measurement," Health Promotion J of Australia, 2016, 4 pages.
Carpenter, et al., "Accurate Estimation of Energy Requirements of Young Patients," JPGN, vol. 60, No. 1, Jan. 2015, 7 pages.
Carter, et al., "Adherence to a Smartphone Application for Weight Loss Compared to Website and Paper Diary: Pilot Randomized Controlled Trial," J Med Internet Res., Apr. 2013;15(4): e32, 25 pages.
Celis-Morales, et al., "Effect of personalized nutrition on health-related behaviour change: evidence from the Food4Me European randomized controlled trial," International J of Epidemiology, 2017, vol. 46, No. 2, pp. 578-588.
Clayton et al., "Effect of Breakfast Omission on Energy Intake and Evening Exercise Performance," Medicine & Science in Sports & Exercise, 2015, 33 pages.
Finlayson, et al., "Acute compensatory eating following exercise is associated with implicit hedonic wanting for food," University of Leeds, Leeds, UK; Queensland University of Technology, Brisbane, Australia, at least as early as Oct. 31, 2017, 27 pages.
Fit Genie, web capture of web page located at www.fitgenieapp.com, retrieved from the Internet on Jan. 22, 2019.
Fitocracy, web capture of web page located at www.fitocracy.com, retrieved from the Internet on Jan. 22, 2019.
Frankenfield, et al., "Comparison of Predictive Equations for Resting Metabolic Rate in Healthy Nonobese and Obese Adults: A Systematic Review," J of the American Dietetic Association, May 2005, pp. 775-789.
Gannon et al., "Do African Americans have lower energy expenditure than Caucasians?," International J of Obesity, 2000, 24, 4-13.
Geisler, et al., "Inadequacy of Body Weight-Based Recommendations for Individual Protein Intake-Lessons from Body Composition Analysis," Nutrients, 2017, 9:23, 13 pages.
My Macros, web capture of web page located at www.getmymacros.com, retrieved from the Internet on Jan. 22, 2019.
Gonzalez, et al., "Breakfast and exercise contingently affect post-prandial metabolism and energy balance in physically active males," British J of Nutrition, Jan. 2013, 13 pages.
Haaf, et al., "Resting Energy Expenditure Prediction in Recreational Athletes of 18-35 Years: Confirmation of Cunningham Equation and an Improved Weight-Based Alternative," Plos One, vol. 9, Issue 10, e108460, Oct. 2014, 8 pages.
Hall et al., "Calorie for calorie, dietary fat restriction results in more body fat loss than carbohydrate restriction in people with obesity," Cell Metab., Sep. 1, 2015, 22(3): 427-436.
Hall, "What is the Required Energy Deficit per unit Weight Loss?," Int J Obes (Lond), Mar. 2008, 32(3): 573-576.
Helms, et al., "A Systematic Review of Dietary Protein During Caloric Restriction in Resistance Trained Lean Athletes: A Case for Higher Intakes," International J of Sport Nutrition and Exercise Metabolism, 2014, 24, 127-138.
Jumpertz, et al., "Energy-balance studies reveal associations between gut microbes, caloric load, and nutrient absorption in humans," Am J Clin Nutr, 2011, 94:58-65.
Levine, et al., "Role of Nonexercise Activity Thermogenesis in Resistance to Fat Gain in Humans," Science, Jan. 8, 1999, vol. 283, pp. 212-214.
Levinson, et al., "My Fitness Pal Calorie Tracker Usage in the Eating Disorders," Eat Behav., Dec. 2017, 27:14-16.
Lichtman, et al., "Discrepancy Between Self-Reported and Actual Caloric Intake and Exercise in Obese Subjects," The New England J of Medicine, Dec. 31, 1992, 327(27):1893-1898.
Longland, et al., "Higher compared with lower dietary protein during an energy deficit combined with intense exercise promotes greater lean mass gain and fat mass loss: a randomized trial," Am J Clin Nutr 2016; 103:738-746.
Lose It!, web capture of web page located at www.loseit.com, retrieved from the Internet on Jan. 22, 2019.
Loureiro, et al., "Basal Metabolic Rate of Adolescent Modern Pentathlon Athletes: Agreement between Indirect Calorimetry and

(56) References Cited

OTHER PUBLICATIONS

Predictive Equations and the Correlation with Body Parameters," Plos One, Nov. 16, 2015, 12 pages.

Lucan, et al., "How calorie-focused thinking about obesity and related diseases may mislead and harm public health. An alternative," Public Health Nutrition, 2014, 18(4):571-581.

Mueller, et al., "Changes in Energy Expenditure with Weight Gain and Weight Loss in Humans," Curr Obes Rep (2016) 5:413-423.

Myfitnesspal, web capture of web page located at www.myfitnesspal.com, retrieved from the Internet on Jan. 22, 2019.

Precision Nutrition, web capture of web page located at www.precisionnutrition.com/calorie-control-guide, retrieved from the Internet on Jan. 22, 2019.

Renaissance Periodization, web capture of web page located at www.renaissanceperiodization.com, retrieved from the Internet on Jan. 22, 2019.

Simpson, et al., "Calorie Counting and Fitness Tracking Technology: Associations with Eating Disorder Symptomatology," Eatbeh(2017), doi: 10.1016/j.eatbeh.2017.02.002, 19 pages.

Solbrig, et al., "People trying to lose weight dislike calorie counting apps and want motivational support to help them achieve their goals," Internet Interventions 7 (2017), pp. 23-31.

Thomas, et al., "Position of the Academy of Nutrition and Dietetics, Dietitians of Canada, and the American College of Sports Medicine: Nutrition and Athletic Performance," J Acad Nutr Diet. 2016;116(3):501-528.

Tipton, "Nutritional Support for Exercise-Induced Injuries," Sports Med (2015) 45 (Suppl 1):S93-S104.

United States Department of Agriculture, Supertracker, located at https://www.supertracker.usda.gov/myplan.aspx, accessed on Oct. 18, 2017, 3 pages.

United States Department of Agriculture, All About Oils, retrieved from the Internet at https://www.choosemyplate.gov/oils, on Jan. 22, 2019, 2 pages.

United States Department of Agriculture, All about the Vegetable Group, retrieved from the Internet at https://www.choosemyplate.gov/vegetables, on Jan. 22, 2019, 2 pages.

United States Department of Agriculture, Center for Nutrition Policy and Promotion, "Healthy US-Style Pattern-Recommended Intake Amounts," retrieved from the Internet at https://www.cnpp.usda.gov/sites/default/files/usda_food_patterns/HealthyUS-StylePattern-RecommendedIntakeAmounts.pdf on Jan. 22, 2019, 3 pages.

United States Department of Agriculture, Center for Nutrition Policy and Promotion, "What's My Plate All About?," retrieved from the Internet at https://choosemyplate-prod.azureedge.net/sites/default/files/printablematerials/2013-WhatsMyPlateAllAboutInfographic.pdf on Jan. 22, 2019, 1 page.

\* cited by examiner

COMPARING PERFORMANCE FEEDBACK WITH OUTPUT OF PERFORMANCE MODEL TO CALIBRATE RESOURCE CONSUMPTION CONTROL SYSTEM AND IMPROVE PERFORMANCE CRITERION

PRIORITY CLAIM

This application is a continuation of U.S. patent application Ser. No. 15/851,598, entitled "COMPARING PERFORMANCE FEEDBACK WITH OUTPUT OF PERFORMANCE MODEL TO CALIBRATE RESOURCE CONSUMPTION CONTROL SYSTEM AND IMPROVE PERFORMANCE CRITERION", filed on Dec. 21, 2017, which is hereby incorporated by reference.

TECHNICAL FIELD

The present invention relates generally to controlling resource consumption and, more particularly, but not exclusively, to controlling resource consumption based on a comparison of performance feedback and the output of a performance model.

BACKGROUND

Control systems that control agents' resource consumption typically provide poor estimates of individual consumption needs. For example, the typical control system often employs inaccurate models. Control systems that control agents' resource consumption also typically struggle to effectively communicate the estimated individual consumption needs. For example, the typical control system often employs inconsistent measurement units, leaving the agent to resolve discrepancies. Control systems that control agents' resource consumption additionally typically struggle to adapt to variations associated with the agents that are difficult to measure. For example, the typical control system often fails to account for poor consumption measurement or tracking by an agent or for characteristic anomalies associated with the agent, such as variances in construction.

Human specialists have sometimes attempted to intervene in attempt to account for the deficiencies of the typical control systems. Human intervention, however, typically fails to accurately translate the inconsistent measurement units employed by the typical control system. Thus, it is with respect to these considerations and others that the present invention has been made.

BRIEF DESCRIPTION OF THE DRAWINGS

Non-limiting and non-exhaustive embodiments of the present innovations are described with reference to the following drawings. In the drawings, like reference numerals refer to like parts throughout the various figures unless otherwise specified. For a better understanding of the described innovations, reference will be made to the following Detailed Description of the Various Embodiments, which is to be read in association with the accompanying drawings, wherein.

DETAILED DESCRIPTION OF THE VARIOUS EMBODIMENTS

Figure 1:
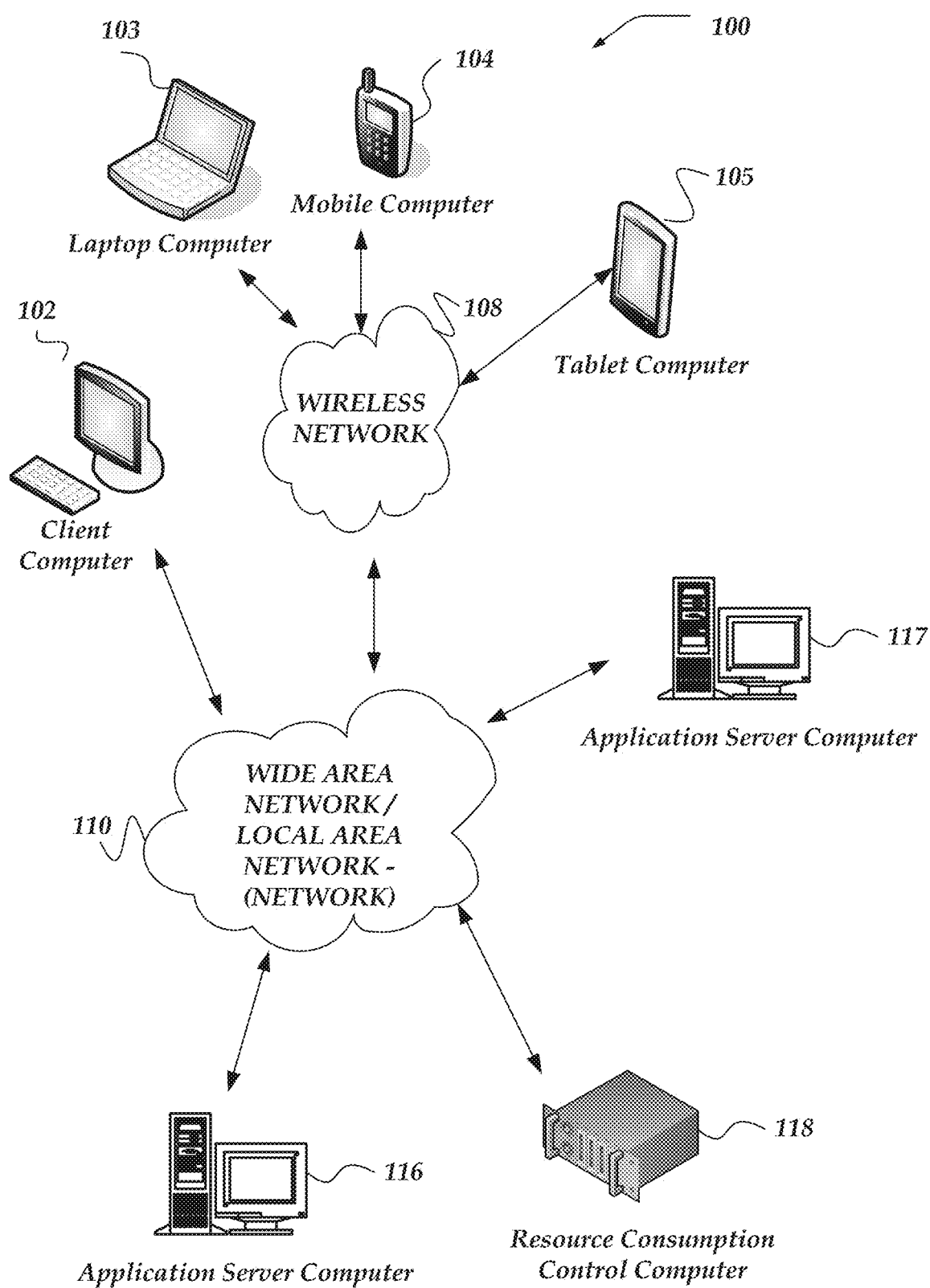
FIG. 1 illustrates a schematic representation of an example system environment in which various embodiments may be implemented.

Various embodiments now will be described more fully hereinafter with reference to the accompanying drawings, which form a part hereof, and which show, by way of illustration, specific example embodiments by which the invention may be practiced. The embodiments may, however, be embodied in many different forms and should not be construed as limited to the embodiments set forth herein; rather, these embodiments are provided so that this disclosure will be thorough and complete and will fully convey the scope of the embodiments to those skilled in the art. Among other things, the various embodiments may be methods, systems, media, or devices. Accordingly, the various embodiments may take the form of an entirely hardware embodiment, an entirely software embodiment, or an embodiment combining software and hardware aspects. The following detailed description is, therefore, not to be taken in a limiting sense.

Throughout the specification and claims, the following terms take the meanings explicitly associated herein, unless the context clearly dictates otherwise. The phrase "in one embodiment" or "in one implementation" as used herein does not necessarily refer to the same embodiment or implementation, though it may. Furthermore, the phrase "in another embodiment" or "in another implementation" as used herein does not necessarily refer to a different embodiment or implementation, although it may. Thus, as described below, various embodiments or implementations may be readily combined, without departing from the scope or spirit of the invention.

In addition, as used herein, the term "or" is an inclusive "or" operator and is equivalent to the term "or," unless the context clearly dictates otherwise. The term "based on" is not exclusive and allows for being based on additional factors not described, unless the context clearly dictates otherwise. In addition, as used herein, the meanings of "a,"

"an," and "the" include plural references. Also, as used herein, plural references are intended to also disclose the singular, unless the context clearly dictates otherwise. For example, the term "metrics" is employed herein and is intended to reflect "one or more metrics" because only one metric may be employed or more than one metric may be employed. Moreover, one or more outputs may include multiple outputs, modifying the one or more outputs may include modifying a single one of the one or more outputs, and one or more modified outputs may include multiple outputs with a single one of the multiple outputs having been modified. The meaning of "in" includes "in" and "on." Further, as used herein, the terms "of" and "for" refer to both the meaning of the term "of" and the meaning of the term "for" in the sentence or phrase in which one or the other is employed (although they may have the same meaning), unless the context clearly dictates otherwise. For example, "a specific-units amount of a resource type" also teaches "a specific-units amount for a resource type." Also, as used herein, the use of "when" and "responsive to" do not imply that associated resultant actions are required to occur immediately or within a particular time period. Instead, they are used herein to indicate actions that may occur or be performed in response to one or more conditions being met, unless the context clearly dictates otherwise. Additionally, as used herein, the use of "exemplary" does not imply that other embodiments do not perform as well or are not as worthy of illustration. Instead, the term is used herein to emphasize that each element or function described by the term is an example element or function.

For example embodiments, the following terms are also used herein according to the corresponding meaning, unless the context clearly dictates otherwise.

As used herein, the term "resource" refers to an asset or service that can be distributed, shared, or otherwise provided. Examples of resources may include electricity, fuel (for example, wood, coal, diesel, gasoline, propane, nuclear fuel rods, food, or others), fuel additives (for example, anti-gelling additives, fuel stabilizers, lead additives, anti-knock additives, oil additives, oxidizers, neutron moderating materials, spices, vitamins, or others), or others.

As used herein, the term "agent" refers to a resource consumer. Examples of agents may include motors, engines, athletes, or others.

As used herein, the term "performance monitor" refers to a reviewer of agent performance. Examples of campaign monitors may include one or more computers, engines, specialists, or others that may review agent performance, intervene in control sessions on behalf of agents, provide additional feedback to the control system, provide additional control to agents, or report agent performance to supervising entities.

As used herein, the term "specific units" refers to units of measurement in a system of measurement that defines the units and the relationships between them, with the measurement system being nationally or internationally agreed upon by one or more government bodies. Examples of specific units include grams, meters, liters, or others in the metric system, pounds, feet, gallons, or others in the United States customary system (USCS or USC), or pounds, feet, gallons, or others in the imperial system.

As used herein, the term "normalized units" refers to units of measurement in a system of measurement that defines the units and, optionally, the relationships between them, with the measurement system being at least partially independent of nationally or internationally agreed upon standards of government bodies. Examples of normalized units include serving sizes. The United States Food and Drug Administration defines "Reference Amounts Customarily Consumed" (RACC) tables that are used by food manufacturers to determine the label serving sizes in household measures that are most appropriate to the food manufacturers' specific products using procedures in 21 C.F.R. § 101.9(b). In contrast to specific units (for example, a gram or a gallon), a normalized unit (for example, a serving size) may indicate an amount of mass, length, volume, or another measurable parameter. Also in contrast to specific units (for example, a gram or a gallon), a normalized unit (for example, a serving size) may indicate different amounts of mass, length, volume, or another measurable parameter based on the measured object. For example, the FDA RACC tables suggest employing the normalized unit of a serving size to refer to an amount of fluid ounces or milliliters for juices, a number of cups for cereals, and a number of pieces for bagels.

The following briefly describes example embodiments of the invention in order to provide a basic understanding of some aspects of the invention. This brief description is not intended as an extensive overview. It is not intended to identify key or critical elements or to delineate or otherwise narrow the scope. Its purpose is merely to present some concepts in a simplified form as a prelude to the more detailed description that is presented later.

Briefly stated, various embodiments are directed to improving performance criterion in a control session. In one or more of the various embodiments, characteristics information associated with an agent may be obtained. In some of the various embodiments, one or more outputs may be generated based on the characteristics information and a performance model. In some embodiments, the one or more outputs may include a predicted expenditure amount. In some embodiments, the predicted expenditure amount may be transformed into specific-units amounts of multiple resource types based on the characteristics information. In some embodiments, the specific-units amount of each of the multiple resource types may be transformed into a normalized-units amount of each of the multiple resource types based on one or more normalized-units amounts of one or more other resource types. In some embodiments, a consumption instruction may be provided to the agent based on the normalized-units amounts of the multiple resource types. In some embodiments, metrics that are based on the consumption instruction and a monitoring of the agent may be obtained. In some embodiments, one or more portions of the metrics may be compared to the one or more outputs of the performance model. In some embodiments, the one or more outputs may be modified based on the comparison to increase a correlation between the one or more outputs and the metrics. In some embodiments, a modified consumption instruction may be provided to the agent based on the one or more modified outputs.

In some embodiments, the metrics may indicate reported amounts of multiple resource types consumed by the agent in multiple intervals and may include performance feedback that indicates measured values of an agent characteristic in the multiple intervals.

In some embodiments, the metrics may include performance feedback that indicates a value of a measured agent characteristic in each of two or more intervals in each of two or more periods. In some embodiments, the value of the measured agent characteristic in each of the two or more intervals in each of the two or more periods may be evaluated to provide a first agent characteristic amount for a first one of the two or more periods and a second agent characteristic amount for a second one of the two or more periods. In some embodiments, the first agent characteristic amount may be evaluated based on the second characteristic amount to provide an obtained amount of change in the agent characteristic. In some embodiments, the obtained amount of change in the agent characteristic may be compared to the one or more outputs of the performance model. In some embodiments, the one or more outputs of the performance model may include a value of a predicted change in the agent characteristic based on the predicted expenditure amount.

In some embodiments, the metrics may indicate reportedly consumed amounts of specific units of the multiple resource types in multiple intervals and may include performance feedback that indicates a value of a measured change in an agent characteristic. In some embodiments, the reportedly consumed amount of specific units of each of the multiple resource types may be transformed into reportedly consumed amounts of normalized units of each of the multiple resource types based on the specific-units amount of each of the multiple resource types and the normalized-units amount of each of the multiple resource types. In some embodiments, the reportedly consumed amount of normalized units of each of the multiple resource types may be transformed into a total reportedly consumed amount of specific units of each of the multiple resource types based on one or more of the reportedly consumed amounts of normalized units of one or more other ones of the multiple resource types. In some embodiments, the value of the measured change in the agent characteristic may be compared to the one or more outputs of the performance model. In some embodiments, the one or more outputs of the performance model may include a value of a predicted change in the agent characteristic based on the predicted expenditure amount and the total reportedly consumed amounts of specific units of the multiple resource types.

In some embodiments, one or more portions of the characteristics information associated with the agent may indicate an impairment status of the agent. In some embodiments, transforming the predicted expenditure amount into the specific-units amounts of the multiple resource types may include increasing the specific-units amount of one of the multiple resource types based on the impairment status of the agent.

In some embodiments, the normalized-units amounts of the multiple resource types may be transformed into resource distribution information based on one or more portions of the characteristics information associated with the agent. In some embodiments, one or more portions of the resource distribution information may be transformed into the resource consumption instruction.

In some embodiments, one or more alerts may be provided to one or more performance monitors based on the comparison of the one or more portions of the metrics to the one or more outputs of the performance model indicating that performance of the agent diverged from performance of one or more groups of agents associated with the agent.

In some embodiments, the metrics may be obtained from a client computer of the agent.

Illustrative Operating Environment

FIG. 1 shows components of an example environment in which embodiments of the invention may be practiced. Not all of the components may be required to practice the invention, and variations in the arrangement and type of the components may be made without departing from the spirit or scope of the invention. As shown, system 100 of FIG. 1 includes local area networks (LANs)/wide area networks (WANs)—(network) 110, wireless network 108, client computers 102-105, Application Server Computer 116, Application Server Computer 117, Resource Consumption Control Computer 118, or others.

At least one embodiment of client computers 102-105 is described in more detail below in conjunction with FIG. 2. In one embodiment, at least some of client computers 102-105 may operate over one or more wired or wireless networks, such as networks 108, or 110. Generally, client computers 102-105 may include virtually any computer capable of communicating over a network to send and receive information, perform various online activities, offline actions, or others. In some embodiments, one or more of client computers 102-105 may be configured to operate within a business or other entity to perform a variety of services for the business or other entity. For example, client computers 102-105 may be configured to operate as a web server, firewall, client application, media player, mobile telephone, game console, desktop computer, or others. However, client computers 102-105 are not constrained to these services and may also be employed, for example, for end-user computing in other embodiments. It should be recognized that more or fewer client computers (as shown in FIG. 1) may be included within a system such as described herein, and embodiments are therefore not constrained by the number or type of client computers employed.

Computers that may operate as client computer 102 may include computers that typically connect using a wired or wireless communications medium such as personal computers, multiprocessor systems, microprocessor-based or programmable electronic devices, network PCs, or others. In some embodiments, client computers 102-105 may include virtually any portable computer capable of connecting to another computer and receiving information, such as laptop computer 103, mobile computer 104, tablet computers 105, or others. However, portable computers may also include other portable computers such as cellular telephones, display pagers, radio frequency (RF) devices, infrared (IR) devices, Personal Digital Assistants (PDAs), handheld computers, wearable computers, integrated devices combining one or more of the preceding computers, or others. As such, client computers 102-105 typically range widely in terms of capabilities and features. Moreover, client computers 102-105 may access various computing applications, including a browser, or other web-based application.

A web-enabled client computer may include a browser application that is configured to send requests and receive responses over the web. The browser application may be configured to receive or display graphics, text, multimedia, or others, employing virtually any web-based language. In some embodiments, the browser application is enabled to employ JavaScript, HyperText Markup Language (HTML), eXtensible Markup Language (XML), JavaScript Object Notation (JSON), Cascading Style Sheets (CSS), or others to display or send a message. In some embodiments, a user of the client computer may employ the browser application to perform various activities over a network (online). However, another application may also be used to perform various online activities.

Client computers 102-105 also may include one or more other client applications that are configured to receive or send content between another computer. The client application may include a capability to send or receive content or other information or signals. The client application may further provide information that identifies itself, including a type, capability, name, or others. In some embodiments, client computers 102-105 may uniquely identify themselves through any of a variety of mechanisms, including an Internet Protocol (IP) address, a phone number, Mobile Identification Number (MIN), an electronic serial number (ESN), a client certificate, or other device identifier. Such information may be provided in one or more network packets or other collections of data, sent between other client computers, application server computer 116, application server computer 117, resource consumption control computer 118, or other computers.

Client computers 102-105 may further be configured to include a client application that enables an end-user to log into an end-user account that may be managed by another computer, such as application server computer 116, application server computer 117, resource consumption control computer 118, or others. Such an end-user account, in some examples, may be configured to enable the end-user to manage one or more online activities, including in some examples, project management, software development, system administration, configuration management, search activities, social networking activities, browse various websites, communicate with other users, or others. Further, client computers may be arranged to enable users to provide configuration information, or others, to resource consumption control computer 118. Also, client computers may be arranged to enable users to display reports, interactive user-interfaces, or results provided by resource consumption control computer 118.

Wireless network 108 is configured to couple client computers 103-105 and its components with network 110. Wireless network 108 may include any of a variety of wireless sub-networks that may further overlay stand-alone ad-hoc networks or others to provide an infrastructure-oriented connection for client computers 103-105. Such sub-networks may include mesh networks, Wireless LANs (WLANs), cellular networks, or others. In one embodiment, the system may include more than one wireless network.

Wireless network 108 may further include an autonomous system of terminals, gateways, routers, or others connected by wireless radio links or others. These connectors may be configured to move freely and randomly and organize themselves arbitrarily, such that the topology of wireless network 108 may change rapidly.

Wireless network 108 may further employ a plurality of access technologies including 2nd (2G), 3rd (3G), 4th (4G), 5th (5G) generation radio access for cellular systems, WLAN, Wireless Router (WR) mesh, or others. Access technologies such as 2G, 3G, 4G, 5G, and future access networks may enable wide area coverage for mobile computers, such as client computers 103-105 with various degrees of mobility. In some examples, wireless network 108 may enable a radio connection through a radio network access such as Global System for Mobile communication (GSM), General Packet Radio Services (GPRS), Enhanced Data rates for GSM Evolution (EDGE), code division multiple access (CDMA), time division multiple access (TDMA), Wideband Code Division Multiple Access (WCDMA), High Speed Downlink Packet Access (HSDPA), Long Term Evolution (LTE), and others. In essence, wireless network 108 may include virtually any wireless communication mechanism by which information may travel between client computers 103-105 and another computer, network, a cloud-based network, a cloud instance, or others.

Network 110 is configured to couple network computers with other computers, including, application server computer 116, application server computer 117, resource consumption control computer 118, client computers 102-105 through wireless network 108, or others. Network 110 is enabled to employ any form of computer readable media for communicating information from one electronic device to another. Also, network 110 can include the Internet in addition to local area networks (LANs), wide area networks (WANs), direct connections, such as through a universal serial bus (USB) port, Ethernet port, or other forms of computer-readable media. On an interconnected set of LANs, including those based on differing architectures and protocols, a router acts as a link between LANs, enabling messages to be sent from one to another. In addition, communication links within LANs typically include twisted wire pair or coaxial cable, while communication links between networks may utilize analog telephone lines, full or fractional dedicated digital lines including T1, T2, T3, and T4, or other carrier mechanisms including, for example, E-carriers, Integrated Services Digital Networks (ISDNs), Digital Subscriber Lines (DSLs), wireless links including satellite links, or other communications links known to those skilled in the art. Moreover, communication links may further employ any of a variety of digital signaling technologies, including, for example, DS-0, DS-1, DS-2, DS-3, DS-4, OC-3, OC-12, OC-48, or others. Furthermore, remote computers and other related electronic devices could be remotely connected to either LANs or WANs via a modem and temporary telephone link. In one embodiment, network 110 may be configured to transport information of an Internet Protocol (IP).

Additionally, communication media typically embodies computer readable instructions, data structures, program modules, or other transport mechanism and includes any information non-transitory delivery media or transitory delivery media. By way of example, communication media includes wired media such as twisted pair, coaxial cable, fiber optics, wave guides, and other wired media and wireless media such as acoustic, RF, infrared, or other wireless media.

One embodiment of application server computer 116 or application server computer 117 is described in more detail below in conjunction with FIG. 3. Briefly, however, application server computer 116 or application server computer 117 includes virtually any network computer capable of hosting applications or providing services in network environment.

One embodiment of resource consumption control computer 118 is described in more detail below in conjunction with FIG. 3. Briefly, however, resource consumption control computer 118 may include virtually any network computer capable of providing resource consumption instructions to one or more agents to control resource consumption by the one or more agents, obtain metrics associated with the one or more agents, compare the obtained metrics to the outputs of one or more performance models, calibrate resource consumption control computer 118 based on the comparison, or provide modified resource consumption instructions to the one or more agents to improve performance criterion.

Although FIG. 1 illustrates application server computer 116, application server computer 117, and resource consumption control computer 118, each as a single computer, the innovations or embodiments are not so limited. For example, one or more functions of application server computer 116, application server computer 117, resource consumption control computer 118, or others, may be distributed across one or more distinct network computers. Moreover, in one or more embodiments, resource consumption control computer 118 may be implemented using a plurality of network computers. Further, in one or more of the various embodiments, application server computer 116, application server computer 117, or resource consumption control computer 118 may be implemented using one or more cloud instances in one or more cloud networks. Accordingly, these innovations and embodiments are not to be construed as being limited to a single environment, and other configurations and other architectures are also envisaged.

Illustrative Client Computer

Figure 2:
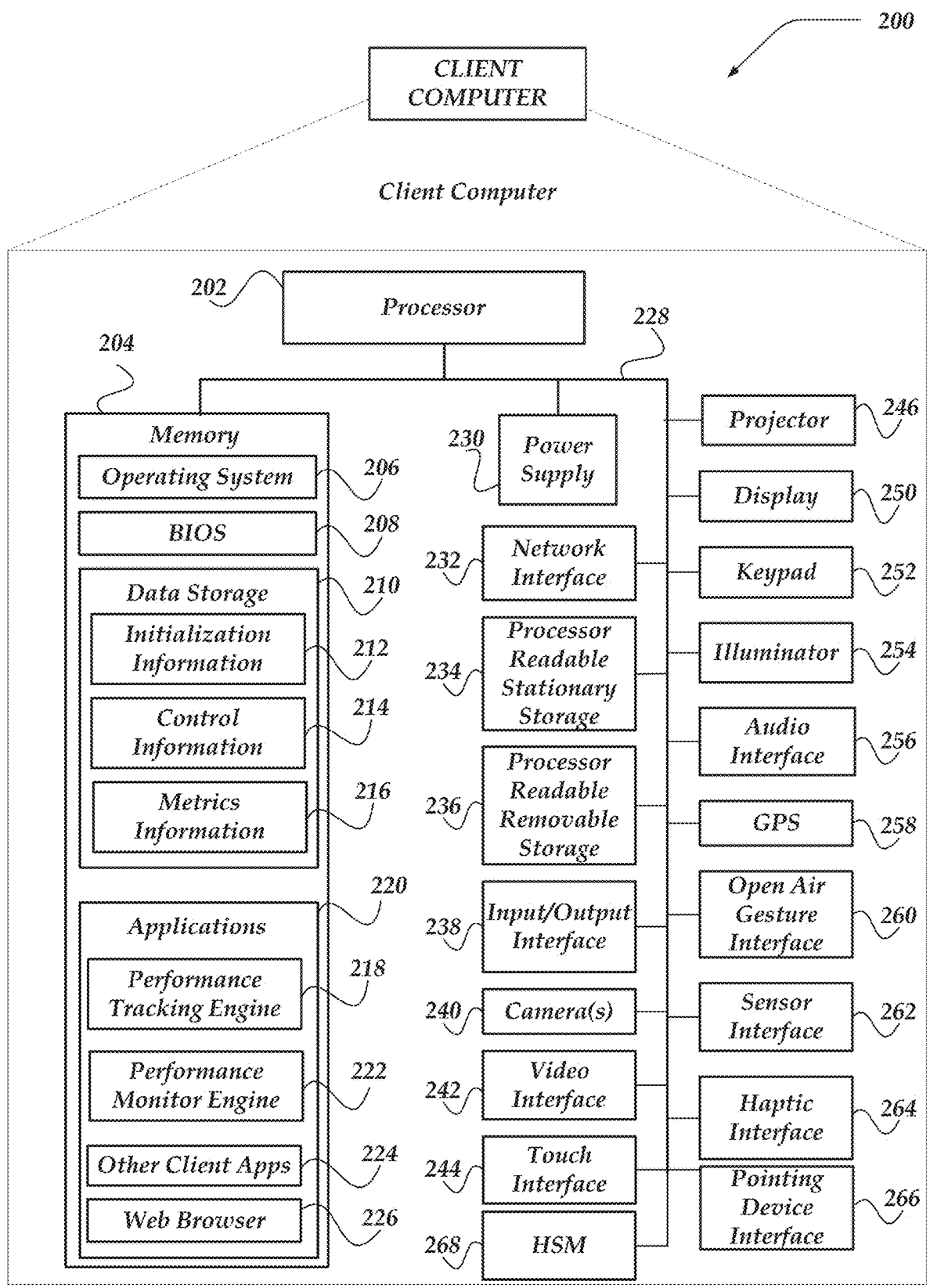
FIG. 2 shows a schematic representation of an example client computer.

FIG. 2 shows one embodiment of client computer 200 that may include many more or fewer components than those shown. Client computer 200 may represent, for example, at least one embodiment of mobile computers or client computers shown in FIG. 1.

Client computer 200 may include processor 202 in communication with memory 204 via bus 228. Client computer 200 may also include power supply 230, network interface 232, audio interface 256, display 250, keypad 252, illuminator 254, video interface 242, input/output interface 238, haptic interface 264, global positioning systems (GPS) receiver or transceiver 258, open air gesture interface 260, sensor interface 262 (for example, a temperature interface, biometric interface, accelerometer interface, weight scale interface, or others), camera(s) 240, projector 246, pointing device interface 266, processor-readable stationary storage device 234, or processor-readable removable storage device 236. Client computer 200 may optionally communicate with a base station (not shown) or directly with another computer. And in some embodiments, although not shown, a gyroscope may be employed within client computer 200 to measuring or maintaining an orientation of client computer 200.

Power supply 230 may provide power to client computer 200. A rechargeable or non-rechargeable battery may be used to provide power. The power may also be provided by an external power source, such as an AC adapter or a powered docking cradle that supplements or recharges the battery.

Network interface 232 includes circuitry for coupling client computer 200 to one or more networks and is constructed for use with one or more communication protocols and technologies including protocols and technologies that implement any portion of the Open Systems Interconnection model (OSI model), such as global system for mobile communication (GSM), CDMA, time division multiple access (TDMA), UDP, TCP/IP, SMS, MMS, GPRS, WAP, UWB, WiMax, SIP/RTP, EDGE, WCDMA, LTE, UMTS, orthogonal frequency-division multiplexing (OFDM), CDMA2000, EV-DO, HSDPA, or any of a variety of other wireless communication protocols. Network interface 232 is sometimes known as a transceiver, transceiving device, or network interface card (NIC).

Audio interface 256 may be arranged to produce and receive audio signals such as the sound of a human voice. For example, audio interface 256 may be coupled to a speaker and microphone (not shown) to enable telecommunication with others or generate an audio acknowledgement for some action. A microphone in audio interface 256 can also be used for input to or control of client computer 200, e.g., using voice recognition, detecting touch based on sound, or others.

Display 250 may be a liquid crystal display (LCD), gas plasma, electronic ink, light emitting diode (LED), Organic LED (OLED) or any other type of light reflective or light transmissive display that can be used with a computer. Display 250 may also include a touch interface 244 arranged to receive input from an object such as a stylus or a digit from a human hand and may use resistive, capacitive, surface acoustic wave (SAW), infrared, radar, or other technologies to sense touch or gestures.

Projector 246 may be a remote handheld projector or an integrated projector that is capable of projecting an image on a remote wall or any other reflective object such as a remote screen.

Video interface 242 may be arranged to capture video images, such as a still photo, a video segment, an infrared video, or others. For example, video interface 242 may be coupled to a digital video camera, a web-camera, or others. Video interface 242 may comprise a lens, an image sensor, or other electronics. Image sensors may include a complementary metal-oxide-semiconductor (CMOS) integrated circuit, charge-coupled device (CCD), or any other integrated circuit for sensing light.

Keypad 252 may comprise any input device arranged to receive input from a user. For example, keypad 252 may include a push button numeric dial or a keyboard. Keypad 252 may also include command buttons that are associated with selecting and sending images.

Illuminator 254 may provide a status indication or provide light. Illuminator 254 may remain active for specific periods of time or in response to event messages. For example, when illuminator 254 is active, it may backlight the buttons on keypad 252 and stay on while the client computer is powered. Also, illuminator 254 may backlight these buttons in various patterns when particular actions are performed, such as dialing another client computer. Illuminator 254 may also cause light sources positioned within a transparent or translucent case of the client computer to illuminate in response to actions.

Further, client computer 200 may also comprise hardware security module (HSM) 268 for providing additional tamper resistant safeguards for generating, storing or using security/cryptographic information, such as keys, digital certificates, passwords, passphrases, two-factor authentication information, or others. In some embodiments, hardware security module may be employed to support one or more standard public key infrastructures (PKI) and may be employed to generate, manage, or store keys pairs or others. In some embodiments, HSM 268 may be a stand-alone computer or may be arranged as a hardware card that may be added to a client computer.

Client computer 200 may also comprise input/output interface 238 for communicating with external peripheral devices or other computers such as other client computers and network computers. The peripheral devices may include an audio headset, virtual reality headsets, display screen glasses, remote speaker system, remote speaker and microphone system, or others. Input/output interface 238 can utilize one or more technologies, such as Universal Serial Bus (USB), Infrared, Wi-Fi™, WiMax, Bluetooth™, or others.

Input/output interface 238 may also include one or more sensors for determining geolocation information (e.g., GPS), monitoring electrical power conditions (e.g., voltage sensors, current sensors, frequency sensors, and so on), monitoring weather (e.g., thermostats, barometers, anemometers, humidity detectors, precipitation scales, or others), or others. Sensors may be one or more hardware sensors that collect or measure data that is external to client computer 200.

Haptic interface 264 may be arranged to provide tactile feedback to a user of the client computer. For example, the haptic interface 264 may be employed to vibrate client computer 200 in a particular way when another user of a computer is calling. Sensor interface 262 may be used to provide a temperature measurement input of a user of client computer 200 or equipment associated with client computer 200 (for example, from one or more wearable sensor or others), a temperature changing output to the user or equipment of client computer 200, an accelerometer measurement input (for example, from a pedometer or others), a weight input of the user, equipment, or resources consumed by the user or equipment (for example, from a scale or others), biometric measurement inputs of the user or equipment (for example, from one or more wearable sensors or others), volumetric flow measurement inputs of resources consumed or provided in one or more intake sessions to the user or equipment (for example, one or more impellers or others), or other sensor inputs that may facilitate tracking performance or one or more other characteristics information of the user or equipment, such as activity rating, lifestyle rating, impairment status, or others (for example, one or more wearable sensors available under the mark FITBIT or others). In some embodiments, the one or more sensors may be part of client computer 200. In other embodiments, the one or more sensors may be separate and discrete from client computer 200. Open air gesture interface 260 may sense physical gestures of a user of client computer 200, for example, by using single or stereo video cameras, radar, a gyroscopic sensor inside a computer held or worn by the user, or others. In some embodiments, camera 240 may be used to track physical eye movements of a user of client computer 200. In some embodiments, camera 240 may be used to track resources consumed or accepted during one or more intake sessions by the user or equipment associated with client computer 200. For example, one or more applications 220 in client computer may perform image recognition processes with regard to one or more images of resources captured by camera 240 to generate one or more values that represent one or more resource types or resource amounts consumed by the user or equipment. As another example, the one or more images of resources captured by camera 240 may be communicated over one or more networks to one or more other computers (for example, one or more network computers 300, performance monitors 404, resource consumption control computers 406, or others) to generate the one or more values that represent one or more resource types or resource amounts consumed by the user or equipment, either based on image recognition processes or user inputs to one or more user interface components based on one or more displays displaying one or more portions of the one or more images.

GPS receiver or transceiver 258 can determine the physical coordinates of client computer 200 on the surface of the Earth, which typically outputs a location as latitude and longitude values. GPS receiver or transceiver 258 can also employ other geo-positioning mechanisms, including triangulation, assisted GPS (AGPS), Enhanced Observed Time Difference (E-OTD), Cell Identifier (CI), Service Area Identifier (SAI), Enhanced Timing Advance (ETA), Base Station Subsystem (BSS), or others, to further determine the physical location of client computer 200 on the surface of the Earth. It is understood that under different conditions, GPS receiver or transceiver 258 can determine a physical location for client computer 200. In one or more embodiments, however, client computer 200 may, through other components, provide other information that may be employed to determine a physical location of the client computer, including, for example, a Media Access Control (MAC) address, IP address, or others.

In one or more of the various embodiments, one or more applications (for example, one or more operating systems 206, performance tracking engines 218, performance monitor engines 222, web browsers 226, or others) may be arranged to employ geo-location information to select one or more localization features, such as one or more time zones, languages, currencies, calendar formatting, geographical regions or territories, or others. In some of the various embodiments, localization features may be used in one or more portions of file system object meta-data, file system objects, file systems, user-interfaces, reports, internal processes, databases, or others. In some embodiments, geo-location information used for selecting localization information may be provided by GPS receiver or transceiver 258. Also, in some embodiments, geo-location information may include information provided using one or more geo-location protocols over one or more networks, such as wireless network 108, network 110, or others.

Human interface components can be peripheral devices that are physically separate from client computer 200, allowing for remote input or output to client computer 200. For example, information routed as described here through human interface components such as display 250 or keyboard 252 can instead be routed through network interface 232 to appropriate human interface components located remotely. Examples of human interface peripheral components that may be remote include audio devices, pointing devices, keypads, displays, cameras, projectors, and others. These peripheral components may communicate over a Pico Network such as Bluetooth™ Zigbee™, or others. Some examples of a client computer with such peripheral human interface components include a wearable computer, which might include a remote pico projector along with one or more cameras that remotely communicate with a separately located client computer to sense a user's gestures toward portions of an image projected by the pico projector onto a reflected surface such as a wall or the user's hand.

A client computer may include web browser application 226 that is configured to receive and to send web pages, web-based messages, graphics, text, multimedia, or others. The client computer's browser application may employ virtually any programming language, including a wireless application protocol (WAP) messages or others. In some embodiments, the browser application is enabled to employ Handheld Device Markup Language (HDML), Wireless Markup Language (WML), WMLScript, JavaScript, Standard Generalized Markup Language (SGML), HyperText Markup Language (HTML), eXtensible Markup Language (XML), HTML5, or others.

Memory 204 may include RAM, ROM, or other types of memory. Memory 204 illustrates an example of computer-readable storage media (devices) for storage of information such as computer-readable instructions, data structures, program modules, or other data. Memory 204 may store BIOS 208 for controlling low-level operation of client computer 200. The memory may also store operating system 206 for controlling the operation of client computer 200. It will be appreciated that this component may include a general-purpose operating system such as a version of UNIX or LINUX™ or a specialized client computer communication operating system such as Windows Phone™ or the Symbian® operating system. The operating system may include or interface with a Java virtual machine module that enables control of hardware components or operating system operations via Java application programs.

Memory 204 may further include one or more data storage 210, which can be utilized by client computer 200 to store, among other things, applications 220 or other data. For example, data storage 210 may also be employed to store information that describes various capabilities of client computer 200. The information may then be provided to another device or computer based on any of a variety of methods, including being sent as part of a header during a communication, sent upon request, or others. Data storage 210 may also be employed to store social networking information including address books, buddy lists, aliases, user profile information, or others. Data storage 210 may further include program code, data, algorithms, or others, for use by a processor, such as processor 202 to execute and perform actions. In some embodiments, at least some of data storage 210 might also be stored on another component of client computer 200, including non-transitory processor-readable removable storage device 236, processor-readable stationary storage device 234, or even external to the client computer. Data storage 210 may include, for example, initialization information 212, control information 214, metrics information 216, or others. Initialization information 212 may include information for or obtained by initializing one or more control sessions. Control information 214 may include information obtained from resource consumption control computer 118, such as resource consumption instructions. Metrics information 216 may include one or more values of one or more metrics associated with one or more active control sessions, completed control sessions, performance monitors, control session users or agents, or others.

Applications 220 may include computer executable instructions which, when executed by client computer 200, transmit, receive, or otherwise process instructions and data. Applications 220 may include, for example, performance tracking engine 218, performance monitor engine 222, other client applications 224, web browser 226, or others that perform actions further described below. In one or more of the various embodiments, one or more applications 220 (for example, one or more performance tracking engines 218, performance monitor engines 222, other client applications 224, web browser 226, or others) may be separate and discrete from one or more other applications 220. In some of the various embodiments, one or more applications 220 may include one or more portions of one or more other applications 220 (for example, one or more portions of the one or more other applications 220 may include one or more processes, programming concepts, or others within the one or more applications 220). Client computers 200 may be arranged to exchange communications, such as queries, searches, messages, notification messages, event messages, alerts, performance metrics, log data, API calls, or others with application servers or network monitoring computers.

Other examples of application programs include calendars, search programs, email client applications, IM applications, SMS applications, Voice Over Internet Protocol (VOIP) applications, contact managers, task managers, transcoders, database programs, word processing programs, security applications, spreadsheet programs, games, search programs, or others.

Additionally, in one or more embodiments (not shown in the figures), client computer 200 may include one or more embedded logic hardware devices instead of one or more CPUs, such as an Application Specific Integrated Circuits (ASICs), Field Programmable Gate Arrays (FPGAs), Programmable Array Logics (PALs), or others. The one or more embedded logic hardware devices may directly execute embedded logic to perform actions. Also, in one or more embodiments (not shown in the figures), client computer 200 may include one or more hardware microcontrollers instead of one or more CPUs. In some embodiments, the one or more microcontrollers may directly execute their own embedded logic to perform actions and access its own internal memory and its own external Input and Output Interfaces (e.g., hardware pins or wireless transceivers) to perform actions as a System On a Chip (SOC) or others.

Illustrative Network Computer

Figure 3:
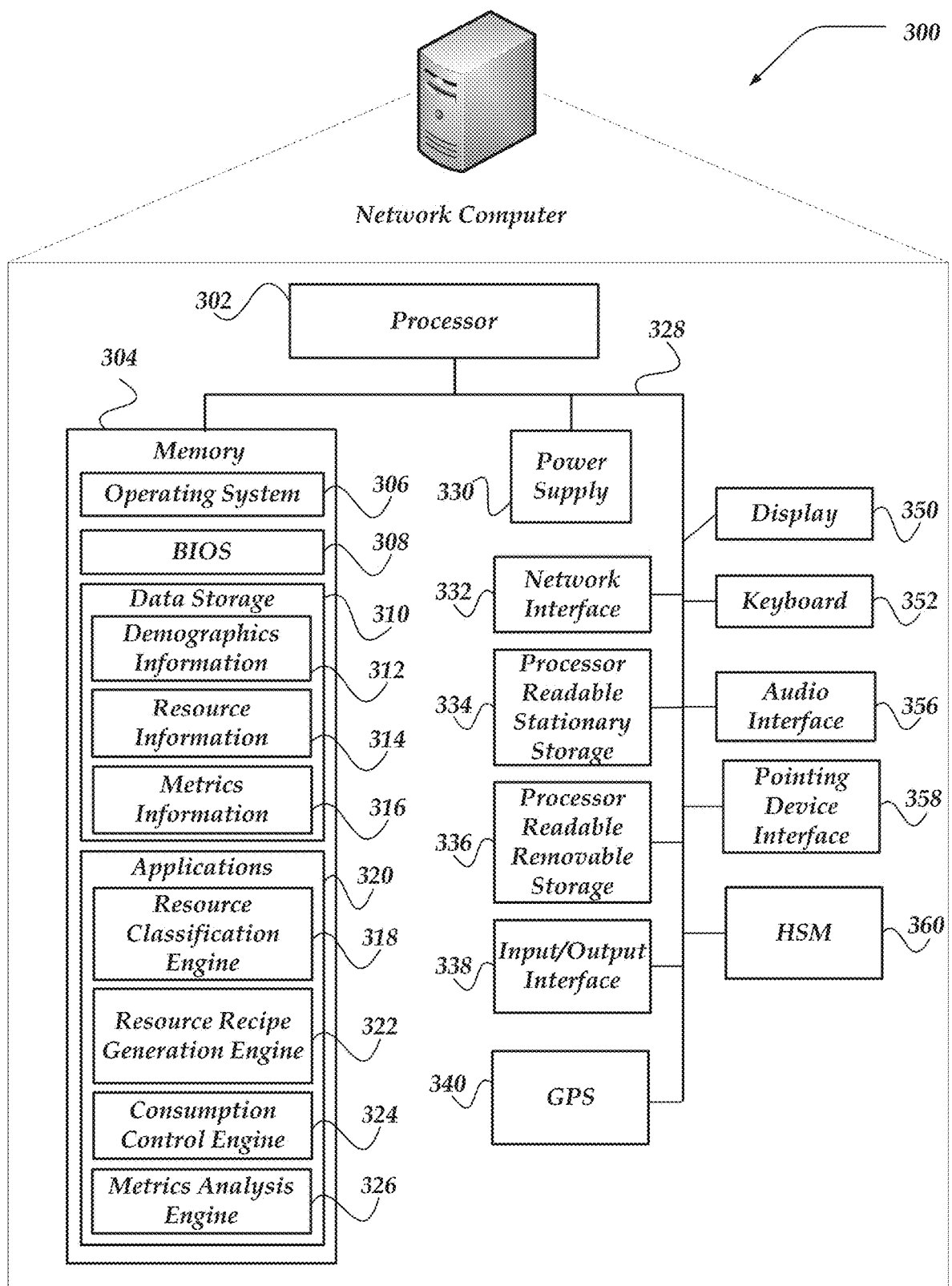
FIG. 3 illustrates a schematic representation of an example network computer.

FIG. 3 shows one example embodiment of network computer 300 that may be included in a system implementing one or more of the various embodiments. Network computer 300 may include many more or fewer components than those shown in FIG. 3. However, the components shown are sufficient to disclose an illustrative embodiment for practicing these innovations. Network computer 300 may represent, for example, one embodiment of one or more of application server computer 116, application server computer 117, or resource consumption control computer 118 of FIG. 1.

As shown in the figure, network computer 300 includes a processor 302 that may be in communication with a memory 304 via a bus 328. In some embodiments, processor 302 may be comprised of one or more hardware processors or one or more processor cores. In some cases, one or more of the one or more processors may be specialized processors designed to perform one or more specialized actions, such as those described herein. Network computer 300 also includes a power supply 330, network interface 332, audio interface 356, display 350, keyboard 352, input/output interface 338, processor-readable stationary storage device 334, or processor-readable removable storage device 336. Power supply 330 provides power to network computer 300.

Network interface 332 includes circuitry for coupling network computer 300 to one or more networks and is constructed for use with one or more communication protocols and technologies including protocols and technologies that implement any portion of the Open Systems Interconnection model (OSI model), such as global system for mobile communication (GSM), code division multiple access (CDMA), time division multiple access (TDMA), user datagram protocol (UDP), transmission control protocol/Internet protocol (TCP/IP), Short Message Service (SMS), Multimedia Messaging Service (MMS), general packet radio service (GPRS), WAP, ultra wide band (UWB), IEEE 802.16 Worldwide Interoperability for Microwave Access (WiMax), Session Initiation Protocol/Real-time Transport Protocol (SIP/RTP), or any of a variety of other wired or wireless communication protocols. Network interface 332 is sometimes known as a transceiver, transceiving device, or network interface card (NIC). Network computer 300 may optionally communicate with a base station (not shown) or directly with another computer.

Audio interface 356 is arranged to produce and receive audio signals such as the sound of a human voice. For example, audio interface 356 may be coupled to a speaker and microphone (not shown) to enable telecommunication with others or generate an audio acknowledgement for some action. A microphone in audio interface 356 can also be used for input to or control of network computer 300, for example, using voice recognition.

Display 350 may be a liquid crystal display (LCD), gas plasma, electronic ink, light emitting diode (LED), Organic LED (OLED), or any other type of light reflective or light transmissive display that can be used with a computer. Display 350 may be a handheld projector or pico projector capable of projecting an image on a wall or another object.

Network computer 300 may also comprise input/output interface 338 for communicating with external devices or computers not shown in FIG. 3. Input/output interface 338 can utilize one or more wired or wireless communication technologies, such as USB™, Firewire™, Wi-Fi™ WiMax, Thunderbolt™, Infrared, Bluetooth™, Zigbee™, serial port, parallel port, or others.

Also, input/output interface 338 may also include one or more sensors for determining geolocation information (e.g., GPS), monitoring electrical power conditions (e.g., voltage sensors, current sensors, frequency sensors, and so on), monitoring weather (e.g., thermostats, barometers, anemometers, humidity detectors, precipitation scales, or others), or others. Sensors may be one or more hardware sensors that collect or measure data that is external to network computer 300. Human interface components can be physically separate from network computer 300, allowing for remote input or output to network computer 300. For example, information routed as described here through human interface components such as display 350 or keyboard 352 can instead be routed through the network interface 332 to appropriate human interface components located elsewhere on the network. Human interface components include any component that allows the computer to take input from, or send output to, a human user of a computer. Accordingly, pointing devices, such as mice, styluses, track balls, or others, may communicate through pointing device interface 358 to receive user input.

GPS receiver or transceiver 340 can determine the physical coordinates of network computer 300 on the surface of the Earth, which typically outputs a location as latitude and longitude values. GPS receiver or transceiver 340 can also employ other geo-positioning mechanisms, including triangulation, assisted GPS (AGPS), Enhanced Observed Time Difference (E-OTD), Cell Identifier (CI), Service Area Identifier (SAI), Enhanced Timing Advance (ETA), Base Station Subsystem (BSS), or others, to further determine the physical location of network computer 300 on the surface of the Earth. It is understood that under different conditions, GPS receiver or transceiver 340 can determine a physical location for network computer 300. In at least one embodiment, however, network computer 300 may, through other components, provide other information that may be employed to determine a physical location of the client computer, including, for example, a Media Access Control (MAC) address, IP address, or others.

In one or more of the various embodiments, one or more applications (for example, one or more operating systems 306, resource classification engines 318, resource recipe generation engines 322, consumption control engines 324, metrics analysis engines 326, dashboards, or others) may be arranged to employ geo-location information to select one or more localization features, such as one or more time zones, languages, currencies, calendar formatting, geographical regions or territories, or others. In some of the various embodiments, localization features may be used in one or more portions of file system object meta-data, file system objects, file systems, user-interfaces, reports, internal processes, databases, or others. In some embodiments, geo-location information used for selecting localization information may be provided by GPS receiver or transceiver 340. Also, in some embodiments, geo-location information may include information provided using one or more geo-location protocols over one or more networks, such as wireless network 108, network 110, or others.

Memory 304 may include Random Access Memory (RAM), Read-Only Memory (ROM), or other types of memory. Memory 304 illustrates an example of computer-readable storage media (devices) for storage of information such as computer-readable instructions, data structures, program modules or other data. Memory 304 stores a basic input/output system (BIOS) 308 for controlling low-level operation of network computer 300. The memory also stores an operating system 306 for controlling the operation of network computer 300. It will be appreciated that this component may include a general-purpose operating system such as a version of UNIX or LINUX™ or a specialized operating system such as Microsoft Corporation's Windows® operating system or the Apple Corporation's IOS® operating system. The operating system may include or interface with a Java virtual machine module that enables control of hardware components or operating system operations via Java application programs. Likewise, other runtime environments may be included.

Memory 304 may further include one or more data storage 310, which can be utilized by network computer 300 to store, among other things, applications 320 or other data. For example, data storage 310 may also be employed to store information that describes various capabilities of network computer 300. The information may then be provided to another device or computer based on any of a variety of methods, including being sent as part of a header during a communication, sent upon request, or others. Data storage 310 may also be employed to store social networking information including address books, buddy lists, aliases, user profile information, or others. Data storage 310 may further include program code, data, algorithms, or others, for use by a processor, such as processor 302 to execute and perform actions such as those actions described below. In some embodiments, at least some of data storage 310 might also be stored on another component of network computer 300, including non-transitory media inside processor-readable removable storage device 336, processor-readable stationary storage device 334, or any other computer-readable storage device within network computer 300 or even external to network computer 300. Data storage 310 may include, for example, demographics information 312, resource information 314, metrics information 316, or others. Demographics information 312 may include information indicative of characteristics, historical resource consumption, historical performance, or others associated with one or more geographical regions, control sessions, agents, entities associated with one or more agents, populations of agents, groups within the one or more populations of agents, or others. Resource information 314 may include information indicative of characteristics associated with one or more resources, recipes of combinations of resources, or others that may be employed during one or more consumption control sessions. Metrics information 316 may include one or more values of one or more metrics associated with one or more active control sessions, completed control sessions, performance monitors, control session users or agents, or others.

Applications 320 may include computer executable instructions which, when executed by network computer 300, transmit, receive, or otherwise process messages (e.g., SMS, Multimedia Messaging Service (MMS), Instant Message (IM), email, or other messages), audio, video, and enable telecommunication with another user of another mobile computer. Other examples of application programs include calendars, search programs, email client applications, IM applications, SMS applications, Voice Over Internet Protocol (VOIP) applications, contact managers, task managers, transcoders, database programs, word processing programs, security applications, spreadsheet programs, games, search programs, databases, web services, and so forth. Applications 320 may include resource classification engine 318, resource recipe generation engine 322, consumption control engine 324, metrics analysis engine 326, or others that perform actions further described below. In one or more of the various embodiments, one or more applications 220 or 320 (for example, one or more performance tracking engines 218, performance monitor engines 222, other client applications 224, web browser 226, resource classification engines 318, resource recipe generation engines 322, consumption control engines 324, metrics analysis engines 326, or others) may be separate and discrete from one or more other applications 220 or 320. In some of the various embodiments, one or more applications 220 or 320 may include one or more portions of one or more other applications 220 or 320 (for example, one or more portions of the one or more other applications 220 or 320 may include one or more processes, programming concepts, or others within the one or more applications 220 or 320). In some embodiments, one or more of the applications may be implemented as modules or components of another application. Further, in some embodiments, applications may be implemented as operating system extensions, modules, plugins, or others.

Furthermore, in some of the various embodiments, resource classification engine 318, resource recipe generation engine 322, consumption control engine 324, or metrics analysis engine 326 may be operative in a cloud-based computing environment. In some of the various embodiments, these engines, or others, that comprise the control platform or control system may be executing within virtual machines or virtual servers that may be managed in a cloud-based based computing environment. In some of the various embodiments, in this context the applications may flow from one physical network computer within the cloud-based environment to another depending on performance and scaling considerations automatically managed by the cloud computing environment. Likewise, in some of the various embodiments, virtual machines or virtual servers dedicated to resource classification engine 318, resource recipe generation engine 322, consumption control engine 324, or metrics analysis engine 326 may be provisioned and de-commissioned automatically. Also, in some of the various embodiments, resource classification engine 318, resource recipe generation engine 322, consumption control engine 324, metrics analysis engine 326, or others may be located in virtual servers running in a cloud-based computing environment rather than being tied to one or more specific physical network computers. In some embodiments, one or more of resource classification engine 318, resource recipe generation engine 322, consumption control engine 324, metrics analysis engine 326, or others may individually or cooperatively perform one or more portions of one or more of the actions described herein, such as one or more actions associated with one or more blocks in one or more of the processes described herein. In some embodiments, one or more of the named engines have sub-engines (not shown) that individually or cooperatively perform one or more of the one or more actions. In some embodiments, one or more of the named engines are included as part of another one or more of the named engines.

Further, network computer 300 may also comprise hardware security module (HSM) 360 for providing additional tamper resistant safeguards for generating, storing or using security/cryptographic information, such as keys, digital certificates, passwords, passphrases, two-factor authentication information, or others. In some embodiments, hardware security module may be employed to support one or more standard public key infrastructures (PKI) and may be employed to generate, manage, or store keys pairs, or others. In some embodiments, HSM 360 may be a stand-alone network computer, in other cases, HSM 360 may be arranged as a hardware card that may be installed in a network computer.

Additionally, in one or more embodiments (not shown in the figures), network computer 300 may include one or more embedded logic hardware devices instead of one or more CPUs, such as an Application Specific Integrated Circuits (ASICs), Field Programmable Gate Arrays (FPGAs), Programmable Array Logics (PALs), or others. The one or more embedded logic hardware devices may directly execute embedded logic to perform actions. Also, in one or more embodiments (not shown in the figures), network computer 300 may include one or more hardware microcontrollers instead of one or more CPUs. In some embodiments, the one or more microcontrollers may directly execute their own embedded logic to perform actions and access its own internal memory and its own external Input and Output Interfaces (e.g., hardware pins or wireless transceivers) to perform actions as a System On a Chip (SOC) or others.

Illustrative Logical System Architecture

Figure 4:
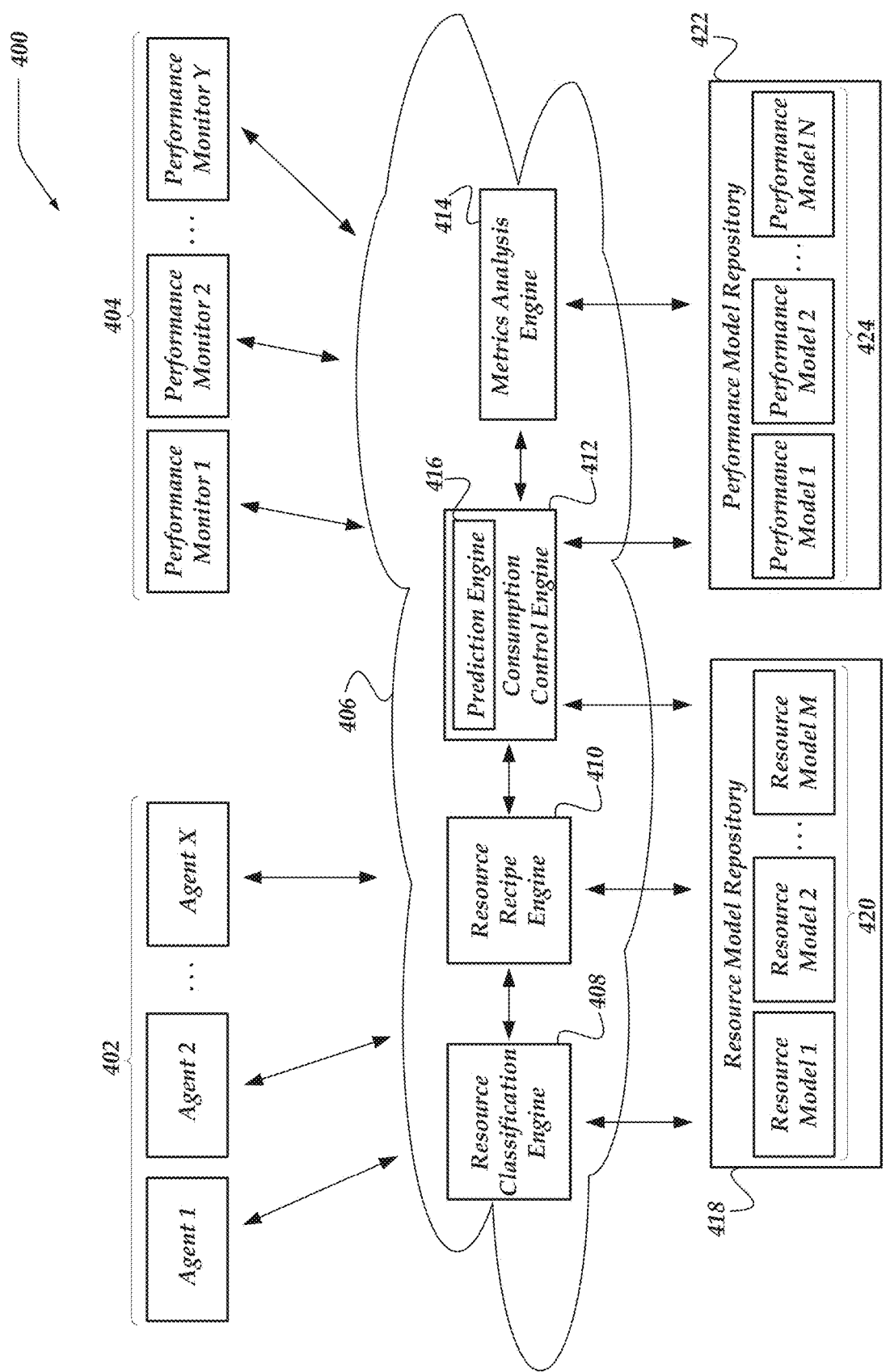
FIG. 4 shows a logical architecture of an example system for controlling resource consumption.

FIG. 4 shows a logical architecture of example resource consumption control system 400 for controlling resource consumption. System 400 may be arranged to include one or more consuming agents or performance monitors, such as agents 402 or performance monitors 404. Each of the one or more agents or performance monitors may include, or be associated with, one or more client computers, such as client computer 200 (for example, one or more of client computers 102-105 or others). System 400 may also be arranged to include one or more resource consumption control computers, such as resource consumption control computer 406 (represented in the example shown in FIG. 4 as a cloud-computing environment). Each of the one or more resource consumption control computers may include a network computer, such as network computer 300 (for example, application server computer 116, application server computer 117, resource consumption control computer 118, or others). Resource consumption control computer 406 may include one or more engines, such as resource classification engine 408 (e.g., resource classification engine 318 or others), resource recipe engine 410 (e.g., resource recipe generation engine 322 or others), consumption control engine 412 (e.g., consumption control engine 324 or others), metrics analysis engine 414 (e.g., metrics analysis engine 326 or others), prediction engine 416, or others. In some embodiments, one or more prediction engines 416 may be part of or otherwise associated with consumption control engine 412.

One or more of the engines in resource consumption control computer 406 may communicate with one or more resource model repositories, such as resource model repository 418. Each resource model repository may include one or more resource models, such as resource models 420. Each of the one or more resource models may be associated with a resource that was, is, or is predicted to be available for consumption. One or more of the engines in resource consumption control computer 406 may communicate with one or more performance model repositories, such as performance model repository 422. Each performance model repository may include one or more performance models, such as performance models 424. Each of the one or more performance models may be associated one or more agent characteristics or conditions and may be employed to predict agent performance for one or more agents associated with the one or more agent characteristics or conditions. In some embodiments, system 400 may facilitate comparing performance feedback from one or more agents 402 with one or more outputs of one or more performance models 424 to calibrate resource consumption control system 400 and improve performance criterion.

In one or more of the various embodiments, an agent may provide a request for a control session to resource consumption control computer 406. In other embodiments, a supervisory or peer entity (for example, a master controller, coach, teammate, team manager, or others) may provide the request on behalf of the agent. In some of the various embodiments, the request may include control session initialization information, such as one or more of the following: identification information of the agent; identification information of an entity that employs or hosts the agent (for example, an assembly line, vehicle, school, sports club, or others), associated agents (for example, peers, teammates, or others), or associated control sessions; contact information of the agent; characteristic information associated with the agent; preferred date or time information for launching or concluding the control session; or others. In some embodiments, the agent may enter the control session initialization information in one or more fields in a user interface provided by a web page, application, or others. In some embodiments, the user interface may be arranged to provide the entered control session initialization information to resource consumption control computer 406 based on one or more actions of the agent, such as selecting a submit button on the web page or application.

In one or more of the various embodiments, resource consumption control computer 406 may assign one or more performance monitors to the requested control session arbitrarily or based on the initialization information, such as one or more portions of the initialization information, demographics information (e.g., census information, information obtained in prior or concurrent control sessions, or others), or others. For example, each performance monitor may be associated with a logical territory (e.g., type of activity associated with the requested control sessions, type of entities, type of campaign agents, control session objectives, or others), geographical territory (e.g., postal codes or others), or others and may be assigned control sessions for entities or agents associated with the performance monitor's logical or geographic territory. In some of the various embodiments, the one or more assigned performance monitors may take one or more actions on behalf of the agent, such as providing one or more portions of the request, providing one or more portions of the initialization information, associating the agent with one or more other agents, associating the agent with the entity, or others.

In one or more of the various embodiments, resource consumption control computer 406 may obtain additional initialization information based on the agent-provided information, such as demographics information associated with the entity, demographics information associated with a geographic region around the entity, or others. In some of the various embodiments, resource consumption control computer 406 may contact the agent or entity to obtain additional control session initialization information. In other embodiments, the user interface may be arranged to collect each portion of the initialization information to facilitate starting initialization of a control session directly from the user interface.

In one or more of the various embodiments, initialization information may include agent characteristics associated with the agent. In some of the various embodiments, the agent characteristics may include values for various parameters associated with the agent, such as agent type (for example, internal combustion engine, Stirling engine, male, female, or others), age, size (for example, displacement, number of cylinders, height, or others), weight, material makeup (for example, quantities or percentages of one or more elements, such as aluminum, iron, body fat, or others), activity rating (for example, a value selected on a predetermined scale such as between 0 and 10, 0 and 1, 1 and 2, or others that indicates an amount of use above rest per predetermined period, such as a duration or intensity of the use, or others), lifestyle rating (for example, a value selected on a predetermined scale such as between 0 and 10, 0 and 1, 1 and 2, or others that indicates how physically active the agent is during the agent's time outside of the activities measured by the activity rating, such as the agent's professional time and non-training leisure time or others), impairment status (for example, one or more values that indicate whether the agent is damaged or injured, the seriousness of the damage or injury, or others), objectives (for example, performance improvement, performance maintenance, weight loss, weight gain, weight maintenance, growth, development, or others), resource intake frequency (for example, an average number of times per day or other predetermined period that a fuel tank is refilled, the number of meals or snacks per day, or others), resource intake type (for example, standard complete tank refill, pre-activity complete tank refill, post-activity complete tank refill, standard partial tank refill, pre-activity partial tank refill, post-activity partial tank refill standard meal, pre-workout meal, post-workout meal, standard snack, pre-workout snack, post-workout snack, or others), or others. In some embodiments, one or more portions of the agent characteristics information may be obtained from or generated by one or more sensors or sensor interfaces (for example, one or more cameras 240, video interfaces 242, sensor interfaces 262, or others) associated with the agent (for example, one or more sensors or sensor interfaces that are included in client computer 200, that are in communication with client computer 200, or others). In some embodiments, one or more portions of the agent characteristics information (for example, one or more unknown or estimated portions of the agent characteristics information, such as weight, material makeup, activity rating, lifestyle rating, or others) may be accumulated over a predetermined period prior to launching a control session. In some embodiments, resource consumption control computer 406 may generate one or more agent data objects associated with the agent based on the agent characteristics information, such as one or more tables having records and attributes with associated fields that contain values that define, represent, or include one or more portions of the agent characteristics information.

In one or more of the various embodiments, resource consumption control computer 406 may evaluate one or more conditions of one or more candidate performance models based on one or more portions of the agent characteristics information included in the one or more agent data objects associated with the agent. In some of the various embodiments, each candidate performance model may be associated with one or more agent characteristics or conditions, such as one or more ranges, thresholds, or others for one or more parameters associated with agent characteristics. In some embodiments, resource consumption control computer 406 may compare one or more values of one or more parameters in the agent characteristics information to one or more condition values. In some embodiments, if the one or more evaluated conditions and portions of the agent characteristics information fail to match (for example, the one or more parameter values failing to fall within an acceptable range defined by the one or more condition values), another one or more candidate performance models may be evaluated. In some embodiments, if the one or more evaluated conditions and portions of the agent characteristics information match, the one or more candidate performance models may be selected.

In one or more of the various embodiments, one or more consumption control engines 412, prediction engines 416, or others may traverse the one or more selected performance models to generate a predicted energy consumption needs amount for the agent based on one or more portions of the agent characteristics information. In some of the various embodiments, one or more consumption control engines 412, prediction engines 416, or others may execute one or more portions of the one or more selected performance models or one or more sub-models within the one or more selected performance models to generate one or more predicted values (for example, one or more predicted baseline energy expenditure rates, predicted interval energy expenditure amounts, or others) based on one or more portions of the agent characteristics information. In some embodiments, the one or more consumption control engines 412, prediction engines 416, or others may input one or more portions of the predicted values into one or more other portions of the one or more selected performance models or one or more other sub-models within the one or more selected performance models to generate one or more other predicted values (for example, another one or more predicted baseline energy expenditure rates, predicted interval energy expenditure amounts, or others). In some embodiments, each output may be employed as an input to generate another output, and this process may iteratively continue, until the one or more selected performance models generate the predicted energy consumption needs for the agent.

In one or more of the various embodiments, one or more consumption control engines 412, prediction engines 416, or others may execute one or more portions of the one or more selected performance models or one or more sub-models within the one or more selected performance models to generate a predicted baseline energy expenditure rate based on one or more portions of the agent characteristics information. In some of the various embodiments, the predicted baseline energy expenditure rate may represent or include an amount of energy that the agent is predicted to use over a predetermined period of time at rest (for example, basal metabolic rate (BMR) or others), such as Joules per minute that the agent uses at idle, calories that the agent uses daily at rest, or others. In some embodiments, the one or more model portions or sub-models employed to generate the predicted baseline energy expenditure rate may be selected based on one or more portions of the agent characteristics information, such as agent type (for example, internal combustion engine, Stirling engine, male gender, female gender, or others), weight, known material makeup (for example, quantities or percentages of one or more elements, such as aluminum, iron, body fat, or others), age, size (for example, displacement, number of cylinders, height, or others), estimated material makeup, activity rating (for example, a value selected on a predetermined scale such as between 0 and 1 that indicates an amount of use above rest per predetermined period, such as a duration or intensity of the use, or others), or others. In other embodiments, the one or more selected-model portions or sub-models may be selected arbitrarily or may be selected for all agents. In some embodiments, one or more portions of agent characteristics information employed to select the one or more selected-model portions or sub-models may also be input into the one or more selected portions or sub-models to generate the predicted baseline energy expenditure rate.

In one or more of the various embodiments, one or more consumption control engines 412, prediction engines 416, or others may execute one or more portions of the one or more selected performance models or one or more sub-models within the one or more selected performance models to generate a predicted interval energy expenditure amount based on the predicted baseline energy expenditure rate and one or more portions of the agent characteristics information. In some of the various embodiments, the predicted interval energy expenditure amount may represent or include an amount of energy that the agent is predicted to use over a predetermined interval when engaging in the typical activities and lifestyle of the agent (for example, an average amount of energy that the agent is predicted to use per interval), such as Joules that the agent uses per hour in a typical week (or average Joules that the agent uses per week), calories that the agent uses per day in a typical day (or average calories that the agent uses per day), or others). In some embodiments, the predicted interval energy expenditure amount may include an adjustment to the predicted baseline energy expenditure rate based on one or more portions of the agent characteristics information, such as activity rating (for example, a value selected on a predetermined scale such as a value between zero and one that indicates an amount of use above rest per predetermined period, such as a duration or intensity of the use, or others), lifestyle rating (for example, a value selected on a predetermined scale such as between 0 and 1 that indicates how physically active the agent is during the agent's time outside of the activities measured by the activity rating, such as the agent's professional time and non-training leisure time or others), impairment status (for example, one or more values that indicate whether the agent is damaged or injured, the seriousness of the damage or injury, or others), or others. In some embodiments, the one or more portions or sub-models employed to generate the predicted interval energy expenditure amount may be selected based on one or more portions of the agent characteristics information, such as agent type (for example, internal combustion engine, Stirling engine, male gender, female gender, or others), age, or others. In other embodiments, the one or more selected-model portions or sub-models may be selected arbitrarily or may be selected for all agents. In some embodiments, one or more portions of agent characteristics information employed to select the one or more selected-model portions or sub-models may also be input into the one or more selected portions or sub-models to generate the predicted interval energy expenditure amount.

In one or more of the various embodiments, one or more consumption control engines 412, prediction engines 416, or others may execute one or more portions of the one or more selected performance models or one or more sub-models within the one or more selected performance models to generate a predicted energy consumption needs amount based on the predicted interval energy expenditure and one or more portions of the agent characteristics information. In some of the various embodiments, the predicted energy consumption needs amount may represent or include an amount of energy that, if consumed by the agent when engaged in the typical activities and lifestyle of the agent, is predicted to result in the agent achieving one or more of the agent's objectives (for example, performance improvement, performance maintenance, weight loss, weight gain, weight maintenance, growth, development, or others). In some embodiments, the one or more model portions or sub-models employed to generate the predicted energy consumption needs amount may be selected based on one or more portions of the agent characteristics information, such as one or more agent objectives (for example, rate or amount of performance improvement, performance maintenance, rate or amount of weight loss, rate or amount of weight gain, weight maintenance, rate or amount of growth, rate or amount of development, or others), activity rating (for example, a value selected on a predetermined scale such as a value between 0 and 1 that indicates an amount of use above rest per predetermined period, such as a duration or intensity of the use, or others), or others. In some embodiments, one or more portions of agent characteristics information employed to select the one or more selected-model portions or sub-models may also be input into the one or more selected portions or sub-models to generate the predicted energy consumption needs amount.

In one or more of the various embodiments, the one or more selected-model portions or sub-models may have associated output thresholds that limit the maximum value or minimum value of the predicted energy consumption needs amount based on the predicted baseline energy expenditure rate, the predicted interval energy expenditure amount, one or more portions of the agent characteristics information (for example, activity rating, impairment status, or others) to, for example, prevent the agent from incurring damage based on consumption of insufficient or excessive amounts of resources. In other embodiments, one or more warnings may be provided to the agent or a graphical user interface based on the value of the predicted energy consumption needs amount being above or below the one or more output thresholds to, for example, provide an alert that indicates an elevated risk that the agent may incur damage based on consumption of insufficient or excessive amounts of resources. For example, a lower threshold for the predicted energy consumption needs amount may include the predicted baseline energy expenditure rate, the predicted interval energy expenditure amount if the agent has an impairment (for example, performance-impeding damage, injury, illness, or others), a predetermined amount of energy (for example, 5 kilojoules (kJ), 1,200 calories, or others), or others. As another example, an upper threshold for the predicted energy consumption needs amount may include a predetermined amount of energy (for example, 4 kJ, 1,000 calories, or others) over the predicted interval energy expenditure amount, a predetermined amount of energy (for example, 2 kJ, 500 calories, or others) over the predicted interval energy expenditure amount if the agent's activity rating is less than a predetermined threshold, or others.

In one or more of the various embodiments, one or more consumption control engines 412, prediction engines 416, or others may execute one or more portions of the one or more selected performance models or one or more sub-models within the one or more selected performance models to transform the predicted energy consumption needs amount into resource distribution information. In some of the various embodiments, the transformation may include transforming the predicted energy consumption needs amount into specific-units needs amounts for multiple resource types, transforming the specific-units needs amounts into normalized-units needs amounts for the multiple resource types, and transforming the normalized-units needs amounts into resource distribution information. In some embodiments, specific-units needs amounts may include amounts that are specified in units that are specific to particular resources, such as ounces, gallons, grams, or others. In some embodiments, normalized-units needs amounts may include amounts that are specified in units that are generic across all resources, such as servings or others (for example, one serving of protein may be described as corresponding to the volume of two standard 52-card decks of playing cards or others). In some embodiments, specific-units needs amounts may not be converted directly into normalized-units needs because a normalized-unit of one resource may include one or more portions of a normalized-unit of another one or more other resources (for example, a serving of gasoline may include one or more fuel additives, a serving of fat may include protein, or others). Accordingly, in some embodiments, specific-units needs amounts for one or more resource types may be transformed into normalized-units needs amounts for the one or more resource types based on specific-units needs amounts for the one or more resource types and normalized-units needs amounts for one or more other resource types.

In one or more of the various embodiments, one or more consumption control engines 412, prediction engines 416, or others may execute one or more portions of the one or more selected performance models or one or more sub-models within the one or more selected performance models to generate specific-units needs amounts for multiple resource types (for example, one or more gasolines, fuel stabilizers, oil additives, proteins, carbohydrates, fats, vegetables, or others) based on the predicted energy consumption needs amount and one or more portions of the agent characteristics information. In some of the various embodiments, the specific-units needs amounts for the multiple resource types may be independently or discretely generated for each interval (for example, another set of specific-units needs amounts for the multiple resource types may be generated for each interval or others). In other embodiments, the specific-units needs amounts for the multiple resource types may be employed for each interval in one or more periods (for example, a set of specific-units needs amounts for the multiple resource types may be generated for each period, with each interval in the period being assigned the same specific-units needs amounts for the multiple resource types, or others). In some embodiments, the one or more portions or sub-models employed to generate the specific-units needs amounts may be selected based on one or more portions of the agent characteristics information, such as agent age, material makeup (for example, known or estimated quantities or percentages of one or more elements, such as aluminum, iron, body fat, or others), activity rating (for example, a value selected on a predetermined scale such as a value between zero and one that indicates an amount of use above rest per predetermined period, such as a duration or intensity of the use, or others), impairment status (for example, one or more values that indicate whether the agent is damaged or injured, the seriousness of the damage or injury, or others), objectives (for example, performance improvement, performance maintenance, weight loss, weight gain, weight maintenance, growth, development, or others), or others. In other embodiments, the one or more selected-model portions or sub-models may be selected arbitrarily or may be selected for all agents. In some embodiments, one or more portions of agent characteristics information employed to select the one or more selected-model portions or sub-models may also be input into the one or more selected portions or sub-models to generate the predicted baseline energy expenditure rate. In some embodiments, one or more specific-units needs amounts may be overridden by one or more other components in system 400, such as agent 402, performance monitor 404, or others.

In one or more of the various embodiments, one or more consumption control engines 412, prediction engines 416, or others may execute one or more portions of the one or more selected performance models or one or more sub-models within the one or more selected performance models to generate normalized-units needs amounts for each of the multiple resource types (for example, one or more gasolines, fuel stabilizers, oil additives, proteins, carbohydrates, fats, vegetables, or others) based on the respective specific-units needs amounts for the multiple resource types and the normalized-units needs amounts for one or more other resource types. In some of the various embodiments, a temporary normalized-units needs amount for one or more resource types may be generated based on one or more portions of the agent characteristics information, the predicted interval energy expenditure, the predicted energy consumption needs amount, or others. In some embodiments, a predicted normalized-units needs amount for one or more resource types may be generated based on the temporary normalized-units needs amount for one or more other resource types, one or more portions of the agent characteristics information, the predicted interval energy expenditure, the predicted energy consumption needs amount, or others. In other embodiments, the normalized-units needs amount for one or more first resource types (for example, vegetables or others) may be generated based on one or more portions of the agent characteristics information (for example, activity rating or others), the predicted interval energy expenditure, the predicted energy consumption needs amount, or others. In some embodiments, the normalized-units needs amount for one or more additional resource types may be generated based on one or more portions of the agent characteristics information (for example, age, weight, material makeup, impairment status, amount of objective weight loss or gain per predetermined period, or others), the normalized-units needs amount for the one or more first resource types, the normalized-units needs amounts for one or more other additional resource types, the predicted energy consumption needs amount, or others. In some embodiments, the normalized-units needs amounts for the multiple resource types may be independently or discretely generated for each interval (for example, another set of normalized-units needs amounts for the multiple resource types may be generated for each interval or others). In other embodiments, the normalized-units needs amounts for the multiple resource types may be employed for each interval in one or more periods (for example, a set of normalized-units needs amounts for the multiple resource types may be generated for each period, with each interval in the period being assigned the same normalized-units needs amounts for the multiple resource types, or others).

In one or more of the various embodiments, the predicted interval energy expenditure may be compared to the predicted energy consumption needs amount, and the one or more model portions or sub-models used to generate the normalized-units needs for the one or more first resource types may be selected based on the comparison and one or more portions of the agent characteristics information (for example, activity rating). In other embodiments, the normalized-units needs amounts for each resource type may be generated independent of the normalized-units needs amounts for each other resource type. In some of the various embodiments, the one or more model portions or sub-models used to generate the normalized-units needs for the one or more additional resource types may be selected based on one or more portions of the agent characteristics information (for example, age, weight, material makeup, impairment status, objectives, or others). In other embodiments, the one or more selected-model portions or sub-models employed to generate the normalized-units needs amounts for the one or more first or additional resource types may be selected arbitrarily or may be selected for all agents. In some embodiments, one or more portions of agent characteristics information employed to select the one or more selected-model portions or sub-models may also be input into the one or more selected portions or sub-models to generate the normalized-units needs amounts for the one or more first or additional resource types.

In one or more of the various embodiments, one or more consumption control engines 412, prediction engines 416, or others may execute one or more portions of the one or more selected performance models or one or more sub-models within the one or more selected performance models to generate resource distribution information based on the normalized-units needs amounts for the multiple resource types, one or more portions of the agent characteristics information, or others. In some of the various embodiments, one or more portions of the agent characteristics information used to generate the resource distribution information may include weight, resource intake frequency (for example, an average number of times per day or other predetermined period that a fuel tank is refilled, the number of meals or snacks per day, or others), resource intake type (for example, standard complete tank refill, pre-activity complete tank refill, post-activity complete tank refill, standard partial tank refill, pre-activity partial tank refill, post-activity partial tank refill standard meal, pre-workout meal, post-workout meal, standard snack, pre-workout snack, post-workout snack, or others), or others. In some embodiments, the resource distribution information may represent or include the normalized-units amounts for the multiple resources that the agent should intake during each resource intake. In some embodiments, the normalized-units needs amounts for each resource type may be evenly distributed among the expected number of resource intakes per predetermined duration (for example, the resource intake frequency may represent or include an expected number of resource intakes for each resource intake type per day or another predetermined time range). For example, the normalized-units needs amount for protein may be divided by the expected number of meals per day to generate a distributed normalized-units meals needs amount for protein.

In other embodiments, the normalized-units needs amounts for each resource type may be distributed more heavily among the expected number of resource intakes of one or more resource intake types (for example, standard complete tank refills, pre-activity complete tank refills, standard meals, pre-workout meals, or others) than the expected number of resource intakes of another one or more resource intake types (for example, standard partial rank refills, pre-activity partial tank refills, standard snacks, pre-workout snacks, or others). For example, the normalized-units needs amount for protein may be weighted (for example, multiplied by 0.75 or others) and may be divided by the expected number of meals per day to generate the distributed normalized-units meals needs amount for protein, and the normalized-units needs amount for protein may be less heavily weighted (for example, multiplied by 0.25 or others) and may be divided by the expected number of snacks per day to generate a distributed normalized-units snacks needs amount for protein. In some embodiments, the resource distribution information may additionally or alternatively represent or include the specific-units needs distributed among the expected number of resource intakes. In some embodiments, the resource intake frequency or resource intake type may have predetermined default values or may be set by the agent, the performance monitor, or others. In some embodiments, the one or more model portions or sub-models used to generate the resource distribution information may be selected based on one or more portions of the agent characteristics information (for example, resource intake frequency, resource intake type, or others). In other embodiments, the one or more selected-model portions or sub-models employed to generate the normalized-units needs amounts for the one or more first or additional resource types may be selected arbitrarily or may be selected for all agents. In some embodiments, one or more portions of agent characteristics information employed to select the one or more selected-model portions or sub-models may also be input into the one or more selected portions or sub-models to generate the resource distribution information.

In one or more of the various embodiments, one or more resource consumption control engines 412 may provide resource consumption control instructions to the agent based on the resource distribution information. In some of the various embodiments, the resource consumption control instructions may be provided to the agent in bulk, such as multiple instructions associated with multiple intakes being provided at once. In other embodiments, the resource consumption control instructions may be provided to the agent for each intake (for example, at a time corresponding to another time at which an intake is expected to occur, such as a predetermined amount of time before an event or action that is expected to provide a sufficient duration to process the instructions and take action in accordance with the instructions such as intake resources a predetermined amount of time before the event or action, a predetermined amount of time after an event or action that is expected to provide a sufficient duration to process and take action in accordance with the instruction such as intake resources a predetermined amount of time after the event or action terminates, or others). In some embodiments, the resource consumption control instructions may be pushed to the agent. In other embodiments, the agent may pull the resource consumption control instructions from one or more resource consumption control engines 412. In some embodiments, the resource consumption control instructions may represent or include the resource distribution information associated with each intake, presented in one or more of specific units, normalized units, or others.

In one or more of the various embodiments, one or more network computers, such as one or more network computers 300 (for example, one or more resource consumption control computers 406, consumption control engines 324, consumption control engines 412, or others), may control one or more agents 402 based on the one or more resource consumption instructions. In some of the various embodiments, controlling one or more agents 402 may include providing the resource consumption instructions, thereby facilitating causing one or more client computers, such as one or more client computers 200 (for example, one or more client computers 102-105 or others), associated with or included in one or more agents 402 to perform one or more actions in accordance with the one or more resource consumption instructions, such as one or more of the following: causing one or more agents 402 or one or more components of one or more agents 402 to intake or consume one or more resources, amounts of resources, resource recipes, resource types, or others; causing one or more projectors 246, displays 250, audio interfaces 256, haptic interfaces 264, or others to provide one or more outputs (for example, displays, audio notifications, haptic notifications, or others) of one or more instructions, recommendations, interface components, alerts, or others (for example, when one or more applications 220 are next launched, downloaded, opened, or otherwise engaged, when the one or more resource instructions are obtained by client computer 200, or others); or others. In some embodiments, the one or more network computers may control one or more agents 402 by providing one or more resource consumption control instructions that include values or recipe amounts presented in normalized units, thereby facilitating reducing likelihood that the amount of agent consumption diverges from the predicted energy consumption needs amounts, at least in comparison to providing instructions that include values or recipe amounts presented only in specific units.

In one or more of the various embodiments, one or more consumption control engines 412, metrics analysis engines 414, or others may obtain metrics associated with the control session for the agent. In some embodiments, the metrics may represent or include resource consumption information (for example, amounts of resource types consumed in specific units, normalized units, or others), objective performance information (for example, rating indication of how well the agent performed one or more activities, how the agent felt during or after one or more activities, weight of the agent, or others), or others. In some embodiments, one or more client computers 200 may monitor one or more actions or provide one or more of the metrics based on inputs in one or more user interface components of a user interface of the agent. In some embodiments, one or more portions of the metrics may be obtained from or generated by one or more sensors or sensor interfaces (for example, one or more cameras 240, video interfaces 242, sensor interfaces 262, or others) associated with the agent (for example, one or more sensors or sensor interfaces that are included in client computer 200, that are in communication with client computer 200, or others). In some embodiments, the metrics may be obtained for multiple qualifying periods, such as two or more back-to-back qualifying periods or others. In some embodiments, a qualifying period may be defined as a set of a predetermined number of back-to-back intervals (for example, 4-7 back-to-back days or others) in which the number of complete intervals meets or exceeds a minimum threshold (for example, four or more complete intervals or others). In some embodiments, a complete interval may be defined as an interval for which resource consumption information has been obtained for each intake during the interval (for example, discretely, in total, or others) and for which objective performance information has been obtained for the interval. In some embodiments, a qualifying period may include one or more incomplete intervals (for example, an interval for which resource consumption information has not been obtained for one or more intakes during the interval or for which objective performance information has not been obtained for the interval) between two complete intervals in the qualifying period.

In one or more of the various embodiments, the resource consumption information may include reported amounts of specific units, normalized units, or others for each consumed resource type. In some of the various embodiments, the one or more network computers may permit the obtained metrics to include combinations of specific units, normalized units, or others based on whichever is more convenient for the agent to selectively shift the transformation process to the one or more network computers, thereby facilitating increasing the likelihood that or frequency at which the agent records resource consumption information (for example, decreasing the processing expense or time required for the agent to record resource consumption information and, thus, increasing the recording rate of the agent), which may increase the number of data points available for analysis and, thus, may increase accuracy of model outputs, information provided to performance monitors, instructions provided to agents, or others. In some embodiments, the reported amounts of specific or normalized units for each consumed resource type may indicate the reported amounts of specific or normalized units for each consumed resource type over the entirety of the complete intervals in the qualifying periods, over the entirety of the complete intervals in each qualifying period, over each complete interval, over each intake session in each complete interval, or others. In some embodiments, interval average amounts of specific or normalized units for each consumed resource type may be generated based on the reported amounts of specific or normalized units for each consumed resource type and the number of complete intervals. For example, the reported amounts of specific or normalized units for each consumed resource type over the entirety of the complete intervals in the qualifying periods may be divided by the total number of complete intervals in the qualifying periods to generate the reported average interval amounts of specific or normalized units for each consumed resource type.

In one or more of the various embodiments, one or more metrics analysis engines 414 may execute one or more models to transform the resource consumption information into total reported interval average amounts of normalized units for each consumed resource type based on the specific-units needs amounts for each consumed resource type and the normalized-units needs amounts for each consumed resource type. In some of the various embodiments, the reported interval average amounts of specific units for a consumed resource type may be divided by a ratio of the specific-units needs amount for the consumed resource type to the normalized-units needs amount for the consumed resource type, and the result may be added to the reported interval average amounts of normalized units for the consumed resource type to generate the total reported interval average amounts of normalized units for the consumed resource type. In some embodiments, the ratio may be based on an average of the specific-units needs amounts for the consumed resource type for each interval in the period and an average of the normalized-units needs amounts for the consumed resource type for each interval in the period (for example, the ratio may represent a ratio of a per-interval average of the specific-units needs amounts for the period and a per-interval average of the normalized-units needs amounts for the period). In other embodiments, the reported interval amounts of normalized units for the consumed resource type may be obtained for each interval by employing the ratio based on the specific-units and normalized-units needs amounts for each interval and subsequently averaged to generate the total reported interval average amounts of normalized units for the consumed resource type. In some embodiments, the total reported interval average amounts of normalized units may be generated for each consumed resource type. In other embodiments, the reported interval average amounts of normalized units for each consumed resource type may be transformed into interval average amounts of specific units for each consumed resource type (for example, multiplying the reported interval average amounts of normalized units by conversion factors associated with the consumed resource types, such as an average number of grams per protein serving or others), and the reported interval average amounts of specific units for each consumed resource type may be summed with the transformed interval average amounts of specific units for the consumed resource type to generate the total reported interval average amounts of specific units for the consumed resource type.

In one or more of the various embodiments, one or more metrics analysis engines 414, prediction engines 416, or others may execute one or more models to generate an average amount of energy consumed by the agent per interval based on the total reported interval average amounts of normalized or specific units for the consumed resource types. In some of the various embodiments, the total reported interval average amounts of normalized units for a consumed resource type may be multiplied by a conversion factor associated with the consumed resource type (for example, the total number of reportedly consumed carbohydrate servings multiplied by the average number of grams per serving of carbohydrates or others), and the result may be summed with the number of specific units for the consumed resource type that are expected to be included in the total reported interval average amounts of normalized units for each other consumed resource type (for example, the number expected based on one or more resource models 420 in resource model repository 418, such as resource model 700), thereby facilitating generating total reported interval average amounts of specific units for the consumed resource type. In other embodiments, the reported interval average amounts of normalized units for a consumed resource type may be multiplied by a conversion factor associated with the consumed resource type (for example, the number of reportedly consumed carbohydrate servings multiplied by the average number of grams per serving of carbohydrates or others) and summed with the reported interval average amounts of specific units for the consumed resource type, and the result may be summed with the number of specific units for the consumed resource type that are expected to be included in the total reported interval average amounts of normalized units for each other consumed resource type, thereby facilitating generating total reported interval average amounts of specific units consumed for the consumed resource type. In some embodiments, the total reported interval average amounts of specific units may be generated for each consumed resource type. In some embodiments, the total reported interval average amounts of specific units for each of the consumed resource types may be multiplied by the expected amount of energy in each specific unit of the consumed resource type to generate the reported amount of energy for each of the consumed resource types, and the reported amounts of energy of the consumed resource types may be summed to provide a total average amount of reportedly consumed energy per interval. In some embodiments, the total average amount of reportedly consumed energy may be generated for the entirety of the complete intervals in the qualifying periods, for the entirety of the complete intervals in each qualifying period, for each complete interval, for each intake session in each complete interval, or others and may subsequently be transformed into the total reportedly consumed amount of energy per interval. In some embodiments, the average amount of reportedly consumed energy per interval may be divided by the predicted interval energy expenditure amount to obtain a consumption result, and, optionally, the comparison result may be multiplied by 100 to provide the consumption result as a percentage.

In one or more of the various embodiments, one or more metrics analysis engines 414, prediction engines 416, or others may execute one or more portions of the one or more selected performance models or one or more sub-models within the one or more selected performance models to generate an average expected objective performance per interval (for example, an average expected weight loss per day, an average expected weight gain per day, or others) based on the predicted interval energy expenditure, the average amount of reportedly consumed energy per interval or the consumption result, the number of complete intervals, or others. In some of the various embodiments, the predicted interval energy expenditure may be subtracted from the average amount of reportedly consumed energy per interval to generate an average energy divergence amount per interval. In other embodiments, the consumption result may be transformed back into the average amount of reportedly consumed energy per interval prior to generating the average energy divergence amount per interval. In some embodiments, the average energy divergence amount per interval may be transformed into an average expected objective performance per interval (as measured in the units employed for the objective performance information, such as pounds, kilograms, or others). For example, the average energy divergence amount per interval may be measured in calories, and the average energy divergence amount per interval may be divided by 7,700 to transform the average energy divergence amount per interval into the average expected objective performance per interval as measured in kilograms.

In one or more of the various embodiments, one or more metrics analysis engines 414, prediction engines 416, or others may execute one or more portions of the one or more selected performance models or one or more sub-models within the one or more selected performance models to generate a total expected objective performance based on the average expected objective performance per interval, the phase in each period at which each complete interval occurs, or others. In some of the various embodiments, an average complete interval may be generated for each qualifying period based on the phase in each qualifying period at which each complete interval occurs. For example, for a qualifying period of a week that employs intervals of days with the qualifying period starting on Monday, Monday may be interval one, Tuesday may be interval two, Wednesday may be interval three, Thursday may be interval four, Friday may be interval five, Saturday may be interval six, Sunday may be interval seven, and, with complete intervals of Monday, Wednesday, Thursday, and Sunday, the average complete interval may be 3.75 ((1+3+4+7)/4=3.75). In some embodiments, the number of intervals between the average complete interval of the most recent qualifying period and the average complete interval of the first qualifying period may be counted, including one of the first or most recent average complete interval. For example, when the most recent qualifying period is the week immediately following the first qualifying period and both the most recent and the first qualifying periods have average complete intervals of 3.75, the number of intervals between the average complete intervals may be 7. In some embodiments, the average expected objective performance per interval may be multiplied by the number of intervals between the average complete intervals to generate the total expected objective performance.

In one or more of the various embodiments, one or more metrics analysis engines 414, prediction engines 416, or others may execute one or more portions of the one or more selected performance models or one or more sub-models within the one or more selected performance models to generate a calibration amount based on the total expected objective performance, the objective performance information for each qualifying period, the number of intervals between the average complete intervals, or others. In some of the various embodiments, the objective performance information for each complete interval in each qualifying period may be averaged to generate an average objective performance for each qualifying period. For example, the sum of the weight of the agent at each complete interval in a qualifying period may be divided by the number of complete intervals in the qualifying period to generate the average objective performance for the qualifying period. In some embodiments, the average objective performance of the first qualifying period may be subtracted from the average objective performance of the most recent qualifying period to generate an objective performance change. In some embodiments, the total expected objective performance may be subtracted from the objective performance change to generate an objective performance divergence. In some embodiments, the objective performance divergence may be divided by the number of intervals between the average complete intervals to generate an average objective performance divergence per interval. In some embodiments, the average objective performance divergence per interval may be transformed into the calibration amount (as measured in the units employed for the predicted interval energy expenditure amount, such as calories or others). For example, the average objective performance divergence per interval may be measured in kilograms, and the average objective performance divergence per interval may be divided by 7,700 to generate the calibration amount as measured in calories.

In one or more of the various embodiments, one or more consumption control engines 412, metrics analysis engines 414, prediction engines 416, or others may generate modified resource consumption instructions based on the calibration amount, the predicted interval energy expenditure amount, the agent characteristics information, or others. In some of the various embodiments, the calibration amount may be summed with one or more previous calibration amounts for the agent (for example, up to a predetermined number of previous calibration amounts that may have been generated employing one or more similar processes as described with regard to the calibration amount based on qualifying periods that may be prior to the most recent qualifying period, such as three of the immediately preceding calibration amounts or others), and the sum may be divided by the number of calibration amounts being evaluated (including both the one or more previous calibration amounts and the calibration amount) to generate an average calibration amount for a trailing window defined by the number of previous calibration amounts employed. In some embodiments, the average calibration amount may be added to the predicted interval energy expenditure amount to generate a modified predicted interval energy expenditure amount. In some embodiments, modified resource distribution information may be generated employing one or more similar processes as described with regard to the resource distribution information based on the modified predicted interval energy expenditure amount instead of the predicted interval energy expenditure amount. In some embodiments, one or more resource consumption control engines 412 may provide modified resource consumption control instructions to the agent employing one or more similar processes as described with regard to the resource consumption control instructions based on the modified resource distribution information instead of the resource distribution information. In some embodiments, the processes described with regard to obtaining the metrics associated with the control session through providing the modified resource consumption control instructions may continue until the control session terminates. For example, one or more of these continuing processes may be executed for each intake session, complete interval, qualifying period, or others.

In one or more of the various embodiments, one or more network computers, such as one or more network computers 300 (for example, one or more resource consumption control computers 406, consumption control engines 324, consumption control engines 412, or others), may control one or more agents 402 based on the one or more modified resource consumption instructions. In some of the various embodiments, controlling one or more agents 402 may include providing the modified resource consumption instructions, thereby facilitating causing one or more client computers, such as one or more client computers 200 (for example, one or more client computers 102-105 or others) associated with or included in one or more agents 402 to perform one or more actions in accordance with the one or more modified resource consumption instructions, such as one or more of the following: causing one or more agents 402 or one or more components of one or more agents 402 to intake or consume one or more resources, amounts of resources, resource recipes, resource types, or others; causing one or more projectors 246, displays 250, audio interfaces 256, haptic interfaces 264, or others to provide one or more outputs (for example, displays, audio notifications, haptic notifications, or others) of one or more instructions, recommendations, interface components, alerts, or others (for example, when one or more applications 220 are next launched, downloaded, opened, or otherwise engaged, when the one or more modified resource instructions are obtained by client computer 200, or others); or others.

In one or more of the various embodiments, modifying the predicted interval energy expenditure amount in a control session for an agent (or the modified predicted interval energy expenditure amount if system 400 has been calibrated one or more times in the control session for the agent) may facilitate improving one or more performance criteria, such as increasing a performance criterion of correlation between the objective performance of the agent and one or more outputs of one or more models, model portions, sub-models, or others (for example, one or more of the value of the correlation coefficient or the absolute value of the correlation coefficient describing the direction or magnitude of the relationship between the objective performance of the agent and one or more outputs of one or more models, model portions, sub-models, or others, such as the predicted energy consumption needs amount, the specific-units needs amount for one or more resource types, the normalized-units needs amount for one or more resource types, the resource distribution information, the resource consumption instructions, or others). In some of the various embodiments, modifying the predicted interval energy expenditure amount in a control session for an agent (or the modified predicted interval energy expenditure amount if system 400 has been calibrated one or more times in the control session for the agent) by reducing the predicted interval energy expenditure amount may reduce the magnitude of the one or more outputs and may increase the objective performance of the agent (for example, weight loss), thereby increasing the performance criterion of the value of the correlation coefficient and the performance criterion of the absolute value of the correlation coefficient (for example, bringing the value of the correlation coefficient closer to positive one). In other embodiments, modifying the predicted interval energy expenditure amount by increasing the predicted interval energy expenditure amount may increase the magnitude of the one or more outputs and may increase the objective performance of the agent (for example, weight gain), thereby increasing the performance criterion of the value of the correlation coefficient and the performance criterion of the absolute value of the correlation coefficient (for example, bringing the value of the correlation coefficient closer to positive one).

In one or more of the various embodiments, modifying the predicted interval energy expenditure amount in a control session for an agent (or the modified predicted interval energy expenditure amount if system 400 has been calibrated one or more times in the control session for the agent) may improve the responsiveness, reliability, ease-of-use, or other characteristics of system 400. For example, the modification may calibrate one or more components of system 400 to compensate for one or more divergences in an agent's interpretation of the resource consumption instructions, the agent's recording of consumption information, makeup anomalies or divergences associated with the agent (for example, manufacturing or genetic variances from an average agent of the agent type having the agent characteristics information), or others, without requiring system 400 to engage in more computationally expensive modelling to identify and directly address the one or more divergences. Accordingly, in some of the various embodiments, the modifications described with regard to system 400 based on the comparison of the performance feedback with the output of one or more performance models may improve performance criterion while improving the efficiency of one or more agents 402, resource consumption control computers 406, or other components in system 400.

In one or more of the various embodiments, the one or more performance monitors assigned to the agent may monitor one or more of the agent's actions, such as the agent's adherence to or divergence from the resource consumption control instructions, adherence to or divergence from the modified resource consumption control instructions, accuracy of recording resource consumption information, activities (for example, training, exercise, or others), impairment status, or others. In some of the various embodiments, resource consumption control computer 406 may provide a dashboard (for example, a dashboard employing a graphical user interface provided in a web page, an application, or others) to a display of a performance monitor. In some embodiments, the dashboard may include monitor information, such as raw data in the obtained metrics, simplified forms of the obtained metrics, supplemental information generated based on the obtained metrics, or others. In some embodiments, the dashboard may include information associated with multiple agents. In some embodiments, the multiple agents may be agents that are assigned to the performance monitor, are associated with each other (for example, agents on the same sports team, agents within the same athletic program at a school, or others), have one or more portions of agent characteristics information in common (for example, same or similar agent type, same or similar age, same or similar weight, same or similar material makeup, same or similar objectives, or others. In some embodiments, the dashboard may display averages of monitor information associated with the multiple agents, one or more sub-groups within the multiple agents (for example, athletes of a particular gender or others), or others. In some embodiments, the dashboard may display percentages associated with the monitor information, such as the percent of agents in the multiple agents that are meeting their intake needs (for example, protein intake needs or others), engaging in intake sessions between particular hours, above or below their intake needs, engaging in their typical activities, or others. In some embodiments, the dashboard may display one or more flags when one or more portions of the monitor information associated with the agent diverge beyond a threshold from an expected value, from average monitor information of the multiple agents, from one or more historical trends associated with the agent, or others. In some embodiments, the monitor information in the dashboard may be updated in real time, such as when the information is obtained from agent, when the information is processed by resource consumption control computer 406, or others. In other embodiments, the monitor information in the dashboard may be provided as a snapshot at a predetermined time, at the time at which the performance monitor logs into the web page, application, or other element that acts as a gateway to the dashboard, or others. In some embodiments, the dashboard may obtain monitor metrics (for example, login time, login duration, time of communications, or others) associated with one or more actions of the performance monitor and may provide the obtained monitor metrics to resource consumption control computer 406. In some embodiments, resource consumption control computer 406 may adjust the predetermined time at which to provide the snapshot based on one or more averages of one or more portions of the obtained monitor metrics. In some embodiments, the dashboard may provide one or more interface components (e.g., one or more buttons, check boxes, radio buttons, text fields, or others) that facilitate the performance monitor providing feedback (for example, reporting one or more flags, divergences, percentages or others; providing instructions to remedy the reported information; or others) to the agent, providing feedback to one or more entities that supervise the agent (for example, one or more coaches, trainers, or others), overriding one or more instructions to the agent, altering information or inputs provided by the agent, creating one or more accounts associated with the agent, one or more other actions described herein as being performed by the agent, or others. In some embodiments, the performance monitor may be a specialist in one or more fields, such as one or more fields associated with the performance objectives of the multiple agents. In other embodiments, the performance monitor may include a form of artificial intelligence, learning engines, neural networks, or others that may employ one or more processes described with regard to the dashboard and, optionally, without a display.

In one or more of the various embodiments, one or more resource classification engines 408 may generate one or more resource data objects (for example, see FIG. 7) for each resource that an agent is expected to consume or that the agent reports as having been consumed based on one or more portions of resource characteristics information associated with the one or more resources. In some of the various embodiments, an agent, an entity that supervises the agent, a performance monitor, administrator, or others may communicate one or more portions of the resource characteristics information over one or more networks to one or more resource consumption control computers 406. In some embodiments, one or more portions of the resource characteristics information may be provided via a user interface (for example, a web page, application, or others) in various forms, such as email, user interface (UI) notification, instant message, or others. In other embodiments, one or more portions of the resource characteristics information may be provided or generated by one or more sensors or sensor interfaces (for example, one or more cameras 240, video interfaces 242, sensor interfaces 262, or others). In some embodiments, the resource characteristics information may include one or more energy sources (for example, protein, carbohydrates, fats, or others) in terms of percentages (for example, a given amount of a resource may derive various percentages of its energy from different energy sources) or specific units (for example, grams or others).

In one or more of the various embodiments, each resource may be classified as being of a resource type. In some of the various embodiments, each resource may have one or more characteristics associated with multiple resource types, and the resource may be classified to one of the multiple resource types based on one or more models, model portions, submodels, conditions, or others. In some embodiments, one or more conditions of the selected resource type may be evaluated based on one or more portions of the resource characteristics information. In some embodiments, each resource type may have one or more conditions that, if satisfied, indicate that the one or more portions of the resource characteristics information may match with the resource type. In some embodiments, a condition may include that the one or more portions of the resource characteristics information has not matched with a higher-ranking resource type in a hierarchy of resource types. For example, vegetables may have highest priority, carbohydrates may have the second highest priority, proteins may have the third highest priority, and fats may have the lowest priority. Accordingly, in some embodiments, a resource that satisfies conditions of multiple resource types may only match with the satisfied resource type that has the highest priority. In some embodiments, a condition may include most of the percentage of the one or more energy sources of the resource being the resource type (for example, the resource derives a greater percentage of its energy from the evaluated resource type than the percentage of its energy derived from each other resource type). In some embodiments, a condition may include the highest specific units amount of the one or more energy sources of the resource being the resource type. In some embodiments, one or more of multiple conditions must be satisfied or others.

In one or more of the various embodiments, when a resource is classified as having a resource type, specific-units amounts for the resource may be transformed into normalized-units amounts for the new resource based on one or more portions of the resource characteristics information and the associated resource type. In some of the various embodiments, an expected number of normalized units per a predetermined number of specific units may be based on historical analysis provided by a third party, average sample analysis, user input, or others. In some embodiments, the energy source information may be employed to generate the number of normalized units per number of specific units. In other embodiments, the number of normalized units per number of specific units may be standard based on the average or expected number for the matched resource type (for example, 25 grams of a resource that is a resource type of protein may equate to one serving of protein or others). In some embodiments, resource data object of the resource may be populated with the numbers of normalized or specific units associated with the resource.

In one or more of the various embodiments, one or more resource recipe engines 410 may generate one or more resource recipes to be employed by one or more agents 402 based on one or more portions of resource characteristic information in two or more resource data objects associated with two or more resources. In some of the various embodiments, two or more resources may be evaluated to generate a compatibility score associated with the combination of the two or more resources. In some embodiments, the resource and the other resource may be compatible with each other if one or more portions of their respective resource characteristic information overlaps, matches, satisfies one or more conditions, fails to overlap, fails to match, or others. In some embodiments, the degree of compatibility may be reflected in the score based on the amount of overlap, the quantities of overlaps, the number of conditions satisfied, or others. For example, the resource and the other resource may be compatible with each other if their respective resource characteristic information indicates that they may both be breakfast foods, if only one of them takes a large amount of time or effort to prepare, if they are of different resource types, if their combination correlates to a predicted high likelihood of agent or control session success, or others. In some embodiments, compatibility may vary based on geographic region for which the recipe is intended. In some embodiments, one or more configuration files, rules, custom scripts, or others may define one or more thresholds for a minimum number of resources to include in a recipe based on one or more factors, such as whether the recipe is a snack or a meal recipe, the type of snack or meal (for example, standard, pre-workout, post-workout, quick preparation, normal preparation, gourmet preparation, or others).

In one or more of the various embodiments, one or more portions of the resource characteristics information of each resource in the recipe may be evaluated to select one or more resource consumption or intake phases to associate with the recipe. In some of the various embodiments, each phase associated with each of the resources in the recipe may be selected. In some embodiments, one or more phases associated with the recipe may vary based on geographic region, agent type, or others for which the recipe is intended. In some embodiments, one or more resource recipes may be generated based on one or more portions of the resource characteristics information associated with the selected resources and based on the one or more selected resource consumption phases. In some embodiments, generating the recipe may include generating or populating one or more recipe data objects associated with the recipe. In some embodiments, the one or more recipe data objects may be generated or populated employing one or more similar processes as described with regard to one or more other data object generation or population processes of system 400, one or more processes described with regard to one or more data structures described with regard to FIG. 6 or 7, or others. In some embodiments, one or more attributes of the one or more recipe data objects may indicate one or more restrictions (for example, allergies, dietary choices or restrictions, intake type, geographical associations, intake phases, or others).

In one or more of the various embodiments, the client computers, agents 402, performance monitors 404, or others may have vertical access to one or more agent repositories, the agent data objects in the one or more agent repositories, information included in or associated with the agent data objects, or others, thereby permitting access to authorized information in one or more agent repositories associated with the one or more control sessions that are associated with the client computers, agents 402, performance monitors 404, or others. In some of the various embodiments, the client computers, agents 402, performance monitors 404, or others may lack horizontal access, thereby precluding accessing to information in one or more agent repositories associated with one or more control sessions that are not associated with the client computers, agents 402, performance monitors 404, or others. Accordingly, in some embodiments, the client computers, agents 402, performance monitors 404, or others may track progress of the control sessions with which the client computers, agents 402, performance monitors 404, or others are directly involved, yet information associated with the other control sessions remains private or protected.

In contrast, in one or more of the various embodiments, one or more engines in resource consumption control computer 406 or system 400 (for example, one or more performance monitors, resource recipe engines 410, consumption control engines 412, metrics analysis engines 414, prediction engines 416, or others) may have both vertical and horizontal access to the one or more agent repositories, the agent data objects in the one or more agent repositories, the information included in or associated with the agent data objects, or others, thereby permitting access to information associated with each control session. In some of the various embodiments, metrics analysis engine 414 may analyze metrics associated with multiple active or completed control sessions and provide the results of the analysis to consumption control engine 412. In some embodiments, one or more metrics analysis engines 414 or others may classify or categorize one or more control sessions, agents 402, or others based on evaluation of one or more data objects associated with the one or more control sessions, agents 402, or others and may include the classification or categorization in the results. In some embodiments, one or more of the services provided by metrics analysis engine 414 may be provided by one or more third-party services (for example, one or more services available under the mark MIXPANEL or others). Accordingly, in some embodiments, consumption control engine 412 may predictively or responsively select one or more models, portions of one or more models, sub-models in one or more models, strategies, tactics, or others to employ in one or more active or impending control sessions based on the results provided by metrics analysis engine 414 for one or more control sessions with similar characteristics to the one or more active or impending control sessions (for example, one or more predictions discovered by one or more prediction engines 416). In some embodiments, consumption control engine 412 may predictively or responsively adjust or select one or more models, portions of one or more models, sub-models in one or more models, strategies, tactics, or others employed in one or more active or impending control sessions based on the results provided by metrics analysis engine 414 indicating that one or more models, portions of one or more models, sub-models in one or more models, strategies, tactics, or others was more effective in one or more other control sessions with similar characteristics associated with the one or more active or impending campaigns. Accordingly, in some embodiments, because system 400 may facilitate horizontal and vertical analysis of control sessions, system 400 may facilitate analyzing or modifying control sessions more quickly than client computers, agents 402, performance monitors 404, specialists, or others could otherwise do on their own with vertical access, thereby improving security of agent information and effectiveness of control sessions, such as decreasing time taken to execute a control session to achieve objectives or others. Moreover, in some embodiments, because consumption control engine 412 may horizontally analyze tenants of system 400, consumption control engine 412 may have and may apply one or more rules to prevent competing control sessions (for example, two or more control sessions that have conflicting objectives, instructions, or others).

In one or more of the various embodiments, one or more selections, compositions, characteristics, or others of one or more initiation, launch, or execution processes or of one or more actions or other processes described with regard to one or more performance monitors 404, resource consumption control computers 406, resource classification engines 408, resource recipe engines 410, consumption control engines 412, metrics analysis engines 414, prediction engines 416, or other components of system 400 (for example: selecting or executing one or more models, portions of one or more models, sub-models of one or more models, or others; one or more models, portions of one or more models, sub-models of one or more models themselves; selecting or generating one or more parameters, variables, coefficients, constants, or other components of one or more models, portions of one or more models, sub-models of one or more models; or others) may be based on one or more machine learning models, linear regression models, heuristics models, or others derived from relevant historical metrics for one or more other control sessions. In some of the various embodiments, the relevant historical metrics may include information associated with one or more other agents, geographical or logical territories, entities associated with agents, performance monitors, or others having one or more similar characteristics or one or more characteristics that correspond to one or more characteristics of the control session, agent, agents associated with the agent, the entity associated with the agent, geographical or logical territory associated with the agent, or others. In some embodiments, the one or more machine learning models, linear regression models, heuristic models, or others may be employed to discover one or more candidate selections or modifications that are predicted to improve system performance, agent performance, or other performance or to reduce time the control session may be expected to obtain one or more objectives. In some embodiments, the one or more predictions may be based on or include one or more predictions discovered by prediction engine 416. In other embodiments, one or more machine learning models, linear regression models, heuristics models, or others may be applied to historical metrics for one or more other control sessions associated with one or more data objects of one or more supervisory entities, agents 402, performance monitors 404, resource consumption control computers 406, or others to provide one or more portions of the discoveries. In some embodiments, a deep-learning artificial neural network may be trained using historical information to classify or identify one or more features of the one or more selections, compositions, characteristics, or others that are predicted to have increased success rates (for example, increased likelihood of achieving one or more objectives, decreased expected time until one or more objectives may be achieved, increased wellness of the agent during or after the control session, or others) based on one or more predictions discovered by prediction engine 416.

For example, one or more discoveries may indicate that one or more agents that have actual performances that diverge from the expected performances by amounts within one or more particular ranges or that have one or more portions of the agent characteristics information matching one or more conditions or ranges of conditions, struggled or failed to adhere to the resource consumption control instructions (for example, struggle or failure to adhere to one or more intake schedules, to adhere to the instructed amounts of normalized-units to consume for one or more of the multiple resource types, or others), and, in some embodiments, one or more discoveries may indicate that adjusting the resource control instructions (for example: adjusting one or more particular aspects of the intake schedules, such as including additional snack intake sessions at particular times or others; adjusting the recommended or instructed resource recipes in a particular manner or others; or others). Accordingly, in some embodiments, one or more agents that have one or more portions of the agent characteristics information matching the one or more conditions or ranges of conditions or that have actual performances that diverge from the expected performances by amounts within the one or more particular ranges may be provided with the adjusted resource control instructions (for example, transforming the normalized-units needs amounts or modified normalized-units needs amounts into the adjusted resource control instructions based on one or more adjusted portions of resource distribution information or others). As another example, one or more discoveries may indicate that presenting the instructions in different formats, at different times, at different phases, at different frequencies, or others may improve performance of one or more agents that have one or more portions of the agent characteristics information matching the one or more conditions or ranges of conditions or that have actual performances that diverge from the expected performances by amounts within the one or more particular ranges. Accordingly, in some embodiments, one or more discovery-identified characteristics of one or more performance monitors 404, resource recipe engines 410, consumption control engines 416, metrics analysis engines 414, prediction engines 416, models, portions of one or more models, sub-models of one or more models, processes, actions, or others may be modified based on the horizontal evaluation of the one or more obtained metrics and one or more corresponding predictions discovered by prediction engine 416.

In one or more of the various embodiments, resource consumption control computer 406 may obtain interaction metrics associated with the resource consumption control instructions or the dashboard provided to one or more agents 402, performance monitors 404, or others. In some of the various embodiments, each interaction with the instructions, user interface displaying the instructions, or the dashboard may be reported to resource consumption control computer 406, and resource consumption control computer 406 may obtain interaction metrics associated with each interaction, such as date, time of day, frequency, duration, type, application used to view the instructions or dashboard, user-interface interaction (for example, mouse clicks, types of clicks, mouse hover time, opens, visits, refreshes, timing of actions, most-recent login time, quantities of actions, or others), delay between providing the instruction or dashboard and the interaction, or others. In some embodiments, resource consumption control computer 406 may adjust one or more discovery-identified characteristics of one or more performance monitors 404, resource recipe engines 410, consumption control engines 416, metrics analysis engines 414, prediction engines 416, models, portions of one or more models, sub-models of one or more models, processes, actions, or others that are predicted to have increased success rates (for example, increased likelihood of achieving one or more objectives, decreased expected time until one or more objectives may be achieved, increased wellness of the agent during or after the control session, or others) based on one or more predictions discovered by prediction engine 416 and the obtained interaction metrics.

In one or more of the various embodiments, one or more of the selections of one or more models, model portions, or sub-models described herein may be performed for each intake, interval, period, control session, or others.

In one or more of the various embodiments, system 400 may increase the efficiency of control sessions, accuracy of performance models, quality of results of control sessions, or others by one or more of improving communication between the various components of each control session (for example, one or more agents, performance monitors, resource consumption control computers, or others), enabling oversight by an objective entity (for example, one or more performance monitors or others), calibrating control system 400, resource consumption control computer 406, or others based on a comparison of performance feedback with the output of a performance model, or others. In some of the various embodiments, when one or more control session components (for example, one or more agents, performance monitors, resource consumption control computers, or others) are offline from one or more networks, one or more sending, forwarding, or other control session components in system 400 (for example, one or more agents, performance monitors, resource consumption control computers, or others) may cache one or more portions of one or more communications intended for the one or more offline campaign components. In some embodiments, the one or more sending, forwarding, or other control session components may detect that the one or more offline components went offline based on one or more of losing one or more connections to one or more applications, engines, or others in the one or more offline components, failing to obtain a response to one or more communications (e.g., one or more ACK communications or others), or others. In some embodiments, when the one or more control session components come back online, the one or more rejoining components may notify one or more other control session components. In some embodiments, the one or more sending, forwarding, or other control session components may detect the return of the one or more rejoining components based on one or more notifications, reconnections to one or more engines in the one or more rejoining components, responses to one or more prior communications to the one or more rejoining components, or others.

In one or more of the various embodiments, when the one or more control session components come back online, the one or more sending, forwarding, or other control session components in system 400 may resynchronize the one or more rejoining control session components in a synching process. In some of the various embodiments, the synching process may include auditing information in the one or more rejoining components to evaluate one or more states of the one or more rejoining components, whether one or more portions of information in the one or more rejoining components is up to date, or others. In some embodiments, the audit may include obtaining a timestamp associated with a most-recent update of the one or more rejoining components. In some embodiments, the synching process may include evaluating the audited information to produce one or more results that indicate whether one or more states, information, or others in the one or more rejoining components are out of date. In some embodiments, the evaluation may include comparing the timestamp to one or more timestamps associated with a most-recent update provided to one or more other control session components. In some embodiments, the synching process may include updating information in the one or more rejoining components to reflect updated information associated with the control session, such as state information associated with the control session (e.g., the control session is being initialized, has launched, has concluded, or others) or others.

In one or more of the various embodiments, system 400 may improve efficiency, responsiveness, reliability, or others by selectively making various elements available offline. In some of the various embodiments, when an agent installs, loads, opens, or otherwise initializes a downloaded (or native) element, such as one or more applications or engines (for example, performance tracking engine 218, performance monitor engine 222, or others), the downloaded element may perform a call to one or more data structures (for example, one or more tables or others) in one or more repositories (for example, resource model repository 418, performance model repository 422, an agent data object repository, or others) to pull one or more data structures, portions of one or more data structures, or others to populate one or more elements employed or provided by the downloaded element, such as one or more graphical displays or others, and may store the pulled information locally at the agent. In some embodiments, the downloaded element may provide one or more input fields (for example, one or more input fields in a user interface, an API associated with one or more other applications or engines of the agent, or others) that facilitates the agent inputting information into the downloaded element. In some embodiments, the input information may be stored locally at the agent (in some embodiments, one or more portions of the input information may also be pushed to resource consumption control computer 406). Accordingly, in some embodiments, the downloaded element may be responsive to agent actions both when the agent is connected to a network and when the network is unavailable to the agent (and, therefore, resource consumption control computer 406 is unavailable to the agent).

In one or more of the various embodiments, the downloaded element may have one or more configuration files, rules, custom scripts, or others that selectively maintain one or more portions of the locally stored input or pulled information, archive one or more portions of the locally stored input or pulled information, remove one or more portions of the locally stored input or pulled information, or others based on one or more characteristics of one or more portions of the locally stored input or pulled information. In some embodiments, the one or more configuration files, rules, custom scripts, or others may locally maintain one or more portions of the local information until predetermined event (for example, a predetermined date or time is reached, the one or more portions of information have a predetermined age, or others) based on one or more characteristics of the local information (for example, agent-settings or configuration information, administrator settings, information type, criticality of the information, time since last use of the information, frequency of use of the information, frequency of change to the information, likelihood of re-use, or others). In some embodiments, when a predetermined event associated with one or more portions of local information occurs, the one or more configuration files, rules, custom scripts, or others may archive or remove the one or more portions of the local information based on one or more characteristics of the local information (for example, agent-settings or configuration information, administrator settings, information type, criticality of the information, time since last use of the information, frequency of use of the information, frequency of change to the information, likelihood of re-use, or others). In some embodiments, the one or more configuration files, rules, custom scripts, or others may remove one or more portions of local information when the agent reconnects to the network and provides the one or more portions of local information to resource consumption control computer 406. In some embodiments, the one or more configuration files, rules, custom scripts, or others may remove one or more portions of local information when the agent reconnects to the network if the resource consumption control computer 406 informs the downloaded element that the one or more portions of local information are out of date or if the downloaded element obtains updated information that takes priority over the one or more portions of local information (for example, updated versions of information or others). Accordingly, system 400 may facilitate the downloaded element being responsive to agent actions when offline from the network and may facilitate preventing over filling local storage or memory of the agent.

In one or more of the various embodiments, system 400 may improve communication reliability or coverage by employing one or more failovers. In some of the various embodiments, the one or more failovers may include multiple communication providers that may be dynamically employed based on availability of the one or more other communication providers, such as multiple email providers (for example, SENDRID, ANDRIL, or others) or others. In some embodiments, the one or more failovers may include multiple communication modalities that may be dynamically employed based on availability of the one or more other communication modalities, such as two or more of email, SMS (for example, SMS provided by TOYO or others), user interface (UI) notification, instant message, or others. In some embodiments, one or more configuration files, rules, custom scripts, or others may execute logic (for example, confirming that no ACK communications were received or others) to prevent duplicate actions when switching providers, modes, or others. In some embodiments, one or more pools of providers or modalities may be provided, and a provider or modality may be selected from the one or more pools based on one or more input conditions, on a rotating basis, or others. Accordingly, system 400 facilitates conducting control sessions over wide geographic regions with varying levels of network reliability or coverage by facilitating employing multi-modal networks and dynamically changing modes of communication from one mode to another based on availability of the communication modes. For example, a performance monitor may attempt to send a communication to an agent through a performance monitor engine (for example, performance monitor engine 222), and the performance monitor engine may dynamically select one or more modes of communication, one or more providers, or others based on network availability associated with the one or more modes of communication, one or more providers, or others. In some embodiments, the performance monitor engine may provide one or more notifications (for example, a UI notification or others) that the performance monitor engine is attempting to dynamically select a different mode of communication, provider, or others. In other embodiments, the performance monitor engine may dynamically select the different mode of communication, provider, or others without further notification.

In one or more of the various embodiments, one or more engines (for example, one or more performance tracking engines 218, performance monitor engines 222, resource classification engines 318 or 408, resource recipe generation engines 322 or 410, consumption control engines 324 or 412, metrics analysis engines 326 or 414, prediction engines 416, or others) may employ one or more other engines to perform one or more actions (for example, one or more of the actions described with regard to one or more components of system 400). In some of the various embodiments, employing another engine to perform an action may include providing one or more instructions, portions of information (for examples, one or more portions of one or more inputs to one or more models, model portions, sub-models, or others), signals, or others to the other engine, thereby facilitating the other engine performing the action and, optionally, obtaining one or more instructions, portions of information, signals, or others from the other engine based on the other engine performing the action. In some embodiments, employing another engine to perform an action may include providing one or more instructions, portions of information (for examples, one or more portions of one or more inputs to one or more models, model portions, sub-models, or others), signals, or others to the other engine and obtaining one or more one or more instructions, portions of information, signals, or others from the other engine based on one or more actions performed by the other engine responsive to the one or more provided communications, thereby facilitating one or more of the engine or one or more further engines performing the action based on one or more portions of the one or more obtained communications from the other engine.

In one or more of the various embodiments, one or more engines (for example, one or more performance tracking engines 218, performance monitor engines 222, resource classification engines 318 or 408, resource recipe generation engines 322 or 410, consumption control engines 324 or 412, metrics analysis engines 326 or 414, prediction engines 416, or others) may instantiate one or more other engines to perform one or more actions (for example, one or more of the actions described with regard to one or more components of system 400). In some of the various embodiments, instantiating another engine to perform an action may include generating an instance of the other engine, thereby facilitating the other engine performing the action. In some embodiments, instantiating another engine to perform an action may include generating one or more representations of the other engine (for example, setting one or more flags, variable values, or others to, for example, indicate that the other engine is tasked with ensuring that the action is performed or others). In some embodiments, instantiating another engine to perform an action may include employing the other engine to perform the action.

Figure 5:
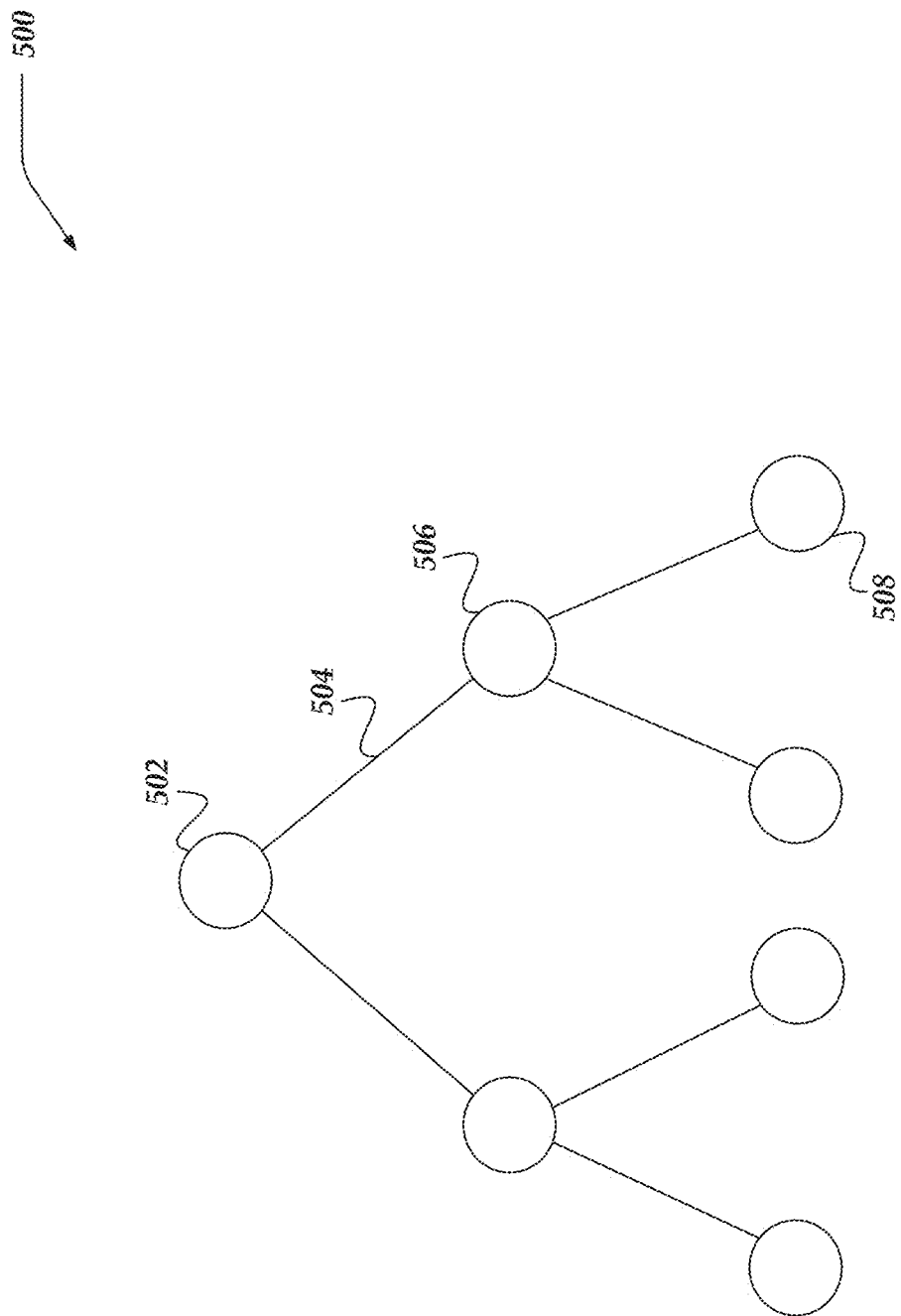
FIG. 5 illustrates a logical representation of a portion of an example decision model that may be employed by the system of FIG. 4.

FIG. 5 illustrates a logical representation of a portion of example decision model 500 that may be employed by one or more engines in system 400 to execute one or more portions of one or more processes, actions, or others described with regard to the one or more engines. In one or more of the various embodiments, a decision tree may be an example way to implement decision model 500. In some of the various embodiments, one or more performance monitors 404, resource classification engines 408, resource recipe engines 410, consumption control engines 412, metrics analysis engines 414, prediction engines 416, or others may be arranged to support models that have various shapes or structures. In some embodiments, the processes used by one or more engines may be adapted or varied depending on the structure of a given model. In some embodiments, the particular shape or structure of a model may be shared with an engine to facilitate the engine selecting a protocol that may be compatible with the model. In some embodiments, one or more engines may be arranged to identify one or more models that may be able to provide an output that is appropriate for the agent characteristics information or metrics associated with the agent. Accordingly, in some embodiments, the protocol used to evaluate the agent characteristics information or metrics associated with the agent may be different depending on the structure of the selected model. In some embodiments, each model may be associated with meta-data that identifies the type of structure of the model.

In other embodiments, a model or its corresponding parameter model may define one or more protocols that it may be compatible with.

In one or more of the various embodiments, one or more engines may traverse decision model 500 to select or execute one or more models, portions of one or more models, or sub-models in one or more models. In some of the various embodiments, traversing decision model 500 may begin at root node 502, continue through one or more edges 504, optionally continue through one or more intermediate nodes 506, and conclude at one or more leaf nodes 508. In some embodiments, the path followed in decision model 500 may depend on conditions, outputs of model portions, or outputs of sub-models at each root node 502 or intermediate node 506. In some embodiments, each edge 504 may represent a portion of a path that is defined by the output of the immediately preceding root or intermediate node 502, 506.

Figure 6:
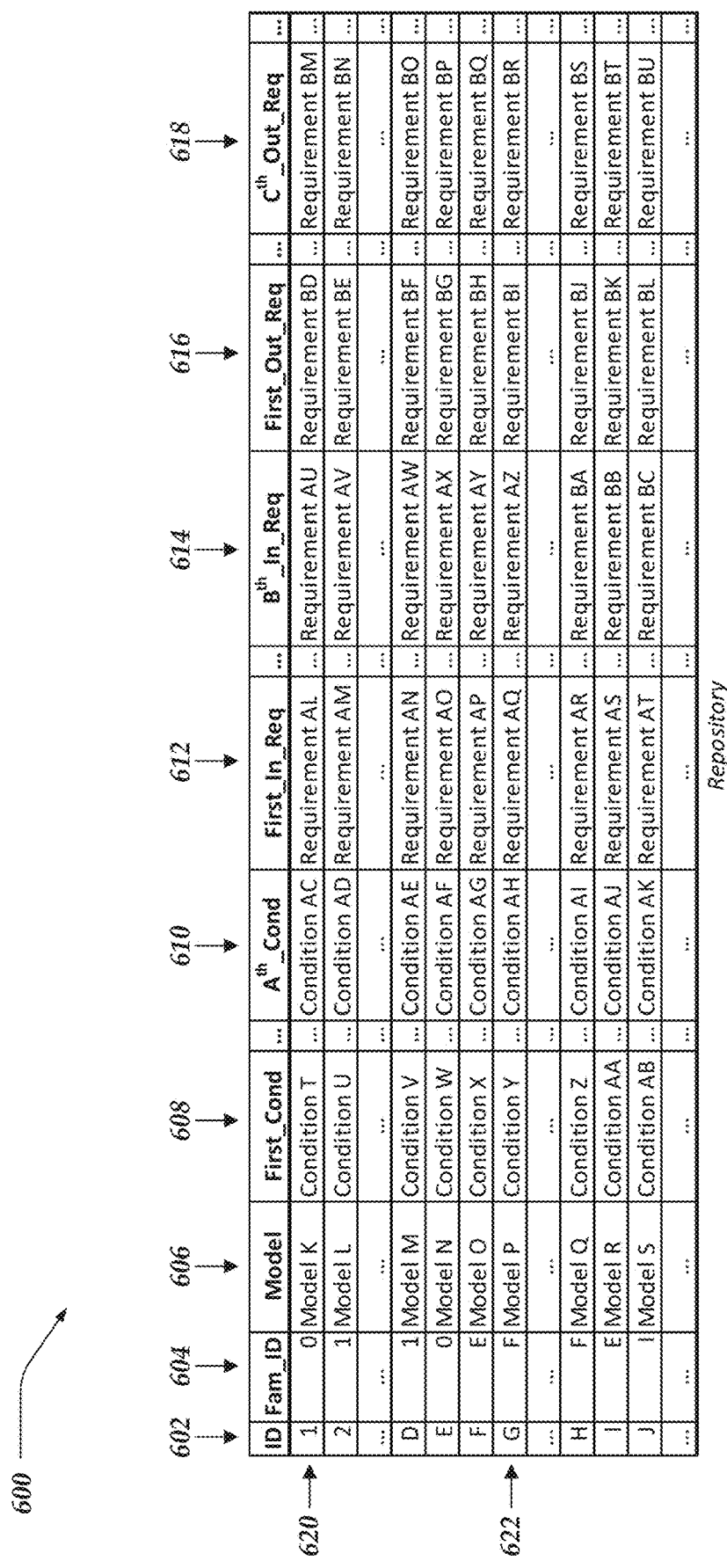
FIG. 6 shows a logical representation of an example performance model repository that may be employed by the system of FIG. 4.

In one or more of the various embodiments, each root or intermediate node 502, 506 may represent a condition or requirement associated with one or more models, such as the example models in the example repository of FIG. 6, and each leaf node 508 may represent an identifier, such as one of the model identifiers or family identifiers of FIG. 6. For example, the initial edge followed after root node 502 may depend on the type of agent, the next edge followed after the intermediate node to which the initial edge leads may depend on whether a particular material makeup of the agent is above or below a threshold identified by the intermediate node, and the next edge may lead to a leaf node that identifies a model or family identifier associated with a model, model portion, or sub-model to execute. In some of the various embodiments, each root or intermediate node 502, 506 may represent a decision to be made within a model, model portion, or sub-model that is being executed. For example, the initial edge followed after root node 502 may depend on a resource intake type being analyzed when executing the example resource model of FIG. 7, the next edge followed after the intermediate node to which the initial edge leads may depend on which family identifier has a highest count among the resources that have resource characteristics that match the resource intake type, and the next edge may lead to a leaf node that identifies a resource or resource family to employ in the next resource intake of the resource intake type. Accordingly, in some embodiments, each leaf node 508 may represent a class label, which may identify an action to be taken (for example, selecting a model, model portion, or sub-model identified by the class label, selecting a resource, resource family, or others to be employed, or others). In some embodiments, one or more engines may execute one or more models, model portions, or sub-models during the traverse of decision model 500 based on the path followed and may employ one or more outputs of the one or more executed models, model portions, or sub-models in the evaluation at subsequent node.

FIG. 6 shows a logical representation of example performance model repository 600 that may be employed by system 400. In one or more of the various embodiments, performance model repository 600 may include one or more data objects (for example, records or others) that may represent performance models, such as performance models 424. In some of the various embodiments, performance model repository 600 may include a number of named attributes, such as ID 602, Family_ID 604, Model 606, First_Condition 608 through $A^{th}$_Condition 610, First_Input_Requirement 612 through $B^{th}$_Input_Requirement 614, First_Output_Requirement 616, $C^{th}$_Output_Requirement 618, or others. In some embodiments, for each data object, the values for identifiers, such as those shown as entries for attribute 602 or others may be sequential numbers, non-sequential numbers, strings, or others. In the example shown in FIG. 6, each data object may be defined or characterized by one or more values associated with the named attributes. For example, data object 620 with ID of one has a Family_ID of 0, Model of Model K, First_Condition of Condition T, $A^{th}$_Condition of Condition AC, First_Input_Requirement of Requirement AL, $B^{th}$_Input_Requirement of Requirement AU, First_Output_Requirement of Requirement BD, and $C^{th}$_Output_Requirement of Requirement BM.

In one or more of the various embodiments, if model repository 600 involves hierarchies (for example, trees or others for one or more models, sets of models, portions of one or more models, sub-models of one or more models, or others), nested data models or objects, or other relationships, Family_ID values associated with attribute 604 may reference ID values associated with attribute 602 or others. Accordingly, in some of the various embodiments, model repository 600 may be self-referential, thereby facilitating querying and providing information associated with relationships between multiple models, model portions, or sub-models without referencing a further model repository that includes data objects that represent relationships. Examples of relationships may include being associated with the same or related agent characteristics, portions of agent characteristics, sets of agent characteristics, purposes, activities, geographic or logical territories, supervisory entities, or others.

In the example shown in FIG. 6, data object 620 represents a performance model (Model K) that is associated with no parent models, one or more agent characteristics or conditions (or ranges of agent characteristics or conditions) that may be employed to select the performance model (for example, Condition T, Condition AC, or others), one or more requirements (or requirement ranges) that one or more values of one or more input parameters must satisfy to be validly analyzed by the performance model (for example, Requirement AL, Requirement AU, or others), one or more requirements (or requirement ranges) that one or more output values of one or more output parameters must satisfy to be considered one or more valid outputs (for example, Requirement BD, Requirement BM, or others), or others. In contrast, in the example shown in FIG. 6, data object 622 with ID of G has a Family_ID of F, Model of Model P, First_Condition of Condition Y, $A^{th}$_Condition of Condition AH, First_Input_Requirement of Requirement AQ, $B^{th}$_Input_Requirement of Requirement AZ, First_Output_Requirement of Requirement BI, and $C^{th}$_Output_Requirement of Requirement BR. Accordingly, in one or more of the various embodiments, data object 622 may represent a performance model (Model P) that is in the same family as performance models with ID of F and E (F being a parent of G and a child of E) and that is associated with one or more agent characteristics or conditions (or ranges of agent characteristics or conditions) that may be employed to select the performance model (for example, Condition Y, Condition AH, or others), one or more requirements (or requirement ranges) that one or more values of one or more input parameters must satisfy to be validly analyzed by the performance model (for example, Requirement AQ, Requirement AZ, or others), one or more requirements (or requirement ranges) that one or more output values of one or more output parameters must satisfy to be considered one or more valid outputs (for example, Requirement BI, Requirement BR, or others), or others.

In one or more of the various embodiments, multiple data objects in model repository 600 may form one or more portions or sub-models of a model, as defined by one or more of the attributes, such as Fam_ID 604. In some of the various embodiments, a model may be traversed by executing one or more processes or actions defined by one or more data objects associated with one or more portions or sub-models in the model (for example: one or more actions or processes defined by or associated with one or more outputs or others of one or more mathematical models such as equations, prediction models as described with regard to prediction engine 416, decision models such as decision model 500, or others included in or referenced by Model attribute 606; executing one or more models, model portions, or sub-models included in Model attribute 606; or others). In some embodiments, one or more model portions or sub-models may be selected for execution when traversing the model based on one or more characteristics or conditions (or ranges of characteristics or conditions) associated with one or more elements being evaluated or analyzed (for example, one or more amounts, portions of agent characteristics information, or others). Accordingly, in some embodiments, a hierarchy in a model may be represented by one or more values in Fam_ID attribute 604. In some embodiments, one or more model portions or sub-models may be associated with multiple paths within one or more models. Accordingly, in some embodiments, performance model repository 600 may facilitate dynamically selecting one or more models, model portions, or sub-models based on one or more characteristics or conditions of one or more elements or phases in one or more processes, actions, control sessions, or others, thereby facilitating improving computational performance of system 400, reliability of system 400, consistency throughout system 400 when updates are provided, or others.

In one or more of the various embodiments, system 400 may include one or more repositories that include one or more data objects for each element in or associated with system 400. In some of the various embodiments, each element type (for example, agents, control sessions, interactions, actions, metrics, or others) may have a dedicated repository that includes data objects for each element of the element type. In some embodiments, each data object for each element may have attributes that correspond to features or characteristics of the element type of the element. For clarity, data repository 600 is shown using tabular format. In some embodiments, data sets or data objects may be arranged differently, such as using different formats, data structures, objects, or others. For example, data repository 600 may be structured as a JSON object (for example, a JSON tree or others).

Figure 7:
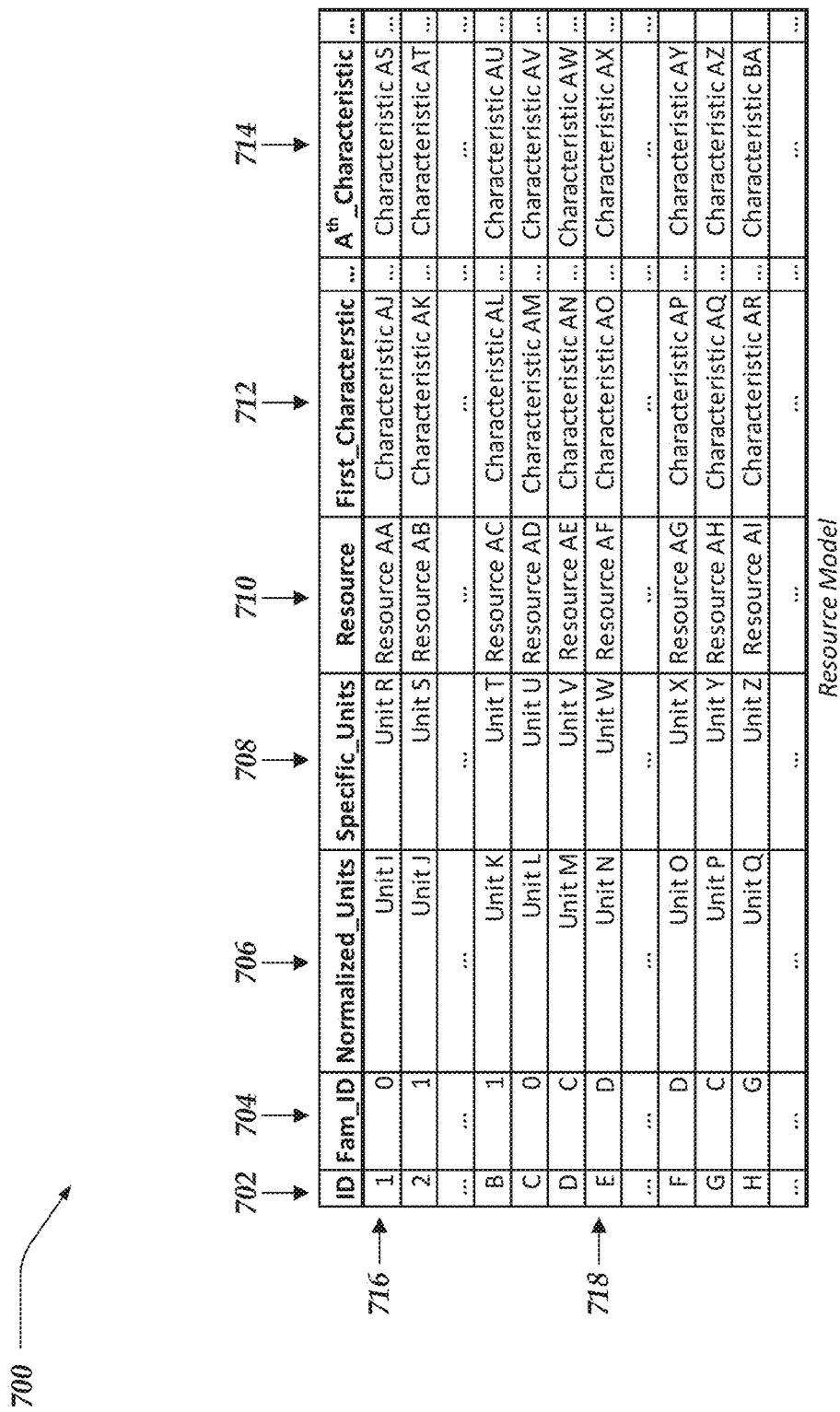
FIG. 7 illustrates a logical representation of an example resource model that may be employed by the system of FIG. 4.

FIG. 7 illustrates a logical representation of example resource model 700 that may be employed by system 400. In one or more of the various embodiments, resource model 700 may include one or more data objects (for example, records or others) that may represent resources available to one or more agents or resources that resource consumption control computer 406 may instruct one or more agents to consume. In some of the various embodiments, resource model 700 may include a number of named attributes, such as ID 702, Fam_ID 704, Normalized_Units 706, Specific_Units 708, Resource 710, First_Characteristic 712 through $A^{th}$_Characteristic 714, or others. In some embodiments, for each data object, the values for identifiers, such as those shown as entries for attribute 702 or others may be sequential numbers, non-sequential numbers, strings, or others. In the example shown in FIG. 7, each data object may be defined or characterized by one or more values associated with the named attributes. For example, data object 716 with ID of one has a Family_ID of 0, Normalized_Units of Unit I, Specific_Units of Unit R, Resource of Resource AA, First_Characteristic of Characteristic AJ, and $A^{th}$_Characteristic of Characteristic AS.

In one or more of the various embodiments, if resource model 700 involves hierarchies (for example, resource types, resource families, intake types, objective types, or others), nested data objects, or other relationships, Family_ID values associated with attribute 704 may reference ID values associated with attribute 702 or others. Accordingly, in some of the various embodiments, resource model 700 may be self-referential, thereby facilitating querying and providing information associated with relationships between multiple resources without referencing a further relationship model that includes data objects that represent relationships. Examples of relationships may include being associated with the same or related resource type, resource family, intake type, objective type, activity type, purposes, activities, geographic or logical territories, supervisory entities, or others).

In the example shown in FIG. 7, data object 716 represents a resource (Resource AA) that is associated with no parent resources, an amount of normalized units that equates to an amount of specific units of the resource, one or more characteristics (for example, resource type, resource family, intake type such as breakfast, objective type, activity type, purposes, activities, geographic or logical territories in which the resource is readily available, geographical or logical territories in which the resource is has one or more positive or negative enjoyabilities such as taste ratings, supervisory entities, enjoyability such as a taste rating, pairings or pairing types that are acceptable or unacceptable, likelihood of allergies, warnings, or others), or others. In contrast, in the example shown in FIG. 7, data object 718 with ID of E has a Family_ID of D, Normalized_Units of Unit N, Specific_Units of Unit W, Resource of Resource AF, First_Characteristic of Characteristic AO, and $A^{th}$_Characteristic of Characteristic AX. Accordingly, in one or more of the various embodiments, data object 718 may represent a resource (Resource AF) that is in the same family as resources with ID of D and C (D being a parent of E and a child of C) and that is associated with an amount of normalized units that equates to an amount of specific units of the resource, one or more characteristics, or others. In some embodiments, one or more resource classification engines 408 may generate or populate one or more resource models 700 or data objects in one or more resource models 700. In other embodiments, one or more resource models 700 or data objects in one or more resource models 700 may be generated or populated based on input into a user interface.

In one or more of the various embodiments, one or more resource recipe engines 410 may employ one or more resource models 700 or data objects in one or more resource models 700 to generate one or more resource recipes to employ in one or more control sessions. In some of the various embodiments, one or more resource recipes may be stored or defined by one or more recipe models that have similar structures or characteristics to resource model 700, with attributes that correspond to the resource recipes. In some embodiments, one or more resource consumption control engines 412 may employ one or more resource or recipe models or one or more data objects in one or more resource or recipe models to generate one or more portions of the resource consumption control instructions. For clarity, resource model 700 is shown using tabular format. In some embodiments, data sets or data objects may be arranged differently, such as using different formats, data structures, objects, or others. For example, resource model 700 may be structured as a JSON object (for example, a JSON tree or others).

Figure 8:
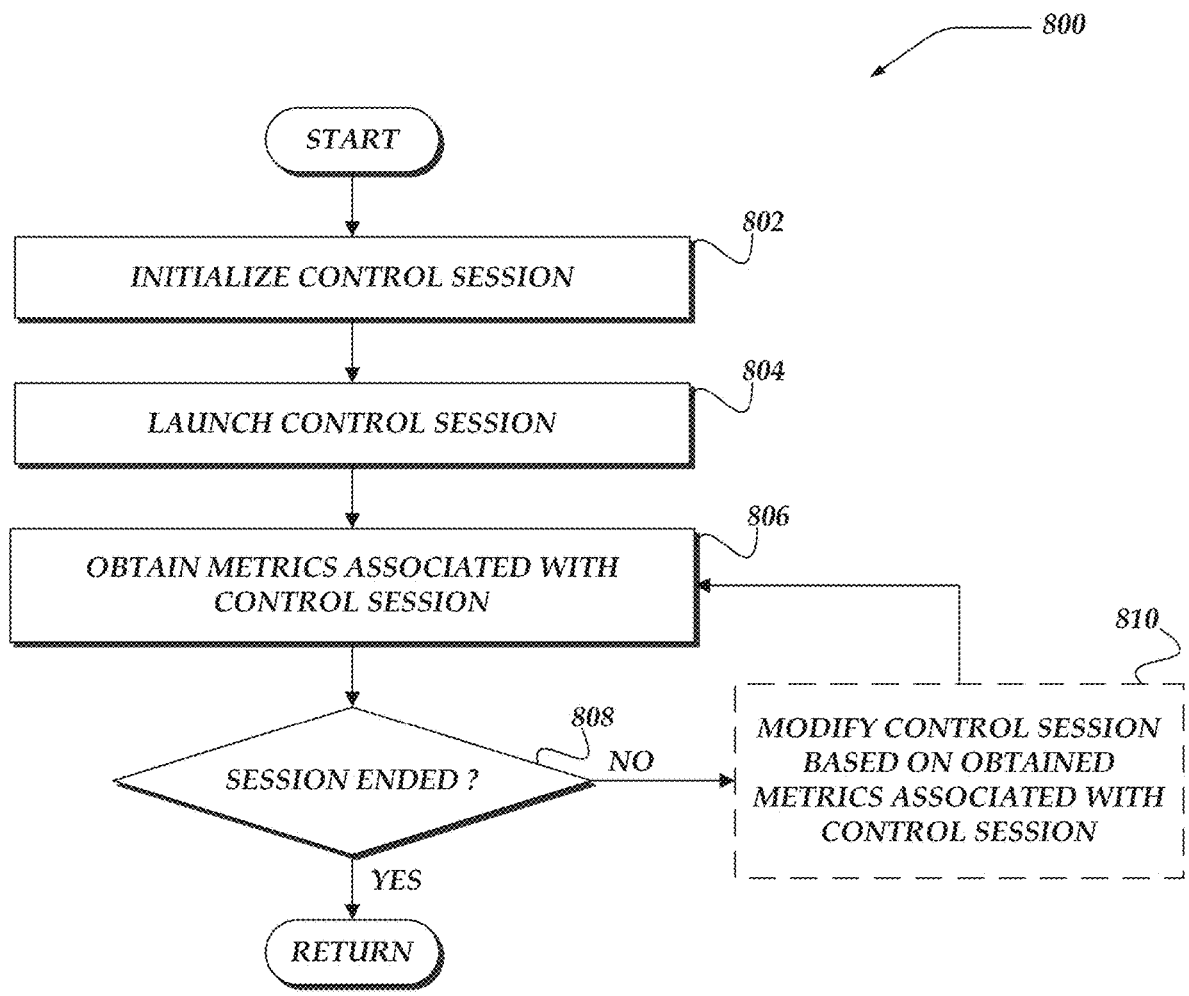
FIG. 8 shows an overview flowchart of an example process for controlling resource consumption.

FIG. 8 shows an overview flowchart of example process 800 for controlling resource consumption. One or more portions of process 600 may be performed by one or more engines in one or more client computers or network computers (for example: one or more performance tracking engines 218, performance monitor engines 222, or others in one or more client computers 200; one or more resource classification engines 318, resource recipe generation engines 322, consumption control engines 324, metrics analysis engines 326, or others in one or more network computers 300; or others), such as one or more client or network computers associated with or included in one or more agents 402, performance monitors 404, resource consumption control computer 406, or others. In one or more of the various embodiments, after a start block, at block 802, one or more control sessions may be initialized for one or more agents, such as a control session to control resource consumption by an agent. In some of the various embodiments, initializing the control session may include assigning one or more performance monitors to the agent or the control session, onboarding or otherwise initializing communication with the agent, obtaining information (for example, identification information, contact information, agent characteristics information, or others) from the agent, or others. In some embodiments, initializing the control session may begin with the agent, an entity that supervises the agent, the performance monitor, or others communicating one or more requests over one or more networks to a resource consumption control computer. In some embodiments, the request may be provided via a user interface (for example, a web page, application, or others) in various forms, such as email, user interface (UI) notification, instant message, or others.

At block 804, in one or more of the various embodiments, the one or more control sessions may be launched. In some of the various embodiments, launching the one or more control sessions may include providing one or more resource consumption instructions to the one or more agents associated with the one or more control sessions.

At block 806, in one or more of the various embodiments, one or more metrics associated with the one or more launched control sessions may be obtained. In some of the various embodiments, the one or more metrics may be based on one or more actions of the one or more agents associated with the one or more control sessions (for example, one or more actions performed responsive to the one or more resource consumption instructions, resource consumption information, objective performance information, mouse clicks, types of clicks, mouse hover time, opens, visits, refreshes, timing of actions, most-recent login time, quantities of actions, or others).

At decision block 808, in one or more of the various embodiments, if the one or more control sessions have ended, control may return to a calling process; otherwise, control may flow to block 810. In some of the various embodiments, a control session may end based on the occurrence of one or more conditions, such as meeting or exceeding one or more objectives associated with the control sessions, expiration of a defined duration of the control session, arbitrary feedback from one or more agents, supervisory entities, performance monitors, or others, exhausting one or more resources, an agent or supervisory entity ceasing to participate in the control session, or others.

At block 810, in one or more of the various embodiments, optionally, the one or more control sessions may be modified based on the obtained metrics. Examples of modifying a control session may include calibrating one or more components in system 400, such as one or more of the following: modifying one or more parameters, variables, coefficients, constants, or other components of one or more models, portions of one or more models, sub-models of one or more models, or others; modifying one or more outputs of one or more models, portions of one or more models, sub-models of one or more models, or others; or others. In some of the various embodiments, one or more outputs of one or more models, portions of one or more models, sub-models of one or more models may be modified. Block 810 is optional because the one or more control sessions may continue without modification. For example, analysis of the one or more metrics may indicate that one or more candidate modifications will not or is unlikely to increase the effectiveness of one or more control sessions. From block 810, control flows to block 806 to continue the one or more control sessions.

In some embodiments, process 800 may continue operating until one or more events occur, such as meeting or exceeding one or more objectives associated with the control sessions, expiration of a defined duration of the control session, arbitrary feedback from one or more agents, supervisory entities, performance monitors, or others, exhausting one or more resources, an agent or supervisory entity ceasing to participate in the control session, a user configures process 800 to terminate operation, or others. Next, control may be returned to a calling process.

Figure 9:
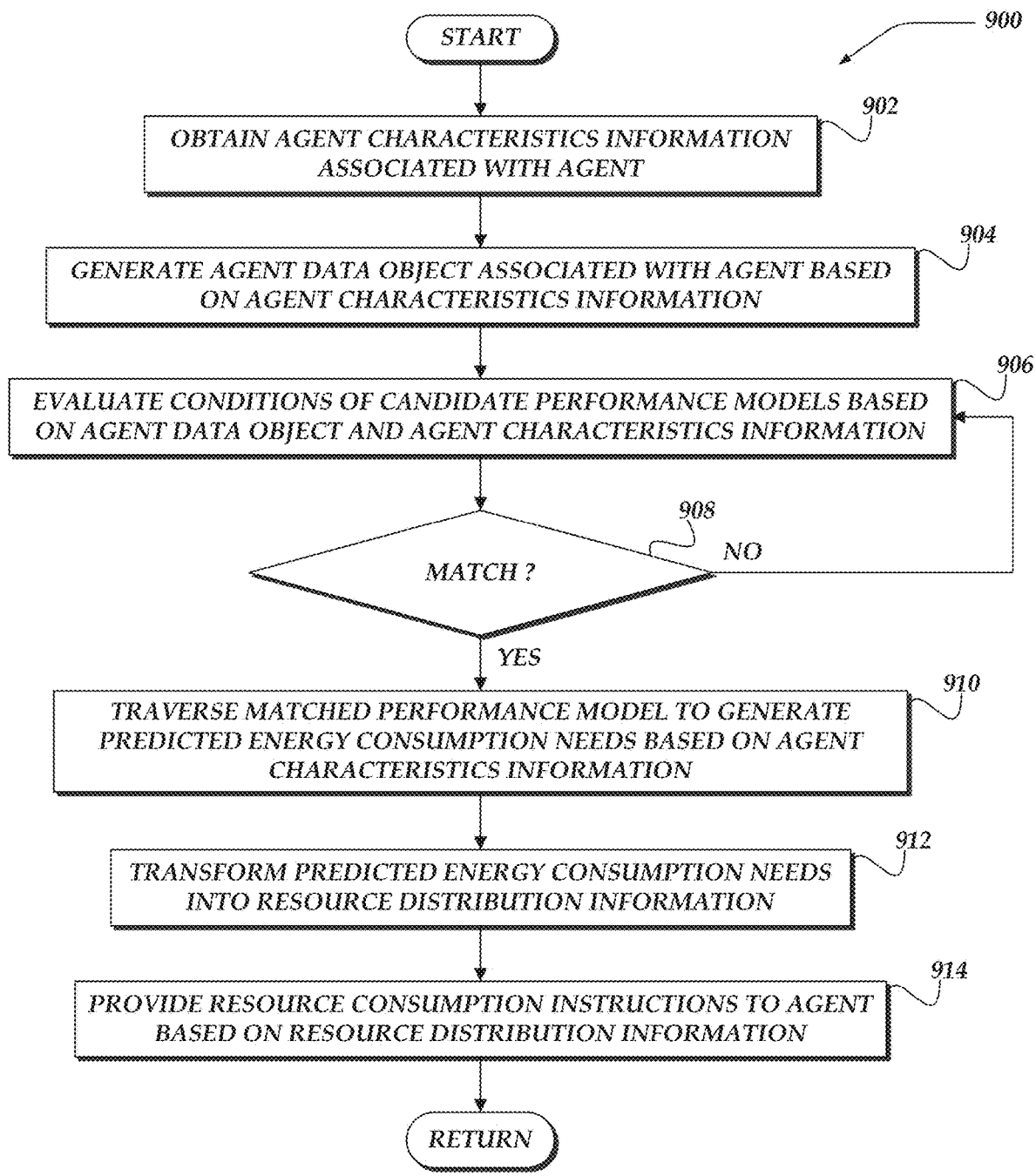
FIG. 9 illustrates a logical flow diagram of an example process for initializing and launching a control session.

FIG. 9 illustrates a logical flow diagram of example process 900 for initializing or launching a control session. One or more portions of process 900 may be performed by one or more engines in one or more client computers or network computers (for example: one or more performance tracking engines 218, performance monitor engines 222, or others in one or more client computers 200; one or more resource classification engines 318, resource recipe generation engines 322, consumption control engines 324, metrics analysis engines 326, or others in one or more network computers 300; or others), such as one or more client or network computers associated with or included in one or more agents 402, performance monitors 404, resource consumption control computer 406, or others. In one or more of the various embodiments, one or more portions of process 900 may correspond to or be included in one or more of blocks 802, 804, or others. In some of the various embodiments, after a start block, at block 902, agent characteristics information associated with an agent may be obtained to initialize or launch a control session, such as a control session to control resource consumption by an agent. In some embodiments, the agent, an entity that supervises the agent, a performance monitor assigned to the agent, or others may communicate one or more portions of the agent characteristics information over one or more networks to one or more resource consumption control computers 406. In some embodiments, one or more client computers 200 may monitor or provide one or more portions of the agent characteristics information based on one or more user interactions with a user interface (for example, a web page, application, or others) in various forms, such as email, user interface (UI) notification, instant message, or others. In other embodiments, one or more portions of the agent characteristics information may be provided or generated by one or more sensors or sensor interfaces (for example, one or more cameras 240, video interfaces 242, sensor interfaces 262, or others) associated with the agent (for example, one or more sensors or sensor interfaces that are included in client computer 200, that are in communication with client computer 200, or others).

At block 904, in one or more of the various embodiments, one or more agent data objects associated with the agent may be generated based on one or more portions of the agent characterization information. In some of the various embodiments, the one or more agent data objects may be generated or populated employing one or more processes as described with regard to system 400, one or more data structures with regard to FIG. 6 or 7, or others. For example, a record may be appended to a tabular data structure and populated with one or more portions of the agent characteristics information being included in various fields in the record that are associated with various attributes that correspond to the one or more portions of the agent characteristics information.

At block 906, in one or more of the various embodiments, one or more conditions of one or more candidate performance models, candidate model portions, or candidate sub-models (for example, one or more candidate models 424 in one or more performance model repositories 422, such as repository 600) may be evaluated based on one or more portions of the one or more agent data objects that include or represent the one or more portions of agent characteristics information. In some embodiments, one or more values of one or more portions of the agent characteristics information may be compared to one or more conditions or ranges of conditions associated with the one or more candidate performance models, candidate model portions, or candidate sub-models (for example, one or more values included in one or more attributes, such as attributes 608, 610, or others). In some embodiments, a candidate model, model portion, or sub-model may be considered a match if the one or more values of one or more portions of the agent characteristics information equals, falls within a predetermined range of, or falls between one or more values of one or more conditions or ranges of conditions associated with the candidate performance model, model portion, or sub-model. In other embodiments, a candidate model, model portion, or sub-model may be considered a match if the one or more values of one or more portions of the agent characteristics information are closer to one or more values of one or more conditions or ranges of conditions associated with the candidate performance model, model portion, or sub-model than one or more values of one or more conditions or ranges of conditions associated with one or more other candidate performance models, model portions, or sub-models. In some embodiments, a candidate model, model portion, or sub-model may be considered a match based on one or more portions of one or more selection processes described with regard to system 400, such as one or more selection processes based on one or more machine learning models, linear regression models, heuristics models, or others derived from relevant historical metrics for one or more other control sessions, one or more predictions discovered by prediction engine 416, deep-learning networks, or others.

At decision block 908, in one or more of the various embodiments, if one or more of the candidate models, model portions, or sub-models are a match based on the evaluation, control may flow to block 910; otherwise, control may flow to block 906 to evaluate one or more further candidate models, model portions, or sub-models. In some of the various embodiments, if no match is found after evaluating a predetermined number of the candidate performance models, model portions, or sub-models, the criteria for determining a match may be adjusted. For example, based on the criteria adjustment, a candidate model, model portion, or sub-model may be considered a match if the one or more values of one or more portions of the agent characteristics information are closer to one or more values of one or more conditions or ranges of conditions associated with the candidate performance model, model portion, or sub-model than one or more values of one or more conditions or ranges of conditions associated with one or more other candidate performance models, model portions, or sub-models.

At block 910, in one or more of the various embodiments, the one or more matched performance models, model portions, or sub-models may be traversed to generate a predicted energy consumption needs amount based on one or more portions of the agent characteristics information. In some of the various embodiments, traversing a matched performance model may include executing one or more model portions or sub-models in the matched performance model based on the one or more portions of the agent characteristics information to provide one or more outputs and executing one or more other model portions or sub-models in the matched performance model based on the one or more outputs.

At block 912, in one or more of the various embodiments, the predicted energy consumption needs amount may be transformed into resource distribution information. In some of the various embodiments, the resource distribution information may indicate one or more amounts of one or more resources or resource types that the agent should intake during one or more expected resource intake sessions based on one or more portions of the agent characteristics information.

At block 914, in one or more of the various embodiments, one or more resource consumption instructions may be provided to the agent based on one or more portions of the resource distribution information. In some of the various embodiments, resource consumption instructions may instruct the agent to intake or consume one or more amounts of one or more resources or resource types per interval, intake session, or others. In some embodiments, different types or formats of resource consumption instructions may be provided based on agent type, agent display type, or others.

In some embodiments, process 900 may continue operating until the control session terminates, the control session has fully launched, or a user configures process 900 to terminate operation. Next, control may be returned to a calling process.

Figure 10:
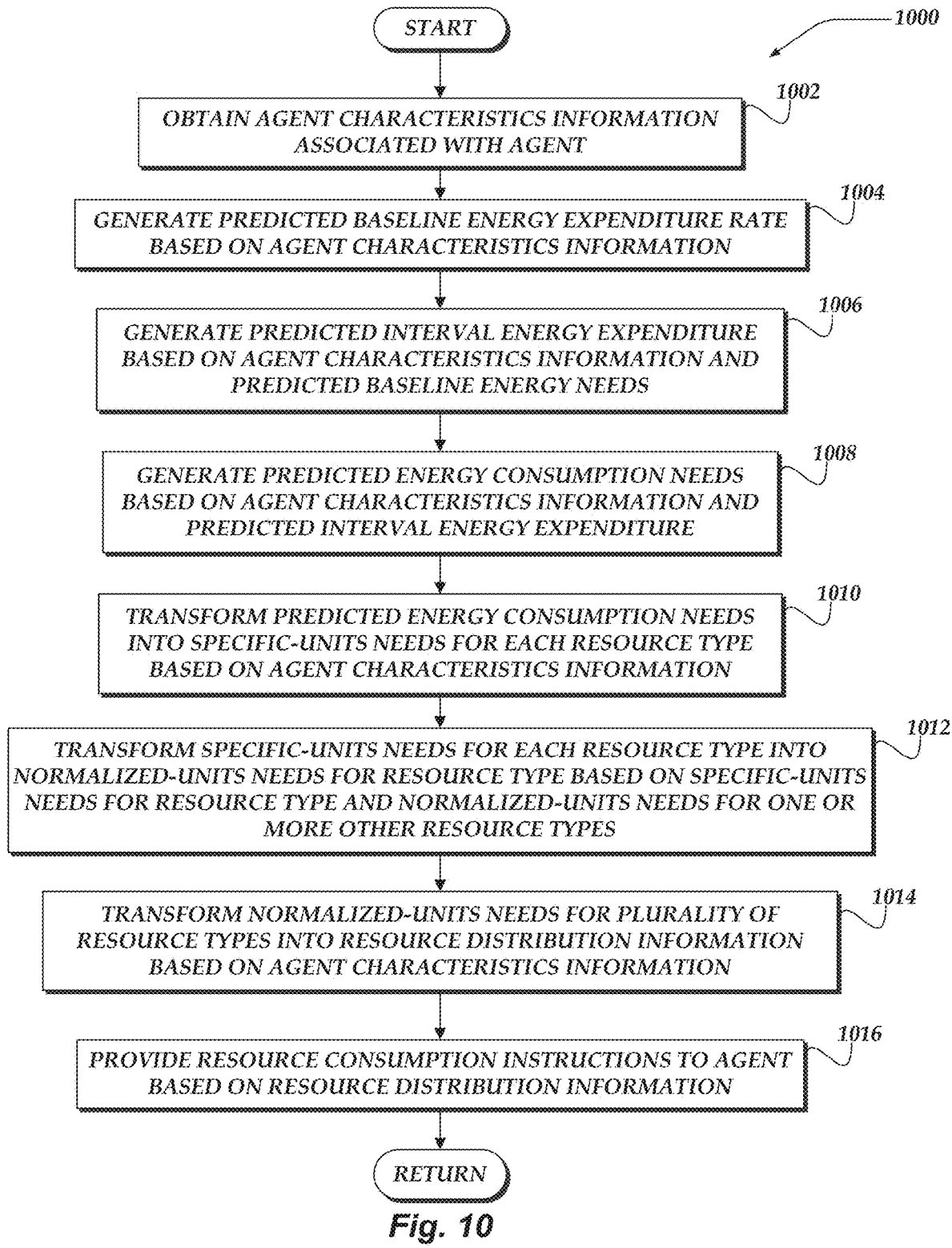
FIG. 10 shows a logical flowchart of an example process for initializing or launching a control session.

FIG. 10 shows a logical flowchart of example process 1000 for initializing or launching a control session. One or more portions of process 1000 may be performed by one or more engines in one or more client computers or network computers (for example: one or more performance tracking engines 218, performance monitor engines 222, or others in one or more client computers 200; one or more resource classification engines 318, resource recipe generation engines 322, consumption control engines 324, metrics analysis engines 326, or others in one or more network computers 300; or others), such as one or more client or network computers associated with or included in one or more agents 402, performance monitors 404, resource consumption control computer 406, or others. In one or more of the various embodiments, one or more portions of process 1000 may correspond to or be included in one or more of blocks 802, 804, 902, 904, 910, 912, 914, or others. In some of the various embodiments, after a start block, at block 1002, agent characteristics information associated with an agent may be obtained to initialize or launch a control session, such as a control session to control resource consumption by an agent. In some embodiments, the agent, an entity that supervises the agent, a performance monitor assigned to the agent, or others may communicate one or more portions of the agent characteristics information over one or more networks to one or more resource consumption control computers 406. In some embodiments, one or more portions of the agent characteristics information may be provided via a user interface (for example, a web page, application, or others) in various forms, such as email, user interface (UI) notification, instant message, or others. In other embodiments, one or more portions of the agent characteristics information may be provided or generated by one or more sensors or sensor interfaces (for example, one or more cameras 240, video interfaces 242, sensor interfaces 262, or others) associated with the agent (for example, one or more sensors or sensor interfaces that are included in client computer 200, that are in communication with client computer 200, or others).

At block 1004, in one or more of the various embodiments, a predicted baseline energy expenditure rate of the agent may be generated based on one or more portions of the agent characteristics information. In some of the various embodiments, one or more of the selected or matched performance models, model portions, or sub-models described with regard to one or more of blocks 906, 908, or others may be employed, executed, or traversed to generate the predicted baseline energy expenditure rate.

In one or more of the various embodiments, one or more equations may be selected based on one or more portions of the agent characteristics information, such as agent type (for example, internal combustion engine, Stirling engine, male gender, female gender, or others), weight, known material makeup (for example, quantities or percentages of one or more elements, such as aluminum, iron, body fat, or others), age, size (for example, displacement, number of cylinders, height, or others), estimated material makeup, activity rating (for example, a value selected on a predetermined scale such as a value between zero and one that indicates an amount of use above rest per predetermined period, such as a duration or intensity of the use, or others), or others. For example, the one or more equations may be selected based on whether the age is greater than or less than one or more predetermined thresholds (for example, 19 years old or others), gender, whether body fat is known or estimated, whether body fat is greater than or less than one or more predetermined thresholds (for example, 20% for males, 25% for females, or others), whether the activity rating is greater than or less than one or more predetermined thresholds (for example, 50%, 1.5 on a scale from 1-2, or others), or others. In some of the various embodiments, one or more outputs of the one or more selected equations may be weighted based on the one or more portions of the agent characteristics information. In some embodiments, the one or more weighted outputs may be summed to provide the predicted baseline energy expenditure rate of the agent. For example, in a control session for a male agent with an age that is greater or equal to 19, an estimated body fat of greater than or equal to 20%, and an activity rating of less than 1.5, a Mifflin-St. Jeor equation (for example, [9.99×weight in kilograms]+[6.25×height in meters×100]−[4.92×age in years]+5, or others) and a Katch-McArdle equation (for example, [21.6× [[1−body fat percentage as a decimal value]×weight in kilograms]]+370, or others) may be selected, with the output of the Mifflin-St. Jeor equation being multiplied by 0.8 and the output of the Katch-McArdle equation being multiplied by 0.2, and the weighted outputs of the equations may be summed to provide a BMR amount for the agent.

At block 1006, in one or more of the various embodiments, a predicted interval energy expenditure amount may be generated based on one or more portions of the agent characteristics information and the predicted baseline energy expenditure rate. In some of the various embodiments, one or more of the selected or matched performance models, model portions, or sub-models described with regard to one or more of blocks 906, 908, or others may be employed, executed, or traversed to generate the predicted interval energy expenditure amount.

In one or more of the various embodiments, one or more equations may be selected based on one or more portions of the agent characteristics information, such as activity rating (for example, a value selected on a predetermined scale such as a value between zero and one that indicates an amount of use above rest per predetermined period, such as a duration or intensity of the use, or others), lifestyle rating (for example, a value selected on a predetermined scale such as between 0 and 1 that indicates how physically active the agent is during the agent's time outside of the activities measured by the activity rating, such as the agent's professional time and non-training leisure time or others), impairment status (for example, one or more values that indicate whether the agent is damaged or injured, the seriousness of the damage or injury, or others), or others. For example, the one or more equations may be selected based on whether the age is greater than or less than one or more predetermined thresholds (for example, 19 years old or others), gender, or others), or others. In some of the various embodiments, the predicted baseline energy expenditure rate and one or more values of one or more portions of the agent characteristics information may be employed as inputs to the one or more selected equations, and one or more outputs of the selected equations may provide the predicted interval energy expenditure amount. For example, in a control session for an agent with an age that is greater or equal to 19, a sum of the number one and the impairment status (for example, a selected value of 0 for no impairment, 0.2 for minor impairment, 0.4 for major impairment, or others) may be added to a sum of the activity rating (for example, a selected value between 0 and 1 that indicates an amount of use above rest per day or others, such as during training) and the lifestyle rating (for example, a selected value between 0 and 1 that indicates how physically active the agent is during the agent's time outside of the activities measured by the activity rating, such as the agent's professional time and non-training leisure time) to provide a result, and the result may be multiplied by the predicted baseline energy expenditure rate to provide the predicted interval energy expenditure amount.

In one or more of the various embodiments, the activity rating employed to generate the predicted interval energy expenditure amount may represent an estimated activity rating for the agent. In some of the various embodiments, the activity rating may represent an average activity rating for the agent. In some embodiments, the activity rating may represent actual tracked activity intensity or duration for a particular interval based on metrics obtained from the agent (for example, metrics input in a user interface, metrics provided based on sensor data, or others). In some embodiments, historical actual tracked activity ratings for particular intervals may be employed by one or more prediction engines (for example, prediction engine 416 or others) to predict activity ratings for particular intervals during the control session. For example, the historical actual tracked activity ratings may indicate that the agent typically has an activity rating of 1.8 on Mondays, 1.6 on Tuesdays, 1.7 on Wednesdays, and 1.4 on Thursdays, with a predicted activity rating being unavailable for Fridays-Sundays. Accordingly, in some embodiments, the predicted interval energy expenditure amount may represent an amount of energy that the agent is expected to expend on average per interval based on the estimated activity rating or the average activity rating for the agent. In some embodiments, the predicted average-interval energy expenditure amount may be employed as a default value for the predicted interval energy expenditure amount. In some embodiments, the predicted interval energy expenditure amount may represent an amount of energy that the agent is expected to expend in a particular interval based on the tracked activity rating or the predicted activity rating for the particular interval. In some embodiments, the predicted particular-interval energy expenditure amount may be employed as the value for the predicted interval energy expenditure amount when available or when one or more conditions are satisfied, such as the predicted particular-interval energy expenditure amount exceeding the predicted average-interval energy expenditure amount or others. In some embodiments, the predicted particular-interval energy expenditure amount may be generated based on the same one or more models, model portions, or sub-models as the predicted average-interval energy expenditure amount. In other embodiments, the predicted particular-interval energy expenditure amount may be generated based on a different one or more models, model portions, or sub-models that may be selected based on the availability of the tracked activity rating or the predicted activity rating for the particular interval or one or more other conditions.

At block 1008, in one or more of the various embodiments, a predicted energy consumption needs amount may be generated based on one or more portions of the agent characteristics information and the predicted interval energy expenditure amount. In some of the various embodiments, one or more of the selected or matched performance models, model portions, or sub-models described with regard to one or more of blocks 906, 908, or others may be employed, executed, or traversed to generate the predicted energy consumption needs amount.

In one or more of the various embodiments, one or more equations may be selected based on one or more portions of the agent characteristics information, such as one or more agent objectives or others. For example, in a control session for an agent with an objective of changing weight, an equation may be selected to multiply the number 1,100 by a desired weight change per week in kilograms to provide a product, and the product may be summed with the predicted interval energy expenditure amount to provide a temporary predicted energy consumption needs amount. In some of the various embodiments, the one or more equations may be selected based on a comparison of the one or more agent objectives to one or more thresholds. For example, in a control session where the agent's temporary predicted energy consumption needs amount is less than the predicted baseline energy expenditure rate, the predicted baseline energy expenditure rate may be provided as the predicted energy consumption needs amount. As another example, if the activity rating is less than a predetermined threshold (for example, 0.2 or others) and the temporary predicted energy consumption needs amount minus the predicted interval energy expenditure amount is greater than a predetermined value (for example, 500 or others), the sum of the predicted interval energy expenditure amount and the predetermined value may be provided as the predicted energy consumption needs amount.

At block 1010, in one or more of the various embodiments, the predicted energy consumption needs amount may be transformed into amounts of specific-units needs for multiple resource types based on one or more portions of the agent characteristics information. In some of the various embodiments, one or more of the selected or matched performance models, model portions, or sub-models described with regard to one or more of blocks 906, 908, or others may be employed, executed, or traversed to transform the predicted energy consumption needs amount into the specific-units needs amounts for the multiple resource types.

In one or more of the various embodiments, one or more equations may be selected based on one or more portions of the agent characteristics information, such as known material makeup (for example, quantities or percentages of one or more elements, such as aluminum, iron, body fat, or others), age, size (for example, displacement, number of cylinders, height, or others), estimated material makeup, activity rating (for example, a value selected on a predetermined scale such as a value between 0 and 1 that indicates an amount of use above rest per predetermined period, such as a duration or intensity of the use, or others), impairment status, or others. For example, the one or more equations may be selected based on whether the age is greater than or less than one or more predetermined thresholds (for example, 19 years old or others), gender, whether body fat is known or unknown, whether body fat is greater than or less than one or more predetermined thresholds (for example, 25% or others), whether the activity rating is greater than or less than a prior period or interval for the agent by one or more predetermined thresholds (for example, greater than the activity rating of the prior period or interval by 0.2 or more or others), or others. In some of the various embodiments, the output of the one or more selected equations may be provided as the specific-units needs for the multiple resource types. For example, in a control session of an agent with a known or estimated body fat percentage that is greater than or equal to a predetermined threshold (for example, 25% or others), the agent objective (for example, desired weight change per week in kilograms) may be squared and subsequently multiplied by a coefficient (for example, 0.1809 or others) to produce a first product, the agent objective (for example, desired weight change per week in kilograms) may be squared and subsequently multiplied by a coefficient (for example, 0.3558 or others) to provide a second product, the second product may be subtracted from the first product to provide a difference, the difference may be summed with another value (for example, 1.9849 or others), and the sum may be multiplied by the agent weight in kilograms to provide an amount of specific-units needs for protein (for example, as described in grams or others). As another example, in a control session of an agent, the known or estimated body fat of the agent may be subtracted from the number one to provide a difference, the difference may be multiplied by a coefficient (for example, 0.5 or others), and the difference may be multiplied by the weight of the agent in kilograms to provide an amount of specific-units needs for fat (for example, as described in grams or others). As a further example, in a control session of an agent, the activity rating of the agent (for example, a value selected on a predetermined scale such as a value between 0 and 10 that indicates an amount of use above rest per predetermined period, such as a duration or intensity of the use, or others) may be multiplied by a coefficient (for example, 0.1 or others) to provide a first product, the first product may be summed with the number one to provide a first sum, the first sum may be squared to provide a second product, the second product may be multiplied by a coefficient (for example, 0.19191 or others) to provide a third product, the first product may be multiplied by a coefficient (for example, 0.86831 or others) to provide a fourth product, another value (for example, 0.31988 or others) may be subtracted from the fourth product to provide a first difference, the third product may be subtracted from the first difference to provide a second difference, the second difference may be multiplied by a coefficient (for example, 0.25 or others) to provide a fifth product, the fifth product may be multiplied by the predicted energy consumption needs amount to provide a sixth product, and the sixth product may be divided by the weight of the agent in kilograms to provide an amount of specific-units needs for carbohydrates (for example, as described in grams or others).

In one or more of the various embodiments, the activity rating employed to generate one or more specific-units needs amounts for one or more resource types may represent the estimated activity rating, the average activity rating, the actual tracked activity intensity or duration for a particular interval, or the predicted activity rating for a particular interval. Accordingly, in some of the various embodiments, the amount of specific-units needs for each of one or more resource types may represent an amount of specific-units for the resource type that the agent is expected to need on average per interval to obtain the agent objectives based on the estimated activity rating or the average activity rating for the agent. In some embodiments, the average-interval specific-units needs amount for each of one or more resource types may be employed as a default value for the specific-units needs amount for the resource type. In some embodiments, the amount of specific-units needs for each of one or more resource types may represent an amount of specific-units for the resource type that the agent is expected to need in a particular interval based on the tracked activity rating or the predicted activity rating for the particular interval. In some embodiments, the particular-interval specific-units needs amount for each of one or more resource types may be employed as the value for the specific-units needs amount for the resource type when available or when one or more conditions are satisfied, such as the particular-interval specific-units needs amount for the resource type exceeding the average-interval specific-units needs amount for the resource type or others.

In one or more of the various embodiments, the particular-interval specific-units needs amount for each of one or more resource types may be generated based on the same one or more models, model portions, or sub-models as the average-interval specific-units needs amount for the resource type. In other embodiments, the particular-interval specific-units needs amount for each of one or more resource types may be generated based on a different one or more models, model portions, or sub-models that may be selected based on the availability of the tracked activity rating or the predicted activity rating for the particular interval or one or more other conditions. In some of the various embodiments, a temporary amount of specific-units needs for each of one or more resource types may be generated based on activity time (for example, seconds, minutes, or other units of time of use above rest), and the temporary amount may be modified based on activity intensity (for example, energy expended during the use above rest) to generate the particular-interval specific-units needs amount for the resource type. For example, in a control session of an agent, the total activity time (for example, seconds, minutes, or other units of time of use above rest as tracked, predicted, or others) for a particular interval may be multiplied by a coefficient (for example, 0.06277 or others) to provide a first product, the first product may be summed with a constant (for example, 1.69034 or others) to provide a first sum, the square of the total activity time may be multiplied by a coefficient (for example, 0.00009 or others) to provide a second product, the second product may be subtracted from the first sum to provide a first difference, the activity intensity (for example, calories or other units of energy expended during the use above rest as tracked, predicted, or others) may be divided by the weight of the agent in kilograms to provide a first quotient, the first quotient may be divided by the total activity time to provide a second quotient, the second quotient may be multiplied by a coefficient (for example, 7.78210 or others) to provide a third product, a constant (for example, 0.02724 or others) may be subtracted from the third product to provide a second difference, and the second difference may be multiplied by the first difference to provide an amount of specific-units needs for carbohydrates (for example, as described in grams or others) for a particular interval. At block 1012, in one or more of the various embodiments, the specific-units needs amount for each of the multiple resource types may be transformed into an amount of normalized-units needs for the resource type based on the specific-units-needs amount for the resource type and the normalized-units needs amount for one or more other resource types. In some of the various embodiments, one or more of the selected or matched performance models, model portions, or sub-models described with regard to one or more of blocks 906, 908, or others may be employed, executed, or traversed to transform the specific-units needs amounts for the multiple resource types into the normalized-units needs amounts for the multiple resource types. In some embodiments, transforming the specific-units needs amounts for the multiple resource types into amounts of normalized-units needs for the resource types may facilitate standardizing normalized units according to specific units, may facilitate adjusting for errors in agent perception or measurements, or others. In some embodiments, transforming the specific-units needs amounts for the multiple resource types into amounts of normalized-units needs for the resource types may facilitate overcoming one or more of the deficiencies in employing the "Reference Amounts Customarily Consumed" (RACC) tables defined by the United States Food and Drug Administration (FDA) to generate label serving size requirements. For example, label serving size requirements according to the FDA RACC tables lack consistency in definitions according to energy and macronutrients that may lead to inaccuracies, and, in contrast, one or more resource consumption control computers (for example, one or more resource consumption control computers 406 or others) may provide consistently defined normalized units based on specific units in terms that agents can readily interpret, such as volumes or others.

For example, in a control session of an agent, an amount of specific-units needs for protein (for example, an amount described in grams or others) may be multiplied by a coefficient (for example, 0.04 or others) to provide a first product, the amount of specific-units needs for protein may be multiplied by a coefficient (for example, 4 or others) to provide a second product, the second product may be subtracted from the predicted energy consumption needs amount to provide a difference, the difference may be multiplied by a coefficient (for example, 0.02 or others) to provide a third product, the third product may be multiplied by a coefficient (for example, 0.04 or others) to provide a fourth product, and the fourth product may be subtracted from the first product to provide a normalized-units needs amount for protein. As another example, in a control session of an agent, an amount of specific-units needs for carbohydrates (for example, an amount described in grams or others) may be multiplied by a coefficient (for example, 0.04 or others) to provide a normalized-units needs amount for carbohydrates. As a further example, in a control session of an agent, a normalized-units needs amount for protein may be multiplied by a coefficient (for example, 4 or others) to provide a first product, a normalized-units needs amount for carbohydrates may be multiplied by a coefficient (for example, 2 or others) to provide a second product, the first and second products may be subtracted from a specific-units needs amount for fat (for example, an amount described in grams or others) to provide a difference, and the difference may be multiplied by a coefficient (for example, 0.0909091 or others) to provide a normalized-units needs amount for fat.

At block 1014, in one or more of the various embodiments, the normalized-units needs amounts for the multiple resource types may be transformed into resource distribution information based on one or more portions of the agent characteristics information. In some of the various embodiments, one or more of the selected or matched performance models, model portions, or sub-models described with regard to one or more of blocks 906, 908, or others may be employed, executed, or traversed to transform the normalized-units needs amounts for the multiple resource types into the resource distribution information.

At block 1016, in one or more of the various embodiments, one or more resource consumption control instructions may be provided to the agent based on one or more portions of the resource distribution information. In some of the various embodiments, resource consumption instructions may instruct the agent to intake or consume one or more amounts of one or more resources or resource types per interval, intake session, or others.

In some embodiments, process 1000 may continue operating until the control session terminates, the control session has fully launched, or a user configures process 1000 to terminate operation. Next, control may be returned to a calling process.

Figure 11:
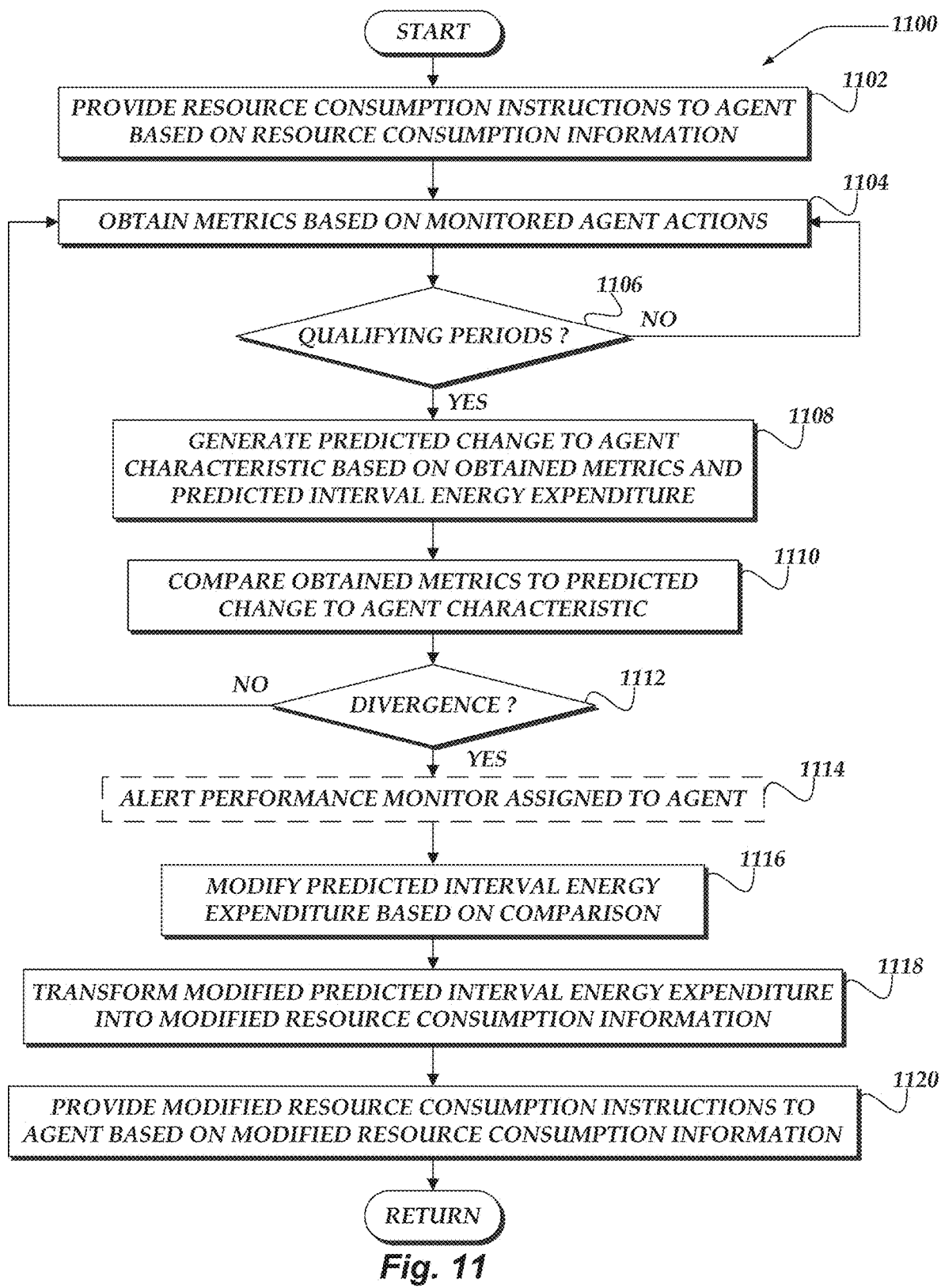
FIG. 11 illustrates a logical flow diagram of an example process for modifying a control session.

FIG. 11 illustrates a logical flow diagram of example process 1100 for modifying a control session. One or more portions of process 1100 may be performed by one or more engines in one or more client computers or network computers (for example: one or more performance tracking engines 218, performance monitor engines 222, or others in one or more client computers 200; one or more resource classification engines 318, resource recipe generation engines 322, consumption control engines 324, metrics analysis engines 326, or others in one or more network computers 300; or others), such as one or more client or network computers associated with or included in one or more agents 402, performance monitors 404, resource consumption control computer 406, or others. In one or more of the various embodiments, one or more portions of process 1100 may correspond to or be included in one or more of blocks 804, 806, 808, 810, 902, 904, 910, 912, 914, 1002, 1008, 1010, 1012, 1014, 1016, or others. In some of the various embodiments, after a start block, at block 1102, one or more resource consumption control instructions may be provided to the agent based on one or more portions of the resource distribution information. In some of the various embodiments, resource consumption instructions may instruct the agent to intake or consume one or more amounts of one or more resources or resource types per interval, intake session, or others.

At block 1104, in one or more of the various embodiments, one or more metrics associated with the control session may be obtained. In some of the various embodiments, the one or more metrics may be based on one or more actions of the agent (for example, one or more actions performed responsive to the one or more resource consumption instructions, resource consumption information, objective performance information, mouse clicks, types of clicks, mouse hover time, opens, visits, refreshes, timing of actions, most-recent login time, quantities of actions, or others). In some embodiments, the one or more metrics may be obtained as the one or more metrics are accumulated or generated, at a predetermined phase in each interval, at a predetermined phase in each period, when the agent connects to a network, or others. In some embodiments, the one or more metrics may indicate the amounts of one or more resource types consumed by the agent in one or more intake sessions, intervals, or others, may indicate feedback associated with one or more activities (for example, one or more weights, performance ratings, material makeups, activity or training intensity, activity or training duration, or others), or others. In some embodiments, one or more portions of the one or more metrics may be provided via a user interface (for example, a web page, application, or others) in various forms, such as email, user interface (UI) notification, instant message, or others. In other embodiments, one or more portions of the one or more metrics may be provided or generated by one or more sensors or sensor interfaces (for example, one or more cameras 240, video interfaces 242, sensor interfaces 262, or others) associated with the agent (for example, one or more sensors or sensor interfaces that are included in client computer 200, that are in communication with client computer 200, or others).

At decision block 1106, in one or more of the various embodiments, if metrics have been obtained for a predetermined number of qualifying periods (for example, two qualifying periods or others) have been obtained, control may flow to block 1108; otherwise, control may flow to block 1104. In some of the various embodiments, a qualifying period may be defined as a set of a predetermined number of back-to-back intervals (for example, 4-7 back-to-back days or others) in which the number of complete intervals meets or exceeds a minimum threshold (for example, four or more complete intervals or others). In some embodiments, a complete interval may be defined as an interval for which resource consumption information has been obtained for each intake during the interval (for example, discretely, in total, or others) and for which objective performance information has been obtained for the interval. In some embodiments, an interval may be indicated as complete based on one or more user inputs confirming that the interval is complete. In some embodiments, a qualifying period may include one or more incomplete intervals (for example, an interval for which resource consumption information has not been obtained for one or more intakes during the interval or for which objective performance information has not been obtained for the interval) between two complete intervals in the qualifying period.

At block 1108, in one or more of the various embodiments, one or more predicted changes to one or more portions of the agent characteristic information may be generated based on one or more obtained metrics and the predicted interval energy expenditure amount. In some of the various embodiments, one or more models, model portions, or sub-models may be selected by employing a similar process as described with regard to one or more of blocks 906, 908, or others, and the one or more selected models, model portions, or sub-models may be employed, executed, or traversed to generate the one or more predicted changes to the one or more portions of the agent characteristics information. In some embodiments, generating the one or more predicted changes may include generating the average expected objective performance per interval, as described with regard to one or more processes of system 400.

At block 1110, in one or more of the various embodiments, one or more obtained metrics may be compared to the one or more predicted changes to the one or more portions of the agent characteristics information. In some of the various embodiments, one or more models, model portions, or sub-models may be selected by employing a similar process as described with regard to one or more of blocks 906, 908, or others, and the one or more selected models, model portions, or sub-models may be employed, executed, or traversed to evaluate the one or more obtained metrics based on the one or more predicted changes. In some embodiments, the comparison or evaluation may include generating a total expected objective performance, a calibration amount, an average calibration amount, or others, as described with regard to one or more processes of system 400. In some embodiments, a calibration amount of zero may represent that the one or more metrics match the one or more predicted changes to the one or more portions of the agent characteristics information, and non-zero calibration amount may indicate that one or more measured objective performances in one or more metrics diverged from the one or more predicted changes to the one or more agent characteristics.

At decision block 1112, in one or more of the various embodiments, if one or more metrics diverge from the one or more predicted changes to the one or more portions of the agent characteristics information, control may flow to block 1114; otherwise, control may return to block 1104 because the system is appropriately calibrated.

At block 1114, in one or more of the various embodiments, one or more alerts may be provided to one or more performance monitors assigned to the agent to notify the one or more performance monitors that the agent's performance has diverged from the agent's expected performance. In some of the various embodiments, the one or more performance monitors may be assigned to the agent as described with regard to one or more processes of system 400. In some embodiments, the one or more performance agents may communicate with the agent or one or more entities that supervise the agent to obtain further information associated with the divergence. In some embodiments, the one or more performance agents may modify one or more components of one or more models based on the divergence to calibrate the one or more resource consumption control computers and improve performance criterion. Block 1114 may be optional because one or more performance monitors may not yet or may not be assigned to the agent.

At block 1116, in one or more of the various embodiments, the predicted interval energy expenditure amount may be modified based on the evaluation of the comparison of the one or more obtained metrics to the one or more predicted changes to the one or more portions of the agent characteristics information. In some of the various embodiments, the predicted interval energy expenditure amount may be modified based on the calibration amount, average calibration amount, or others as described with regard to one or more processes of system 400.

At block 1118, in one or more of the various embodiments, the modified predicted interval energy expenditure amount may be transformed into modified resource consumption information. In some of the various embodiments, the modified resource consumption information may be generated by executing one or more portions of one or more of blocks 1008, 1010, 1012, 1014, or others based on the modified predicted interval energy expenditure amount instead of the predicted interval energy expenditure amount.

At block 1120, in one or more of the various embodiments, one or more modified resource consumption instructions may be provided to the agent based on one or more portions of the modified resource consumption information. In some of the various embodiments, the one or more modified resource consumption instructions may be provided to the agent as described with regard to block 1016 based on one or more portions of the modified resource consumption information instead of the resource consumption information.

In some embodiments, process 1100 may continue operating until the control session terminates or a user configures process 1100 to terminate operation. Next, control may be returned to a calling process.

Figure 12:
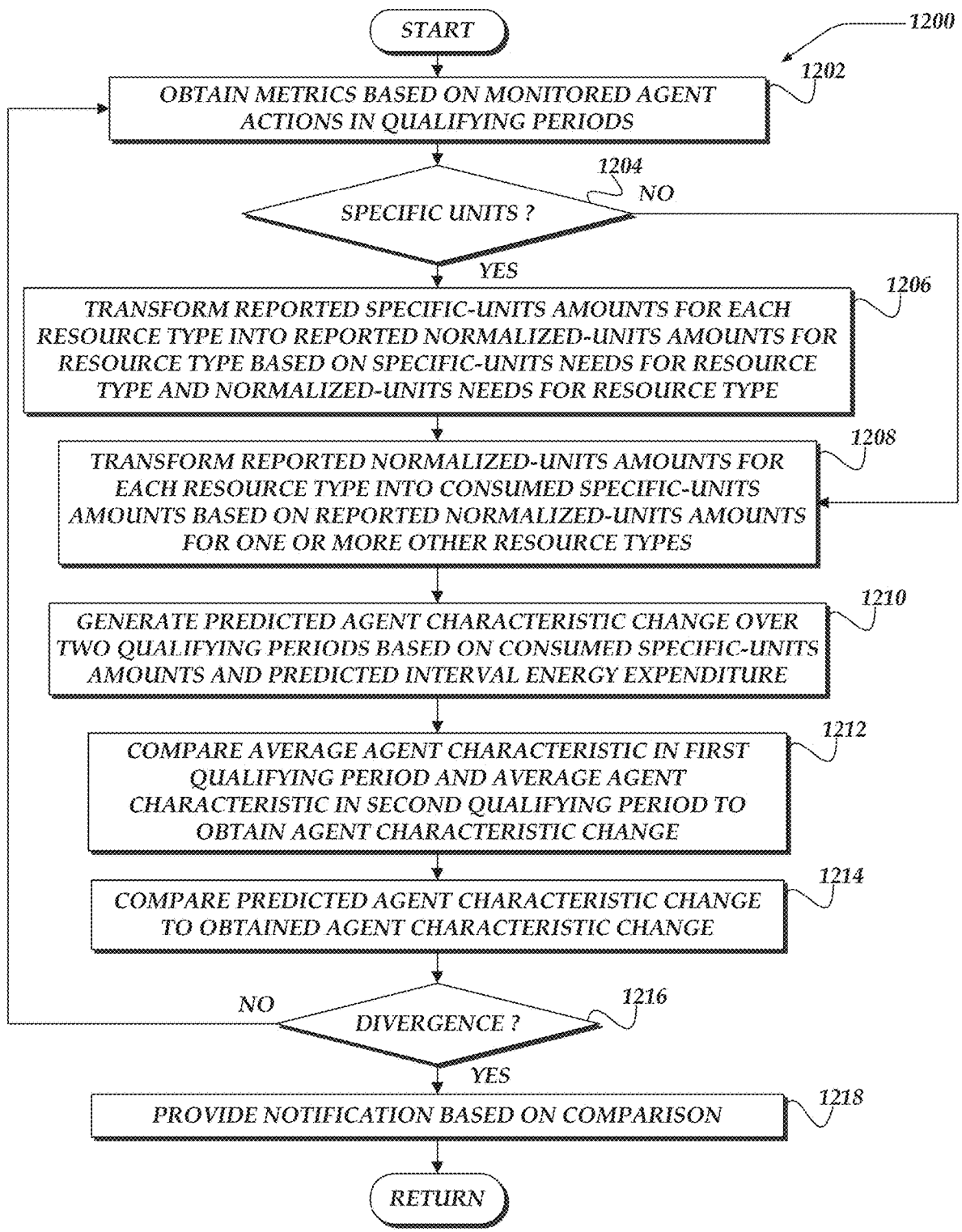
FIG. 12 shows a logical flowchart of an example process for evaluating obtained metrics associated with a control session.

FIG. 12 shows a logical flowchart of example process 1200 for evaluating obtained metrics associated with a control session. One or more portions of process 1200 may be performed by one or more engines in one or more client computers or network computers (for example: one or more performance tracking engines 218, performance monitor engines 222, or others in one or more client computers 200; one or more resource classification engines 318, resource recipe generation engines 322, consumption control engines 324, metrics analysis engines 326, or others in one or more network computers 300; or others), such as one or more client or network computers associated with or included in one or more agents 402, performance monitors 404, resource consumption control computer 406, or others. In one or more of the various embodiments, one or more portions of process 1200 may correspond to or be included in one or more of blocks 804, 806, 808, 810, 902, 904, 910, 912, 914, 1002, 1008, 1010, 1012, 1014, 1016, 1104, 1108, 1110, 1112, 1114, or others. In some of the various embodiments, after a start block, at block 1202, one or more metrics associated with the control session may be obtained. In some embodiments, the one or more metrics may be based on one or more actions of the agent (for example, one or more actions performed responsive to the one or more resource consumption instructions, resource consumption information, objective performance information, mouse clicks, types of clicks, mouse hover time, opens, visits, refreshes, timing of actions, most-recent login time, quantities of actions, or others). In some embodiments, the one or more metrics may be obtained as the one or more metrics are accumulated or generated, at a predetermined phase in each interval, at a predetermined phase in each period, when the agent connects to a network, or others. In some embodiments, the one or more metrics may indicate the amounts of one or more resource types consumed by the agent in one or more intake sessions, intervals, or others, may indicate feedback associated with one or more activities (for example, one or more weights, performance ratings, material makeups, activity or training intensity, activity or training duration, or others), or others. In some embodiments, one or more portions of the one or more metrics may be provided via a user interface (for example, a web page, application, or others) in various forms, such as email, user interface (UI) notification, instant message, or others. In other embodiments, one or more portions of the one or more metrics may be provided or generated by one or more sensors or sensor interfaces (for example, one or more cameras 240, video interfaces 242, sensor interfaces 262, or others) associated with the agent (for example, one or more sensors or sensor interfaces that are included in client computer 200, that are in communication with client computer 200, or others).

In one or more of the various embodiments, the one or more metrics may include resource consumption information that may include reported amounts of specific units, normalized units, or others for each consumed resource type. In some of the various embodiments, the reported amounts of specific or normalized units for each consumed resource type may indicate the reported amounts of specific or normalized units for each consumed resource type over the entirety of the complete intervals in the qualifying periods, over the entirety of the complete intervals in each qualifying period, over each complete interval, over each intake session in each complete interval, or others. Accordingly, in some embodiments, one or more resource consumption control computers may facilitate the agent providing one or more portions of one or more metrics in specific units and another one or more portions of the one or more metrics in normalized units to alleviate the agent of a requirement to transform specific units into normalized units or normalized units into specific units, thereby improving responsiveness of the system to the agent.

At decision block 1204, in one or more of the various embodiments, if one or more portions of the one or more metrics include one or more amounts in specific units, control may flow to block 1206; otherwise, control may flow to block 1208.

At block 1206, in one or more of the various embodiments, the reported amounts of specific units for each consumed resource type may be transformed into amounts of normalized units reportedly consumed on average per interval for the consumed resource type based on a specific-units needs amounts for the consumed resource type and a normalized-units needs amount for the resource type (for example, needs amounts generated as described with regard to blocks 1010, 1012, or others). In some of the various embodiments, reported amounts of specific or normalized units consumed on average per interval may be generated based on the reported amounts of specific or normalized units consumed for each consumed resource type and the number of complete intervals. For example, the reported amounts of specific or normalized units consumed for each consumed resource type over the entirety of the complete intervals in the qualifying periods may be divided by the number of complete intervals in the qualifying periods to generate the reported amounts of specific or normalized units consumed on average per interval.

In one or more of the various embodiments, the reported amounts of specific or normalized units consumed on average per interval for each consumed resource type may be transformed into total reported amounts of normalized units consumed on average per interval based on the specific-units needs amounts for each resource type (for example: the average-interval specific-units needs amount for the resource type generated at block 1010 for the qualifying period or the complete intervals; the particular-interval specific-units needs amounts for the resource type generated at block 1010 for the qualifying period or the complete intervals; or others) and the normalized-units needs amounts for each consumed resource type (for example: the average-interval normalized-units needs amount for the resource type generated at block 1012 for the qualifying period or the complete intervals; the particular-interval normalized-units needs amount for the resource type generated at block 1012 for the qualifying period or the complete intervals; or others). In some of the various embodiments, the reported amounts of specific units consumed on average per interval for a consumed resource type may be divided by a ratio of the specific-units needs amount for the consumed resource type to the normalized-units needs amount for the consumed resource type (for example, the specific-units needs amount for the consumed resource type divided by the normalized-units needs amount for the consumed resource type or others), and the result may be added to the reported amounts of normalized units consumed on average per interval for the consumed resource type to generate the total reported amounts of normalized units consumed on average per interval for the consumed resource type. In some embodiments, because the specific-units needs amount or the normalized-units needs amount for each of one or more resource types may be different for different intervals, an average of the specific-units needs amounts for the resource type for the complete intervals in the qualifying period and the average of the normalized-units needs amounts for the resource type for the complete intervals in the qualifying period may be employed to generate the ratio. In some embodiments, the total amounts of normalized units reportedly consumed on average per interval may be generated for each consumed resource type.

At block 1208, in one or more of the various embodiments, the total amounts of normalized units reportedly consumed on average per interval for each consumed resource type may be transformed into total amounts of specific units reportedly consumed on average per interval for each consumed resource type based on the amounts of normalized units reportedly consumed on average per interval for one or more other consumed resource types. In some of the various embodiments, the total amounts of normalized units reportedly consumed on average per interval for a consumed resource type may be multiplied by a conversion factor associated with the consumed resource type (for example, the total number of reportedly consumed carbohydrate servings multiplied by the average number of grams expected to be included in a serving of carbohydrates or others), and the result may be summed with the number of specific units for the consumed resource type that are expected to be included in the total amounts of normalized units reportedly consumed on average per interval for each other consumed resource type (for example, the number expected based on one or more resource models 420 in resource model repository 418, such as resource model 700), thereby facilitating generating total amounts of specific units reportedly consumed on average per interval for the consumed resource type. In other embodiments, the amounts of normalized units reportedly consumed on average per interval for a consumed resource type may be multiplied by a conversion factor associated with the consumed resource type and summed with the amounts of specific units reportedly consumed on average per interval for the consumed resource type, and the result may be summed with the number of specific units for the consumed resource type that are expected to be included in the total amounts of normalized units reportedly consumed on average per interval for each other consumed resource type, thereby facilitating generating the total amounts of specific units reportedly consumed on average per interval for the consumed resource type. In some embodiments, the total amounts of specific units reportedly consumed on average per interval may be generated for each consumed resource type.

At block 1210, in one or more of the various embodiments, a predicted change in one or more agent characteristics over two or more qualifying periods may be generated based on a predicted energy expenditure amount on average per interval and the total amounts of specific units reportedly consumed on average per interval for the multiple resource types. In some of the various embodiments, the total amounts of specific units reportedly consumed on average per interval for each of the consumed resource types may be multiplied by the amount of energy expected to be included in each specific unit of the consumed resource type to generate an amount of energy reportedly consumed on average per interval for each of the consumed resource types, and the reported amounts of energy of the consumed resource types may be summed to provide a total amount of energy reportedly consumed on average per interval.

In one or more of the various embodiments, an average expected objective performance per interval (for example, an average expected weight loss per day, an average expected weight gain per day, or others) based on the predicted interval energy expenditure amount, the amount of energy reportedly consumed on average per interval or the consumption result, the number of complete intervals, the phase in each period at which each complete interval occurs, or others. In some of the various embodiments, the predicted interval energy expenditure amount may be subtracted from the amount of energy reportedly consumed on average per interval to generate a reported energy divergence amount on average per interval. In some embodiments, the average energy divergence amount per interval may be transformed into an average expected objective performance per interval (as measured in the units employed for the objective performance information, such as pounds, kilograms, a scaled rating such as one to five, or others). For example, the average energy divergence amount per interval may be measured in calories, and the average energy divergence amount per interval may be divided by 7,700 to transform the average energy divergence amount per interval into the average expected objective performance per interval (for example, weight loss per interval or others) as measured in kilograms.

In one or more of the various embodiments, an average complete interval may be generated for each qualifying period based on the phase in each qualifying period at which each complete interval occurs. For example, for a qualifying period of a week that employs intervals of days with the qualifying period starting on a Wednesday, Wednesday may be interval one, Thursday may be interval two, Friday may be interval three, Saturday may be interval four, Sunday may be interval five, Monday may be interval six, Tuesday may be interval seven, and, with complete intervals of Wednesday, Friday, Saturday, and Tuesday, the average complete interval may be 3.75 ((1+3+4+7)/4=3.75). In some embodiments, the number of intervals between the average complete interval of the most recent qualifying period and the average complete interval of the first qualifying period may be counted, including one of the first or most recent average complete interval. For example, when the most recent qualifying period is the week immediately following the first qualifying period and both the most recent and the first qualifying periods have average complete intervals of 3.75, the number of intervals between the average complete intervals may be 7. In some embodiments, the average expected objective performance per interval may be multiplied by the number of intervals between the average complete intervals to generate the predicted change in the one or more agent characteristics over the qualifying periods.

At block 1212, in one or more of the various embodiments, one or more average values for one or more agent characteristics in the first qualifying period may be compared to one or more average values for one or more agent characteristics in the most recent qualifying period to generate one or more obtained changes in one or more agent characteristics. In some of the various embodiments, the one or more metrics may include objective performance information (for example, the weight of the agent as measured each day in a week or others) for each complete interval in each qualifying period. In some embodiments, the objective performance information for the intervals in a qualifying period may be averaged to generate an average objective performance for the qualifying period. For example, the sum of the weight of the agent at each complete interval in a qualifying period may be divided by the number of complete intervals in the qualifying period to generate the average objective performance for the qualifying period. In some embodiments, the average objective performance for the first qualifying period being evaluated (for example, the first-in-time qualifying period being evaluated or others) may be generated for each qualifying period, the first-in-time and most recent of the qualifying periods being evaluated, or others. In some embodiments, the average objective performance for the first qualifying period may be subtracted from the average objective performance of the most recent qualifying period to generate an objective performance change over the qualifying periods being evaluated.

At block 1214, in one or more of the various embodiments, the predicted change in the one or more agent characteristics over the qualifying periods may be compared to the one or more obtained changes in the one or more agent characteristics. In some of the various embodiments, the predicted change in the one or more agent characteristics over the qualifying periods being evaluated may be subtracted from the objective performance change over the qualifying periods being evaluated to generate an objective performance divergence. In some embodiments, the objective performance divergence may be divided by the number of intervals between the average complete intervals for the most recent period and the average complete intervals in the first period to generate an objective performance divergence on average per interval. In some embodiments, the objective performance divergence on average per interval may be transformed into a calibration amount (as measured in the units employed for the predicted interval energy expenditure amount, such as calories or others). For example, the objective performance divergence on average per interval may be measured in kilograms, and the objective performance divergence on average per interval may be divided by 7,700 to generate the calibration amount as measured in calories. In other embodiments, the objective performance divergence on average per interval may be summed with one or more previously generated objective performance divergences on average per interval (for example, up to a predetermined number of previous objective performance divergences that may have been generated employing similar processes as described with regard to the objective performance divergence on average per interval based on qualifying periods that may be prior to the most recent qualifying period, such as three of the immediately preceding objective performance divergences or others), and the sum may be divided by the number of objective performance divergences being evaluated (including both the one or more previous objective performance divergences and the objective performance divergence) to generate an average objective performance divergence for a trailing window defined by the number of previous objective performance divergences employed, with the calibration amount being generated by dividing the average objective divergence by 7,700 or other transformation amounts. In some embodiments, a calibration amount of zero may represent that the objective performance information (or trailing window of the objective performance information) matches the one or more predicted changes to the one or more portions of the agent characteristics information, and non-zero calibration amount may indicate that the objective performance information (or trailing window of the objective performance information) diverged from the one or more predicted changes to the one or more agent characteristics.

At decision block 1216, in one or more of the various embodiments, if the objective performance information (or trailing window of the objective performance information) diverged from the one or more predicted changes to the one or more agent characteristics, control may flow to block 1218; otherwise, control may flow to block 1202 to continue monitoring the agent in the control session.

At block 1218, in one or more of the various embodiments, one or more notifications may be provided based on the divergence detected in the comparative evaluation of the objective performance information (or trailing window of the objective performance information) and the one or more predicted changes to the one or more agent characteristics. In some of the various embodiments, the one or more notifications may be provided to one or more performance monitors assigned to the agent, entities that supervise the agent, engines tasked with modifying the control session, the agent, or others.

In some embodiments, process 1200 may continue operating until the control session terminates or a user configures process 1200 to terminate operation. Next, control may be returned to a calling process.

Figure 13:
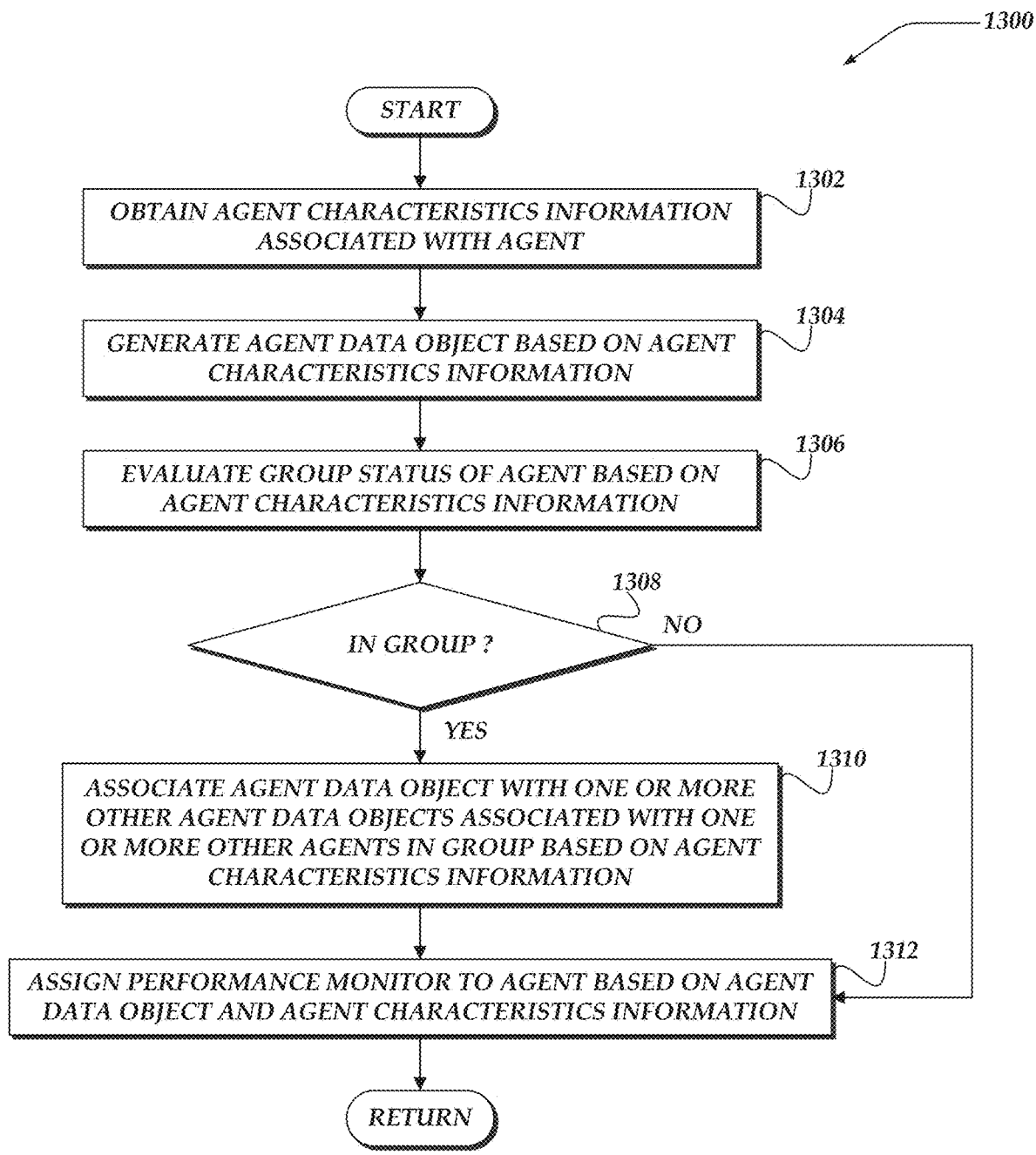
FIG. 13 illustrates a logical flow diagram of an example process for assigning a performance monitor to an agent.

FIG. 13 illustrates a logical flow diagram of example process 1300 for assigning a performance monitor to an agent. One or more portions of process 1300 may be performed by one or more engines in one or more client computers or network computers (for example: one or more performance tracking engines 218, performance monitor engines 222, or others in one or more client computers 200; one or more resource classification engines 318, resource recipe generation engines 322, consumption control engines 324, metrics analysis engines 326, or others in one or more network computers 300; or others), such as one or more client or network computers associated with or included in one or more agents 402, performance monitors 404, resource consumption control computer 406, or others. In one or more of the various embodiments, one or more portions of process 1100 may correspond to or be included in one or more of blocks 802, 902, 904, 1002, or others. In some of the various embodiments, after a start block, at block 1302, agent characteristics information associated with an agent may be obtained to initialize or launch a control session, such as a control session to control resource consumption by an agent. In some embodiments, the agent, an entity that supervises the agent, a performance monitor temporarily assigned to the agent, or others may communicate one or more portions of the agent characteristics information over one or more networks to one or more resource consumption control computers 406. In some embodiments, one or more portions of the agent characteristics information may be provided via a user interface (for example, a web page, application, or others) in various forms, such as email, user interface (UI) notification, instant message, or others. In other embodiments, one or more portions of the agent characteristics information may be provided or generated by one or more sensors or sensor interfaces (for example, one or more cameras 240, video interfaces 242, sensor interfaces 262, or others) associated with the agent (for example, one or more sensors or sensor interfaces that are included in client computer 200, that are in communication with client computer 200, or others).

At block 1304, in one or more of the various embodiments, one or more agent data objects associated with the agent may be generated based on one or more portions of the agent characterization information. In some of the various embodiments, the one or more agent data objects may be generated or populated as described with regard to one or more processes of system 400, one or more processes described with regard to one or more data structures described with regard to FIG. 6 or 7, block 904, or others.

At block 1306, in one or more of the various embodiments, a group status of the agent may be evaluated based on one or more portions of the agent characterization information. In some of the various embodiments, one or more portions of the agent characteristics information may be provided in a comma-separated values (CSV) file that includes one or more portions of agent characteristics information associated with multiple agents in one or more groups. For example, an entity that supervises the agent may provide a CSV file that includes a roster of the supervised agents in one or more groups or sub-groups. Accordingly, in some embodiments, the file may indicate group status information associated with the agent. In other embodiments, the agent's email address may be evaluated and compared to a list or parsed to generate the group status information.

At decision block 1308, in one or more of the various embodiments, if the group status of the agent indicates that the agent is part of or associated with one or more groups or sub-groups, control may flow to block 1310; otherwise, control may flow to block 1312.

At block 1310, in one or more of the various embodiments, the one or more agent data objects may be associated with one or more other agent data objects that are associated with one or more other agents in the one or more groups or sub-groups to which the agent belongs or with which the agent is associated based on the agent characteristics information. In some of the various embodiments, the one or more agent data objects may include one or more group or sub-group fields that may be populated with one or more identifiers (for example, self-referential identifiers, referential identifiers, or others) that indicate the group status, the one or more groups or sub-groups, or the other agents.

At block 1312, in one or more of the various embodiments, one or more performance monitors may be assigned to the agent based on the one or more agent data objects and one or more portions of the agent characteristics information. In some of the various embodiments, if the agent is associated with one or more groups or sub-groups, one or more performance monitors may be assigned to each agent in the one or more groups or sub-groups, thereby facilitating horizontal access to information. In some embodiments, if the agent is not associated with one or more groups or sub-groups, one or more performance monitors may be assigned to the agent arbitrarily, based on geographical or logical region or territory, based on activity type, agent type, objectives, or others.

In some embodiments, process 1300 may continue operating until the control session terminates, the control session has fully launched, or a user configures process 1300 to terminate operation. Next, control may be returned to a calling process.

Figure 14:
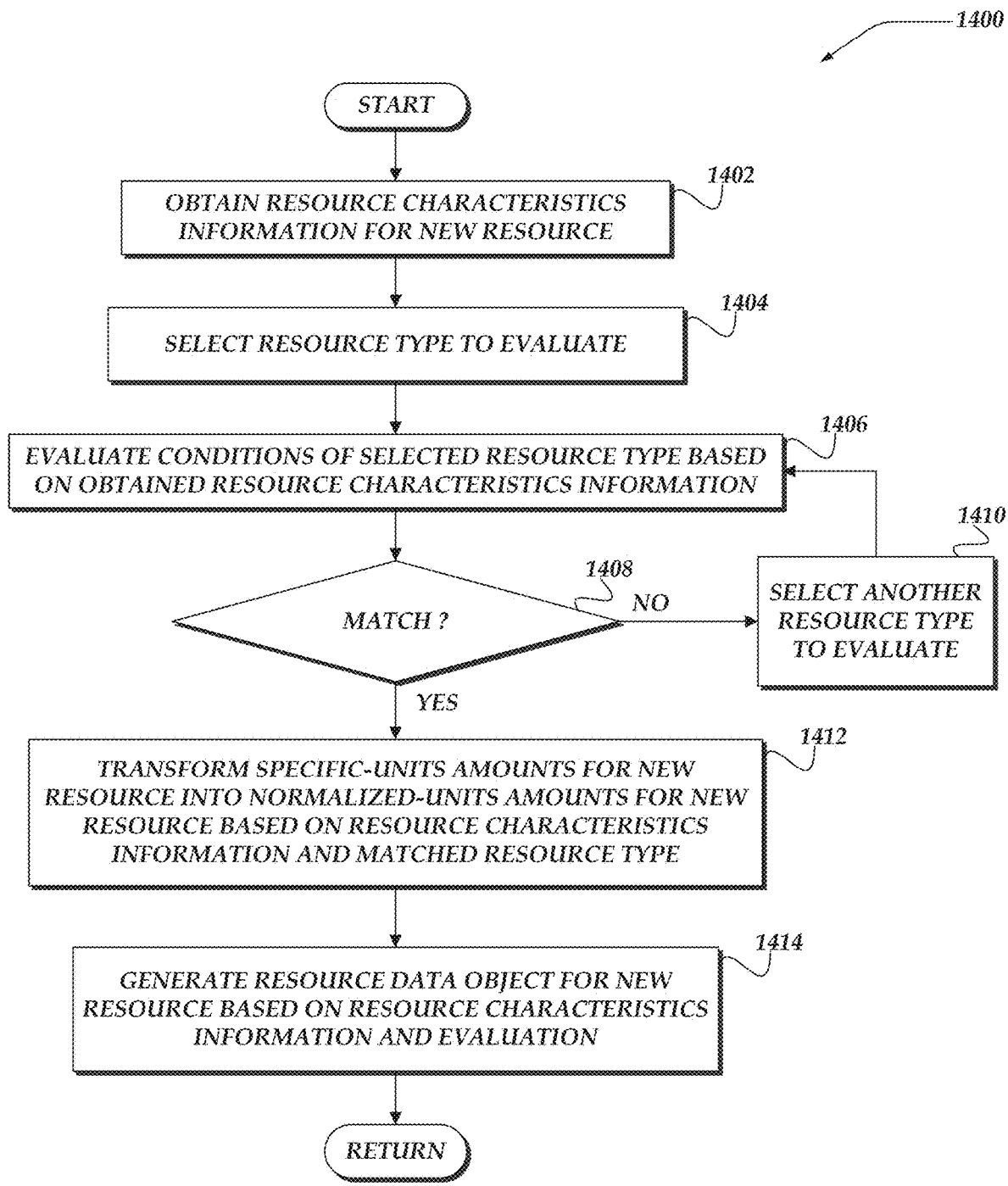
FIG. 14 shows a logical flowchart of an example process for generating a resource data object for a new resource.

FIG. 14 shows a logical flowchart of example process 1400 for generating a resource data object for a new resource. One or more portions of process 1400 may be performed by one or more engines in one or more client computers or network computers (for example: one or more performance tracking engines 218, performance monitor engines 222, or others in one or more client computers 200; one or more resource classification engines 318, resource recipe generation engines 322, consumption control engines 324, metrics analysis engines 326, or others in one or more network computers 300; or others), such as one or more client or network computers associated with or included in one or more agents 402, performance monitors 404, resource consumption control computer 406, or others. In one or more of the various embodiments, after a start block, at block 1402, resource characteristics information may be obtained for a new resource. In some of the various embodiments, an agent, an entity that supervises the agent, a performance monitor, administrator, or others may communicate one or more portions of the resource characteristics information over one or more networks to one or more resource consumption control computers 406. In some embodiments, one or more portions of the resource characteristics information may be provided via a user interface (for example, a web page, application, or others) in various forms, such as email, user interface (UI) notification, instant message, or others. In other embodiments, one or more portions of the resource characteristics information may be provided or generated by one or more sensors or sensor interfaces (for example, one or more cameras 240, video interfaces 242, sensor interfaces 262, or others). In some embodiments, the resource characteristics information may include one or more energy sources (for example, protein, carbohydrates, fats, or others) in terms of percentages (for example, a given amount of a resource may derive various percentages of its energy from different energy sources) or specific units (for example, grams or others).

At block 1404, in one or more of the various embodiments, a resource type to evaluate based on the resource characteristics information may be selected. In some of the various embodiments, the resource type selected may be arbitrary, based on a predetermined order, based on a best preliminary guess, or others.

At block 1406, in one or more of the various embodiments, one or more conditions of the selected resource type may be evaluated based on one or more portions of the resource characteristics information. In some of the various embodiments, each resource type may have one or more conditions that, if satisfied, indicate that the one or more portions of the resource characteristics information may match with the resource type. In some embodiments, a condition may include that the one or more portions of the resource characteristics information has not matched with a higher-ranking resource type in a hierarchy of resource types. For example, vegetables may have highest priority, carbohydrates may have the second highest priority, proteins may have the third highest priority, and fats may have the lowest priority. Accordingly, in some embodiments, a resource that satisfies conditions of multiple resource types may only match with the satisfied resource type that has the highest priority. In some embodiments, a condition may include most of the percentage of the one or more energy sources of the resource being the resource type (for example, the resource derives a greater percentage of its energy from the evaluated resource type than the percentage of its energy derived from each other resource type). In some embodiments, a condition may include the highest specific units amount of the one or more energy sources of the resource being the resource type. In some embodiments, one or more conditions must be satisfied, one or more of multiple conditions must be satisfied, or others.

At decision block 1408, in one or more of the various embodiments, if the one or more portions of the resource characteristics information match with the selected resource type, control may flow to block 1412; otherwise, control may flow to block 1410.

At block 1410, in one or more of the various embodiments, another resource type is selected to evaluate. In some of the various embodiments, the resource type selected may be arbitrary, based on a predetermined order, based on a best preliminary guess, or others.

At block 1412, in one or more of the various embodiments, specific-units amounts for the resource may be transformed into normalized-units amounts for the new resource based on one or more portions of the resource characteristics information and the matched resource type. In some of the various embodiments, an expected number of normalized units per a predetermined number of specific units may be based on historical analysis provided by a third party, average sample analysis, user input, or others. In some embodiments, the energy source information may be employed to generate the number of normalized units per number of specific units. In other embodiments, the number of normalized units per number of specific units may be standard based on the average or expected number for the matched resource type (for example, 25 grams of a resource that is a resource type of protein may equate to one serving of protein or others).

At block 1414, in one or more of the various embodiments, one or more resource data objects may be generated for the resource based on one or more portions of the resource characteristics information and the evaluation. In some of the various embodiments, the one or more resource data objects may be generated or populated employing one or more similar processes as described with regard to one or more processes of system 400, one or more processes described with regard to one or more data structures described with regard to FIG. 6 or 7, or others. For example, resource model 700 may be appended with the data structure, and the data structure may be populated with the number of normalized units, the number of specified units per the number of normalized units, the resource name, one or more characteristics (for example, the resource type, the energy sources in terms of percentages or specific units, or others).

In some embodiments, process 1400 may continue operating until the control session terminates or a user configures process 1400 to terminate operation. Next, control may be returned to a calling process.

Figure 15:
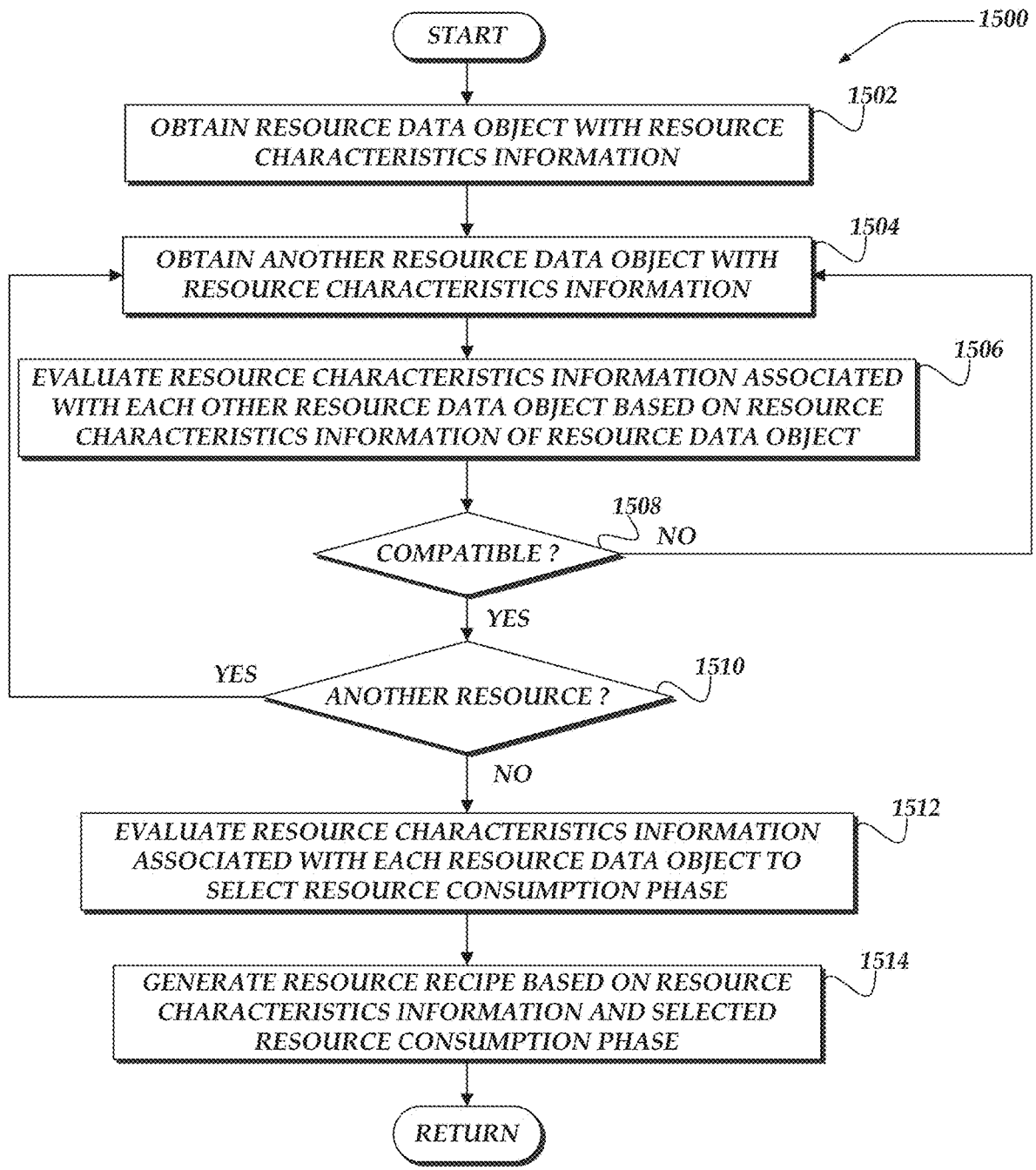
FIG. 15 illustrates a logical flow diagram of an example process for generating a resource recipe.

FIG. 15 illustrates a logical flow diagram of example process 1500 for generating a resource recipe. One or more portions of process 1500 may be performed by one or more engines in one or more client computers or network computers (for example: one or more performance tracking engines 218, performance monitor engines 222, or others in one or more client computers 200; one or more resource classification engines 318, resource recipe generation engines 322, consumption control engines 324, metrics analysis engines 326, or others in one or more network computers 300; or others), such as one or more client or network computers associated with or included in one or more agents 402, performance monitors 404, resource consumption control computer 406, or others. In one or more of the various embodiments, after a start block, at block 1502, one or more resource data objects having resource characteristics information associated with a resource may be obtained (for example, one or more resource data structures in resource model 700 or others).

At block 1504, in one or more of the various embodiments, another one or more resource data objects having resource characteristics information associated with another resource may be obtained (for example, another one or more data structures in resource model 700 or others).

At block 1506, in one or more of the various embodiments, one or more portions of the resource characteristics information of the one or more other resource data objects may be evaluated based on one or more portions of the resource characteristics information of the one or more resource data objects. In some of the various embodiments, the resource and the other resource may be compatible with each other if one or more portions of their respective resource characteristic information overlaps, matches, satisfies one or more conditions, fails to overlap, fails to match, or others. For example, the resource and the other resource may be compatible with each other if their respective resource characteristic information indicates that they may both be breakfast foods, if only one of them takes a large amount of time or effort to prepare, if they are of different resource types, if their combination correlates to a predicted high likelihood of agent or control session success, or others. In some embodiments, compatibility may vary based on geographic region for which the recipe is intended.

At decision block 1508, in one or more of the various embodiments, if the resource and the other resource are compatible with each other, control may flow to decision block 1510; otherwise, control may flow to block 1504 to substitute one or more of the resource or the other resource with a further resource to evaluate.

At decision block 1510, in one or more of the various embodiments, if the recipe has enough resources, control may flow to block 1512; otherwise, control may flow to block 1504 to select a further resource to evaluate in combination with the resource and the other resource. In some of the various embodiments, one or more configuration files, rules, custom scripts, or others may define one or more thresholds for a minimum number of resources to include in a recipe based on one or more factors, such as whether the recipe is a snack or a meal recipe, the type of snack or meal (for example, standard, pre-workout, post-workout, quick preparation, normal preparation, gourmet preparation, or others).

At block 1512, in one or more of the various embodiments, one or more portions of the resource characteristics information of each resource in the recipe may be evaluated to select one or more resource consumption phases to associate with the recipe. In some of the various embodiments, each phase associated with each of the resources in the recipe may be selected. In some embodiments, one or more phases associated with the recipe may vary based on geographic region for which the recipe is intended.

At block 1514, in one or more of the various embodiments, one or more resource recipes may be generated based on one or more portions of the resource characteristics information associated with the selected resources and based on the one or more selected resource consumption phases. In some of the various embodiments, generating the recipe may include generating or populating one or more data objects associated with the recipe. In some embodiments, the one or more recipe data objects may be generated or populated employing one or more similar processes as described with regard to one or more processes of system 400, one or more processes described with regard to one or more data structures described with regard to FIG. 6 or 7, or others. In some embodiments, one or more attributes of the one or more recipe data objects may indicate one or more restrictions (for example, allergies, dietary choices or restrictions, intake type, geographical associations, intake phases, or others).

In some embodiments, process 1500 may continue operating until a control session terminates, all combinations of resources have been evaluated, until a threshold number of recipes have been generated, or a user configures process 1500 to terminate operation. Next, control may be returned to a calling process.

It will be understood that each block of the flowchart illustration, and combinations of blocks in the flowchart illustration, can be implemented by computer program instructions. These program instructions may be provided to one or more processors to produce a machine, such that the instructions, which execute on the one or more processors, create means for implementing the actions specified in the flowchart block or blocks. The computer program instructions may be executed by the one or more processors to cause a series of operational steps to be performed by the one or more processors to produce a computer-implemented process such that the instructions, which execute on the one or more processors to provide steps for implementing the actions specified in the flowchart block or blocks. The computer program instructions may also cause at least some of the operational steps shown in the blocks of the flowchart to be performed in parallel or concurrently by the one or more processors or one or more computers. Moreover, some of the steps may also be performed across more than one processor or computer. In addition, one or more blocks or combinations of blocks in the flowchart illustration may also be performed concurrently with other blocks or combinations of blocks, or even in a different sequence than illustrated without departing from the scope or spirit of the invention.

Accordingly, blocks of the flowchart illustration support combinations of means for performing the specified actions, combinations of steps for performing the specified actions and program instruction means for performing the specified actions. It will also be understood that each block of the flowchart illustration, and combinations of blocks in the flowchart illustration, can be implemented by special purpose hardware based systems, which perform the specified actions or steps, or combinations of special purpose hardware and computer instructions. The foregoing example should not be construed as limiting or exhaustive, but rather, an illustrative use case to show an embodiment of one or more of the various embodiments of the invention. Moreover, one or more portions of one or more embodiments may be modified without departing from the invention. For example, an agent age below a threshold may indicate that the agent is in a development phase that should be evaluated in addition to the performance objectives, such as employing one or more models, model portions, sub-models, or others associated with predicted development needs in addition or alternative to one or more predicted interval energy expenditure amounts (for example, employing one or more similar processes as described with regard to the predicted energy consumption needs yet with the one or more additional or alternative models, model portions, sub-models, or others).

Further, in one or more embodiments (not shown in the figures), the logic in the illustrative flowcharts may be executed using one or more embedded logic hardware devices instead of one or more CPUs, such as an Application Specific Integrated Circuits (ASICs), Field Programmable Gate Arrays (FPGAs), Programmable Array Logic chips (PALs), or others. The embedded one or more logic hardware devices may directly execute their embedded logic to perform actions. In at least one embodiment, one or more microcontrollers may be arranged as system-on-a-chip (SOCs) to directly execute their own locally embedded logic to perform actions and access their own internal memory and their own external Input and Output Interfaces (e.g., hardware pins or wireless transceivers) to perform actions described herein.

What is claimed as new and desired to be protected by Letters Patent of the United States is:

1. A method for improving performance criterion in a control session, wherein one or more processors in a network computer perform the method by executing computer readable instructions, the method comprising:

obtaining characteristics information associated with an agent;

logically associating the characteristics information with the agent in an agent repository, the agent repository logically associating characteristics information and metrics of a plurality of agents with respective ones of the plurality of agents, the agent repository logically associating the plurality of agents with different control sessions;

generating one or more outputs based on the characteristics information of the agent and a performance model, wherein the one or more outputs include a predicted expenditure amount, the predicted expenditure amount representing an amount of energy that the agent is predicted to expend per interval;

generating a consumption instruction to control resource consumption by the agent based on the predicted expenditure amount;

transmitting the consumption instruction to a client computer associated with the agent, the client computer including a display, a sensor or sensor interface coupled to at least one of a camera, a scale, an accelerometer, or a global positioning system (GPS) receiver, to receive metrics associated with the agent from the sensor or sensor interface, and one or more transceivers that communicate over the network;

receiving, from the client computer, metrics associated with the agent for a first period, the metrics for the first period being based on the consumption instruction and a monitoring of the agent, the monitoring of the agent including at least one of capturing an image by the camera, weighing a weight of the agent using the scale, detecting a number of steps of the agent using the accelerometer, determining a change in determined physical locations of the client computer or the agent received from the GPS receiver;

sending information corresponding to at least one of the image, the weight, the number of steps, or the change in determined physical locations to a resource consumption control computer to generate the one or more values that represent one or more resource types of resource amounts consumed by the agent;

collecting, from the sensor or sensor interface, one or more portions of the metrics for the first period, the metrics for the first period being associated with one or more intervals in a plurality of intervals in the first period, the one or more intervals in the first period being associated with a first phase in the first period, the metrics for the first period including a first reportedly consumed amount of normalized units of a first resource type and a second reportedly consumed amount of normalized units of a second resource type;

receiving, from the client computer, metrics associated with the agent for a second period, the metrics for the second period being based on the consumption instruction and the monitoring of the agent including collecting, by the sensor or sensor interface, one or more portions of the metrics for the second period, the metrics for the second period being associated with one or more intervals in a plurality of intervals in the second period, the one or more intervals in the second period being associated with a second phase in the second period;

logically associating the metrics for the first period and the metrics for the second period with the agent in the agent repository;

transforming the first reportedly consumed amount of normalized units of the first resource type into a first reportedly consumed amount of specific units of the first resource type;

transforming the second reportedly consumed amount of normalized units of the second resource type into a second reportedly consumed amount of specific units of the second resource type based on the first reportedly consumed amount of normalized units of the first resource type;

transforming the first reportedly consumed amount of specific units of the first resource type and the second reportedly consumed amount of specific units of the second resource type into a first total reportedly consumed amount;

generating an expected objective performance based on at least one portion of the obtained metrics for the first period including the first total reportedly consumed amount, at least one portion of the obtained metrics for the second period, and a duration between the first phase in the first period and the second phase in the second period;

comparing the expected objective performance to a difference between the one or more portions of the obtained metrics for the first period and the one or more portions of the obtained metrics for the second period;

modifying the predicted expenditure amount based on the comparison to increase a correlation between the one or more outputs and the obtained metrics for the second period;

synchronizing the client computer with the resource consumption control computer after the client computer rejoins the network, wherein the resource consumption control computer provides the client computer at least updated characteristics information based on a comparison between a first timestamp associated with a most-recent update of the characteristics information at the client computer with a second timestamp associated with the updated characteristics information;

generating a modified consumption instruction to control the resource consumption by the agent based on the modified predicted expenditure amount; and transmitting the modified consumption instruction to the client computer for visual representation on the display.

2. The method of claim 1, wherein generating the expected objective performance comprises:

generating an expected objective performance per interval based on one or more portions of the obtained metrics for the first period and one or more portions of the obtained metrics for the second period; and generating the expected objective performance based on the expected objective performance per interval and a number of intervals between the first phase in the first period and the second phase in the second period.

3. The method of claim 1, wherein modifying the predicted expenditure amount comprises:

generating an objective performance divergence per interval based on the comparison; and modifying the predicted expenditure amount by a value of the objective performance divergence per interval.

4. The method of claim 1, wherein receiving the metrics for the first period comprises:

determining that the one or more intervals in the first period are one or more complete intervals in the first period based on resource consumption information being obtained for each intake in each of the one or more intervals and based on objective performance information being obtained for each of the one or more intervals; and determining that the first period is a qualifying period based on a quantity of the one or more complete intervals in the first period meeting or exceeding a threshold.

5. The method of claim 1, wherein generating the expected objective performance comprises:

determining a quantity of complete intervals in the one or more intervals in the first period based on a quantity of intervals in the one or more intervals in the first period for which resource consumption information has been obtained for each intake and for which objective performance information has been obtained;

determining that the quantity of complete intervals in the first period fails to meet or exceed a threshold;

receiving, from the client computer, metrics for a third period, the metrics for the third period being based on the consumption instruction and a monitoring of the agent, the metrics for the third period being associated with a quantity of complete intervals in the third period, the complete intervals in the third period being associated with a third phase in the third period, the quantity of complete intervals in the third period meeting or exceeding the threshold; and generating the expected objective performance based on one or more portions of the obtained metrics for the third period, one or more portions of the obtained metrics for the second period, and a duration between the second phase in the second period and the third phase in the third period.

6. The method of claim 1, further comprising providing one or more alerts to one or more performance monitors based on the comparison indicating that one or more metrics for the first period or the second period diverged from one or more expected values by an amount that meets or exceeds one or more thresholds.

7. The method of claim 1, wherein the predicted expenditure amount includes an amount of calories.

8. The method of claim 1, wherein the first and second reportedly consumed amounts of specific units include amounts of metric system units, amounts of United States customary system units, or amounts of imperial system units, wherein the first and second reportedly consumed amounts of normalized units include quantities of serving sizes.

9. The method of claim 1, wherein the first and second reportedly consumed amounts of specific units include amounts of mass, and the first and second reportedly consumed amounts of normalized units include amounts of volume or quantities of pieces.

10. The method of claim 1, wherein the sensor includes a client camera, a client scale, a client accelerometer, or a client global positioning system (GPS) receiver, the one or more portions of the metrics for the first period include a first image of the agent captured by the client camera, a first weight of the agent sensed by the client scale, a first number of steps by the agent sensed by the client accelerometer, or a first change in determined physical locations of the client computer or the agent received from the client GPS receiver, and the one or more portions of the metrics for the second period include a second image of the agent, a second weight of the agent, a second number of steps by the agent, or a second change in determined physical locations.

11. The method of claim 1, wherein the one or more portions of the metrics for the first period include a first image of the agent, a first weight of the agent, a first number of steps by the agent, or a change in determined physical locations of the client computer or the agent, and the one or more portions of the metrics for the second period include a second image of the agent, a second weight of the agent, a second number of steps by the agent, or a second change in determined physical locations.

12. A system for improving performance criterion in a control session, the system comprising:

a network computer, comprising:

one or more transceivers that communicate over a network;

memory that stores instructions; and one or more processors that execute instructions associated with the network computer that cause the one or more processors of the network computer to perform actions, the actions comprising:

obtaining characteristics information associated with an agent;

logically associating the characteristics information with the agent in an agent repository, the agent repository including a database that includes agent data objects that have identifiers and characteristics information associated with respective ones of a plurality of agents, the agent repository logically associating the plurality of agents with different control sessions;

generating one or more outputs based on the characteristics information of the agent in the database and a performance model, wherein the one or more outputs include a predicted expenditure amount;

generating a consumption instruction to control resource consumption by the agent based on the predicted expenditure amount;

transmitting the consumption instruction to a client computer associated with the agent, the client computer including a display, a sensor or sensor interface coupled to at least one of a camera, a scale, an accelerometer, or a global positioning system (GPS) receiver that monitor metrics, wherein the metrics include at least one of in image of the agent captured by the camera, a weight of the agent using the scale, a number of steps of the agent using the accelerometer, and a change in determined physical locations of the client computer or the agent received from the GPS receiver;

receiving, from the client computer, first information metrics corresponding to at least one of the image, weight, number of steps, or change in determined physical locations for a first period associated with a first timestamp, the first information metrics for the first period being based on the consumption instruction and a monitoring of the agent, the monitoring of the agent including collecting by the sensor or receiving at the sensor interface, one or more portions of the first information metrics for the first period, the first information metrics for the first period being associated with one or more intervals in a plurality of intervals in the first period, the one or more intervals in the first period being associated with a first phase in the first period;

receiving, from the client computer, second information metrics corresponding to at least one of the image, weight, number of steps, or change in determined physical locations for a second period, the second information metrics for the second period being based on the consumption instruction and the monitoring of the agent including collecting by the sensor or receiving at the sensor interface, one or more portions of the second information metrics for the second period, the second information metrics for the second period being associated with one or more intervals in a plurality of intervals in the second period, the one or more intervals in the second period being associated with a second phase in the second period;

generating an expected objective performance based on at least one portion of the obtained first information metrics for the first period, at least one portion of the obtained second information metrics for the second period, and a duration between the first phase in the first period and the second phase in the second period;

comparing the expected objective performance to a difference between the one or more portions of the obtained first information metrics for the first period and the one or more portions of the obtained second information metrics for the second period;

modifying the predicted expenditure amount based on the comparison to increase a correlation between the one or more outputs and the obtained second information metrics for the second period;

generating a modified consumption instruction to control the resource consumption by the agent based on the modified predicted expenditure amount; and transmitting the modified consumption instruction to the client computer for visual representation on a display, wherein the consumption instruction indicates one or more specific-units amounts for one or more of multiple resource types and normalized-units amounts for one or more of the multiple resource types, and receiving metrics for the first period comprises:

receiving, from the client computer, metrics that indicate reportedly consumed amounts of specific units of one or more of the multiple resource types;

transforming the reportedly consumed amounts of specific units of one or more of the multiple resource types into reportedly consumed amounts of normalized units of one or more of the multiple resource types based on the specific-units amounts of one or more of the multiple resource types and the normalized-units amounts of one or more of the multiple resource types; and transforming the reportedly consumed amounts of normalized units of one or more of the multiple resource types into total reportedly consumed amounts of specific units of one or more of the multiple resource types based on one or more reportedly consumed amounts of normalized units of one or more other ones of the multiple resource types; and the client computer, comprising:

the display;

the sensor or a sensor interface to receive metrics associated with the agent from the sensor or from the sensor interface;

one or more transceivers that communicate over the network;

memory that stores instructions; and one or more processors that execute instructions associated with the client computer that cause the one or more processors of the client computer to perform actions, the actions comprising:

monitoring one or more actions of the agent;

transmitting, to the network computer, the first information metrics for the first period and the second information metrics for the second period based on the monitored one or more actions of the agent by at least one of comparing the images of the agent, aggregating the weight of the agent, determining the movement of the agent, or comparing location values d received by the client computer from the sensor or sensor interface as the one or more portions of the first information metrics for the first period or the one or more portions of the second information metrics for the second period; and displaying a visual representation of the modified consumption instruction on the display, and synchronizing the client computer with the network computer in response to the client computer rejoining the network, wherein the network computer provides the client computer at least updated characteristics information based on a comparison between a first timestamp associated with a most-recent update of the characteristics information at the client computer with a second timestamp associated with the updated characteristics information.

13. The system of claim 12, wherein generating an expected objective performance comprising:

generating an expected objective performance per interval based on one or more portions of the obtained first information metrics for the first period and one or more portions of the obtained second information metrics for the second period; and generating the expected objective performance based on the expected objective performance per interval and a number of intervals between the first phase in the first period and the second phase in the second period.

14. The system of claim 12, wherein modifying the predicted expenditure amount comprising:
    generating an objective performance divergence per interval based on the comparison; and
    modifying the predicted expenditure amount by a value of the objective performance divergence per interval.

15. The system of claim 12, wherein receiving the first information metrics for the first period comprising:
    determining that the one or more intervals in the first period are one or more complete intervals in the first period based on resource consumption information being obtained for each intake in each of the one or more intervals and based on objective performance information being obtained for each of the one or more intervals; and
    determining that the first period is a qualifying period based on a quantity of the one or more complete intervals in the first period meeting or exceeding a threshold.

16. The system of claim 12, wherein generating the expected objective performance comprising:
    determining a quantity of complete intervals in the one or more intervals in the first period based on a quantity of intervals in the one or more intervals in the first period for which resource consumption information has been obtained for each intake and for which objective performance information has been obtained;
    determining that the quantity of complete intervals in the first period fails to meet or exceed a threshold;
    receiving, from the client computer, third information corresponding to metrics for a third period, the third information metrics for the third period being based on the consumption instruction and a monitoring of the agent, the third information metrics for the third period being associated with a quantity of complete intervals in the third period, the complete intervals in the third period being associated with a third phase in the third period, the quantity of complete intervals in the third period meeting or exceeding the threshold; and
    generating the expected objective performance based on one or more portions of the obtained third information metrics for the third period, one or more portions of the obtained second information metrics for the second period, and a duration between the second phase in the second period and the third phase in the third period.

17. The system of claim 12, wherein the instructions associated with the network computer cause the one or more processors of the network computer to perform further actions, the further actions comprising providing one or more alerts to one or more performance monitors based on the comparison indicating that one or more first information metrics for the first period or the second information metrics of the second period diverged from one or more expected values by an amount that meets or exceeds one or more thresholds.

18. The system of claim 12, wherein the predicted expenditure amount includes an amount of calories.

19. The system of claim 12, wherein the reportedly consumed amounts of specific units include amounts of metric system units, amounts of United States customary system units, or amounts of imperial system units, wherein the reportedly consumed amounts of normalized units include quantities of serving sizes.

20. The system of claim 12, wherein the reportedly consumed amounts of specific units include amounts of mass, and the reportedly consumed amounts of normalized units include amounts of volume or quantities of pieces.

21. The system of claim 12, wherein the sensor includes a client camera, a client scale, a client accelerometer, or a client global positioning system (GPS) receiver, the one or more portions of the first information metrics for the first period include a first image of the agent captured by the client camera, a first weight of the agent sensed by the client scale, a first number of steps by the agent sensed by the client accelerometer, or a first change in determined physical locations of the client computer or the agent received from the client GPS receiver, and the one or more portions of the second information metrics for the second period include a second image of the agent, a second weight of the agent, a second number of steps by the agent, or a second change in determined physical locations.

22. The system of claim 12, wherein the one or more portions of the first information metrics for the first period include a first image of the agent, a first weight of the agent, a first number of steps by the agent, or a first change in determined physical locations of the client computer or the agent, and the one or more portions of the second information metrics for the second period include a second image of the agent, a second weight of the agent, a second number of steps by the agent, or a second change in determined physical locations.

23. A network computer for improving performance criterion in a control session, comprising:
    one or more transceivers that communicate over a network;
    memory that stores instructions; and
    one or more processors that execute instructions associated with the network computer that cause the one or more processors to perform actions, the actions comprising:
        obtaining characteristics information associated with an agent;
        logically associating the characteristics information with the agent in an agent repository, the agent repository logically associating characteristics information and metrics of a plurality of agents with respective ones of the plurality of agents, the agent repository logically associating the plurality of agents with different control sessions;
        generating one or more outputs based on the characteristics information of the agent and a performance model, wherein the one or more outputs include a predicted expenditure amount;
        generating a consumption instruction to control resource consumption by the agent based on the predicted expenditure amount;
        transmitting the consumption instruction to a client computer associated with the agent, the client computer including a display and a sensor or a sensor interface coupled to at least one of a camera that captures an image of the agent, a scale that measures a weight of the agent, an accelerometer that measures a number of steps by the agent, or a global positioning system (GPS) receiver that senses a change in determined physical locations of the client computer or the agent, to receive metrics associated with the agent from the sensor;
        receiving, from the client computer, first information metrics corresponding to at least one of the image, weight, number of steps, and change in determined physical locations associated with the agent for a first period, the first information metrics for the first period being based on the consumption instruction and a monitoring of the agent, the monitoring of the agent including collecting, by the sensor, one or more portions of the first information metrics for the first period, the first information metrics for the first period being associated with one or more intervals in a plurality of intervals in the first period, the one or more intervals in the first period being associated with a first phase in the first period, the first information metrics for the first period including a first reportedly consumed amount of normalized units of a first resource type and a second reportedly consumed amount of normalized units of a second resource type;

receiving, from the client computer, second information metrics corresponding to at least one of the image, weight, number of steps, change in determined physical locations for a second period, the second information metrics for the second period being based on the consumption instruction and the monitoring of the agent including collecting, by the sensor, one or more portions of the second information metrics for the second period, the second information metrics for the second period being associated with one or more intervals in a plurality of intervals in the second period, the one or more intervals in the second period being associated with a second phase in the second period;

logically associating the first information metrics for the first period defined by a first time stamp and the second information metrics for the second period defined by a second time stamp with the agent in the agent repository;

transforming the first reportedly consumed amount of normalized units of the first resource type into a first reportedly consumed amount of specific units of the first resource type;

transforming the second reportedly consumed amount of normalized units of the second resource type into a second reportedly consumed amount of specific units of the second resource type based on the first reportedly consumed amount of normalized units of the first resource type;

transforming the first reportedly consumed amount of specific units of the first resource type and the second reportedly consumed amount of specific units of the second resource type into a first total reportedly consumed amount;

generating an expected objective performance based on at least one portion of the obtained first information metrics for the first period including the first total reportedly consumed amount, at least one portion of the obtained second information metrics for the second period, and a duration between the first phase in the first period and the second phase in the second period;

comparing the expected objective performance to a difference between the one or more portions of the obtained first information metrics for the first period and the one or more portions of the obtained second information metrics for the second period;

modifying the predicted expenditure amount based on the comparison to increase a correlation between the one or more outputs and the obtained second information metrics for the second period;

generating a modified consumption instruction to control the resource consumption by the agent based on the modified predicted expenditure amount; and transmitting the modified consumption instruction to the client computer for visual representation on the display; and synchronizing the client computer with the network computer in response to the client computer rejoining the network, wherein the network computer provides the client computer at least updated characteristics information based on a comparison between a first timestamp associated with a most-recent update of the characteristics information at the client computer with a second timestamp associated with the updated characteristics information.

24. The network computer of claim 23, wherein generating an expected objective performance comprises:
   generating an expected objective performance per interval based on one or more portions of the obtained first information metrics for the first period and one or more portions of the obtained second information metrics for the second period; and
   generating the expected objective performance based on the expected objective performance per interval and a number of intervals between the first phase in the first period and the second phase in the second period.

25. The network computer of claim 23, wherein modifying the predicted expenditure amount comprises:
   generating an objective performance divergence per interval based on the comparison; and
   modifying the predicted expenditure amount by a value of the objective performance divergence per interval.

26. The network computer of claim 23, wherein receiving the first information metrics for the first period comprises:
   determining that the one or more intervals in the first period are one or more complete intervals in the first period based on resource consumption information being obtained for each intake in each of the one or more intervals and based on objective performance information being obtained for each of the one or more intervals; and
   determining that the first period is a qualifying period based on a quantity of the one or more complete intervals in the first period meeting or exceeding a threshold.

27. The network computer of claim 23, wherein generating the expected objective performance comprises:
   determining a quantity of complete intervals in the one or more intervals in the first period based on a quantity of intervals in the one or more intervals in the first period for which resource consumption information has been obtained for each intake and for which objective performance information has been obtained;
   determining that the quantity of complete intervals in the first period fails to meet or exceed a threshold;
   receiving, from the client computer, third information corresponding to metrics for a third period, the third information metrics for the third period being based on the consumption instruction and a monitoring of the agent, the third information metrics for the third period being associated with a quantity of complete intervals in the third period, the complete intervals in the third period being associated with a third phase in the third period, the quantity of complete intervals in the third period meeting or exceeding the threshold; and
   generating the expected objective performance based on one or more portions of the obtained third information metrics for the third period, one or more portions of the obtained second information metrics for the second period, and a duration between the second phase in the second period and the third phase in the third period.

28. The network computer of claim 23, wherein the instructions cause the one or more processors to perform further actions, the further actions comprising providing one or more alerts to one or more performance monitors based on the comparison indicating that one or more first information metrics for the first period or second information metrics of the second period diverged from one or more expected values by an amount that meets or exceeds one or more thresholds.

29. The network computer of claim 23, wherein the predicted expenditure amount includes an amount of calories.

30. The network computer of claim 23, wherein the first and second reportedly consumed amounts of specific units include amounts of metric system units, amounts of United States customary system units, or amounts of imperial system units, wherein the first and second reportedly consumed amounts of normalized units include quantities of serving sizes.

31. The network computer of claim 23, wherein the first and second reportedly consumed amounts of specific units include amounts of mass, and the first and second reportedly consumed amounts of normalized units include amounts of volume or quantities of pieces.

32. The network computer of claim 23, wherein the sensor includes a client camera, a client scale, a client accelerometer, or a client global positioning system (GPS) receiver, the one or more portions of the first information metrics for the first period include a first image of the agent captured by the client camera, a first weight of the agent sensed by the client scale, a first number of steps by the agent sensed by the client accelerometer, or a first change in determined physical locations of the client computer or the agent received from the client GPS receiver, and the one or more portions of the second information metrics for the second period include a second image of the agent, a second weight of the agent, a second number of steps by the agent, or a second change in determined physical locations.

33. The network computer of claim 23, wherein the one or more portions of the first information metrics for the first period include a first image of the agent, a first weight of the agent, a first number of steps by the agent, or a change in determined physical locations of the client computer or the agent, and the one or more portions of the second information metrics for the second period include a second image of the agent, a second weight of the agent, a second number of steps by the agent, or a second change in determined physical locations.

34. A system for improving performance criterion in a control session, the system comprising:
   a network computer, comprising:
      one or more transceivers that communicate over a network;
      memory that stores instructions; and
      one or more processors that execute instructions associated with the network computer that cause the one or more processors of the network computer to perform actions, the actions comprising:
         obtaining characteristics information associated with an agent;
         logically associating the characteristics information with the agent in an agent repository, the agent repository logically associating characteristics information of a plurality of agents with respective ones of the plurality of agents, the agent repository logically associating the plurality of agents with different control sessions;
         generating one or more outputs based on the characteristics information of the agent and a performance model, wherein the one or more outputs include a predicted expenditure amount;
         generating a consumption instruction to control resource consumption by the agent based on the predicted expenditure amount;
         transmitting the consumption instruction to a client computer associated with the agent;
         receiving, from the client computer, first metrics for a first period, the first metrics for the first period identified by a first timestamp included in the first metrics and being based on the consumption instruction and a monitoring of the agent, the monitoring of the agent including collecting by a sensor or receiving at a sensor interface, one or more portions of the first metrics for the first period, the first metrics for the first period being associated with one or more intervals in a plurality of intervals in the first period, the one or more intervals in the first period being associated with a first phase in the first period, the first metrics for the first period including a first reportedly consumed amount of normalized units of a first resource type and a second reportedly consumed amount of normalized units of a second resource type;
         receiving, from the client computer, second metrics for a second period identified by a second time stamp included in the second metrics when the client computer rejoins and synchronizes with the network after going offline subsequent to the first period, the second metrics for the second period being based on the consumption instruction and the monitoring of the agent including collecting by the sensor or receiving at the sensor interface, one or more portions of the second metrics for the second period, the second metrics for the second period being associated with one or more intervals in a plurality of intervals in the second period, the one or more intervals in the second period being associated with a second phase in the second period;
         transforming the first reportedly consumed amount of normalized units of the first resource type into a first reportedly consumed amount of specific units of the first resource type;
         transforming the second reportedly consumed amount of normalized units of the second resource type into a second reportedly consumed amount of specific units of the second resource type based on the first reportedly consumed amount of normalized units of the first resource type;
         transforming the first reportedly consumed amount of specific units of the first resource type and the second reportedly consumed amount of specific units of the second resource type into a first total reportedly consumed amount;
         generating an expected objective performance based on at least one portion of the obtained first metrics for the first period including the first total reportedly consumed amount, at least one portion of the obtained second metrics for the second period, and a duration between the first timestamp corresponding to the first phase in the first period and the second timestamp corresponding to the second phase in the second period;

comparing the expected objective performance to a difference between the one or more portions of the obtained first metrics for the first period and the one or more portions of the obtained second metrics for the second period;

modifying the predicted expenditure amount based on the comparison to increase a correlation between the one or more outputs and the obtained second metrics for the second period;

generating a modified consumption instruction to control the resource consumption by the agent based on the modified predicted expenditure amount;

transmitting the modified consumption instruction to the client computer for visual representation on a display; and synchronizing the client computer with the network computer in response to the client computer rejoining the network, wherein the network computer provides the client computer at least updated characteristics information based on a comparison between a first timestamp associated with a most-recent update of the characteristics information at the client computer with a second timestamp associated with the updated characteristics information; and the client computer, comprising:
the display;
the sensor or a sensor interface to receive metrics associated with the agent from the sensor;
one or more transceivers that communicate over the network;
memory that stores instructions; and
one or more processors that execute instructions associated with the client computer that cause the one or more processors of the client computer to perform actions, the actions comprising:
receiving the consumption instruction;
monitoring one or more actions of the agent;
transmitting, to the network computer, the first metrics for the first period and the second metrics for the second period based on the monitored one or more actions of the agent by aggregating values measured by the sensor and received by the client computer from the sensor as the one or more portions for the first period or the one or more portions of the second metrics for the second period;
receiving the modified consumption instruction; and
displaying a visual representation of the modified consumption instruction on the display.

35. The system of claim 34, wherein generating an expected objective performance comprising:
generating an expected objective performance per interval based on one or more portions of the obtained first metrics for the first period and one or more portions of the obtained second metrics for the second period; and
generating the expected objective performance based on the expected objective performance per interval and a number of intervals between the first phase in the first period and the second phase in the second period.

36. The system of claim 34, wherein modifying the predicted expenditure amount comprising:

generating an objective performance divergence per interval based on the comparison; and
modifying the predicted expenditure amount by a value of the objective performance divergence per interval.

37. The system of claim 34, wherein receiving the first metrics for the first period comprising:
determining that the one or more intervals in the first period are one or more complete intervals in the first period based on resource consumption information being obtained for each intake in each of the one or more intervals and based on objective performance information being obtained for each of the one or more intervals; and
determining that the first period is a qualifying period based on a quantity of the one or more complete intervals in the first period meeting or exceeding a threshold.

38. The system of claim 34, wherein generating the expected objective performance comprising:
determining a quantity of complete intervals in the one or more intervals in the first period based on a quantity of intervals in the one or more intervals in the first period for which resource consumption information has been obtained for each intake and for which objective performance information has been obtained;
determining that the quantity of complete intervals in the first period fails to meet or exceed a threshold;
receiving, from the client computer, metrics for a third period, the metrics for the third period being based on the consumption instruction and a monitoring of the agent, the metrics for the third period being associated with a quantity of complete intervals in the third period, the complete intervals in the third period being associated with a third phase in the third period, the quantity of complete intervals in the third period meeting or exceeding the threshold; and
generating the expected objective performance based on one or more portions of the obtained metrics for the third period, one or more portions of the obtained second metrics for the second period, and a duration between the second phase in the second period and the third phase in the third period.

39. The system of claim 34, wherein the instructions associated with the network computer cause the one or more processors of the network computer to perform further actions, the further actions comprising providing one or more alerts to one or more performance monitors based on the comparison indicating that one or more first metrics for the first period or the second metrics of the second period diverged from one or more expected values by an amount that meets or exceeds one or more thresholds.

40. The system of claim 34, wherein the sensor includes a camera, a scale, accelerometer, or global positioning system (GPS) receiver, the one or more portions of the first metrics for the first period include a first image of the agent captured by the camera, a first weight of the agent sensed by the scale, a first number of steps by the agent sensed by the accelerometer, or a first change in determined physical locations of the client computer or the agent received from the GPS receiver, and the one or more portions of the second metrics for the second period include a second image of the agent, a second weight of the agent, a second number of steps by the agent, or a second change in determined physical locations.

41. The system of claim 34, wherein the network computer further comprises at least one of a camera, a scale, an accelerometer, or a global positioning system (GPS)

receiver, to obtain the first metrics for the first period and the second metrics for the second period.

42. The system of claim 34, wherein the sensor interface is coupled to at least one of a camera, a scale, an accelerometer, or a global positioning system (GPS) receiver, to receive the first metrics for the first period and the second metrics for the second period.

43. The system of claim 34, wherein the predicted expenditure amount includes an amount of calories.

44. The system of claim 34, wherein the first and second reportedly consumed amounts of specific units include amounts of metric system units, amounts of United States customary system units, or amounts of imperial system units, wherein the first and second reportedly consumed amounts of normalized units include quantities of serving sizes.

45. The system of claim 34, wherein the first and second reportedly consumed amounts of specific units include amounts of mass, and the first and second reportedly consumed amounts of normalized units include amounts of volume or quantities of pieces.

* * * * *